US008604218B2

(12) United States Patent
Lampe et al.

(10) Patent No.: US 8,604,218 B2
(45) Date of Patent: Dec. 10, 2013

(54) CYTOSKELETAL ACTIVE RHO KINASE INHIBITOR COMPOUNDS, COMPOSITION AND USE

(75) Inventors: John W. Lampe, Cary, NC (US); Paul S. Watson, Carrboro, NC (US); David J. Slade, Durham, NC (US); Ward M. Peterson, Morrisville, NC (US); Christopher S. Crean, Pittsboro, NC (US); Jason L. Vittitow, Durham, NC (US); Jonathan Bryan DeCamp, Raleigh, NC (US); Nicholas F. Pelz, Durham, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 255 days.

(21) Appl. No.: 13/273,043

(22) Filed: Oct. 13, 2011

(65) Prior Publication Data

US 2012/0046275 A1    Feb. 23, 2012

Related U.S. Application Data

(62) Division of application No. 11/958,214, filed on Dec. 17, 2007, now Pat. No. 8,071,779.

(60) Provisional application No. 60/870,555, filed on Dec. 18, 2006.

(51) Int. Cl.
*C07D 231/56*     (2006.01)
*C07D 421/00*     (2006.01)

(52) U.S. Cl.
USPC ........................................ 548/362.5; 546/208

(58) Field of Classification Search
USPC ........................................ 548/362.5; 546/208
See application file for complete search history.

(56) References Cited

U.S. PATENT DOCUMENTS

| | | | |
|---|---|---|---|
| 6,555,539 B2 | 4/2003 | Reich et al. |
| 6,831,175 B2 | 12/2004 | Li et al. |
| 6,867,221 B2 | 3/2005 | Kodama et al. |
| 6,906,070 B2 | 6/2005 | Lam et al. |
| 6,982,274 B2 | 1/2006 | Oinuma et al. |
| 7,217,722 B2 | 5/2007 | Takami et al. |
| 7,615,564 B2 | 11/2009 | Iwakubo et al. |
| 2004/0106646 A1 | 6/2004 | Takayama et al. |
| 2004/0138286 A1 | 7/2004 | Imazaki et al. |
| 2005/0148640 A1 | 7/2005 | Come et al. |
| 2006/0167043 A1 | 7/2006 | Iwakubo et al. |
| 2006/0183906 A1 | 8/2006 | Rodgers et al. |
| 2007/0054916 A1 | 3/2007 | Patel et al. |
| 2007/0135479 A1 | 6/2007 | Ray et al. |

FOREIGN PATENT DOCUMENTS

| | | |
|---|---|---|
| EP | 1256574 A1 | 11/2002 |
| EP | 1403255 A1 | 3/2004 |
| EP | 1541151 A1 | 6/2005 |
| EP | 1550660 | 7/2005 |
| WO | WO 01/56988 A1 | 8/2001 |
| WO | WO-0156988 | 8/2001 |
| WO | WO 02/068406 | 9/2002 |
| WO | WO-03042172 | 5/2003 |
| WO | WO 2006/051311 | 5/2006 |
| WO | WO 2006/127587 | 11/2006 |
| WO | 2006135383 | * 12/2006 |
| WO | WO 2006/135383 | 12/2006 |
| WO | WO 2007/007919 | 1/2007 |

OTHER PUBLICATIONS

Dorwald F. A. Side Reactions in Organic Synthesis, 2005, Wiley: VCH, Weinheim p. IX of Preface p. 1-15.*
Venkatesh et al., Role of the Development Scientist in Compound Lead Selection and Optimization J. Pharm. Sci. 89, 145-54 (2000).*
Iwakubo et al. Bioorganic & Medicinal Chemistry 15 (2007) 350-364.*
Takami, et al., "Design and synthesis of Rho kinase inhibitors (I)," Bioorganic & Medicinal Chem 12 (2004) 2115-2137.
Iwakubo, et al., "Design and synthesis of Rho kinase inhibitors (II)," Bioorganic & Medicinal Chem 15 (2007) 350-364.
Iwakubo, et al., "Design and synthesis of Rho kinase inhibitors (III)," Bioorganic & Medicinal Chem 15 (2007) 1022-1033.
Shimizu et al., "Parallel Coiled-coil Association of the RhoA-binding Domain in Rho-kinase," The Journal of Biological Chemistry, vol. 278, No. 46, Nov. 14, 2003, pp. 46046-46051.
International Search Report for PCT/US07/87973, mailed May 9, 2008.
Supplementary European Search Report, Jul. 14, 2011.

* cited by examiner

*Primary Examiner* — Nizal Chandrakumar
(74) *Attorney, Agent, or Firm* — Laura M. Ginkel

(57) ABSTRACT

The present invention is directed to synthetic cytoskeletal active compounds that are inhibitors of rho-associated protein kinase. The present invention is also directed to pharmaceutical compositions comprising such compounds and a pharmaceutically acceptable carrier. The invention is additionally directed to a method of preventing or treating diseases or conditions associated with cytoskeletal reorganization. In one embodiment of the invention, the method treats increased intraocular pressure, such as primary open-angle glaucoma. The method comprises administering to a subject a therapeutically effective amount of a cytoskeletal active compound of Formula I or Formula II, wherein said amount is effective to influence the actomyosin interactions, for example by leading to cellular relaxation and alterations in cell-substratum adhesions.

20 Claims, 4 Drawing Sheets

CYTOSKELETAL ACTIVE RHO KINASE INHIBITOR COMPOUNDS, COMPOSITION AND USE

This application is a divisional of U.S. application Ser. No. 11/958,214, filed Dec. 17, 2007 now U.S. Pat. No. 8,071,779; which claims the benefit of U.S. Provisional Application No. 60/870,555, filed Dec. 18, 2006; the contents of the above applications are incorporated herein by reference in their entirety.

TECHNICAL FIELD

This invention relates to synthetic cytoskeletal active compounds, such as rho-associated kinase (ROCK) inhibiting compounds, and the methods of making such compounds. The invention also relates to using such compounds in the prevention or treatment of diseases or disorders that are affected or can be assisted by altering the integrity or rearrangement of the cytoskeleton, including but not exclusive of actomyosin interactions, tight junctional and focal adhesion complexes, for example, the treatment of disorders in which intraocular pressure is elevated, such as primary open-angle glaucoma.

BACKGROUND OF THE INVENTION

Glaucoma is an ophthalmic disease that leads to irreversible visual impairment. It is the fourth most common cause of blindness and the second most common cause of visual loss in the United States, and the most common cause of irreversible visual loss among African-Americans. Generally speaking, the disease is characterized by a progressive optic neuropathy caused at least in part by deleterious effects resulting from increased intraocular pressure. In normal individuals, intraocular pressures range from 12 to 20 mm Hg, averaging approximately 16 mm Hg. However, in individuals suffering from primary open angle glaucoma, intraocular pressures generally rise above 22 to 30 mm Hg. In angle closure or acute glaucoma intraocular pressure can reach as high as 70 mm Hg leading to blindness within only a few days. Interestingly, the loss of vision can result from statistically normal intraocular pressures in individuals with unusually pressure-sensitive eyes; a condition known as normotensive glaucoma. [See, e.g., P. L. Kaufman and T. W. Mittag, "Medical Therapy Of Glaucoma," Ch. 9, Sec. II (pp. 9.7-9.30) In P. L. Kaufman and T. W. Mittag (eds.): Glaucoma (Vol. 7 of S. M. Podos and M. Yanoff (eds): Textbook of Ophthalmology Series). London, Mosby-Year Book Europe Ltd. (1994); A. C. Guyton, Textbook of Medical Physiology (W. B. Saunders Co., Sixth Ed.), pp. 386-89 (1981)].

Open-angle glaucoma constitutes approximately 90% of all primary glaucomas and is characterized by abnormally high resistance to fluid (aqueous humor) drainage from the eye. Normal resistance is required to maintain an intraocular pressure sufficient to maintain the shape of the eye for optical integrity. This resistance is provided by the trabecular meshwork, a complex, multilaminar tissue consisting of specialized cells with a dense actomyosin cytoskeletal network, collagenous beams and extracellular matrix. The resistance of the trabecular meshwork normally is such that intraocular pressure is ~16 mm Hg, a pressure at which aqueous humor leaves the eye at the same rate at which it is produced (2.5 µL/minute). In the glaucomatous eye, the rate of aqueous humor production remains constant, while it is the increased resistance to outflow that is responsible for the elevated intraocular pressure.

Typical treatments for glaucoma comprise a variety of pharmaceutical approaches for reducing intraocular pressure (IOP), each with their drawbacks. Beta-blockers and carbonic anhydrase inhibitors reduce aqueous humor production, which is needed to nourish the avascular lens and corneal endothelial cells, and the prostaglandins effect the uvealscleral outflow pathway, which only accounts for 10% of the total outflow facility. There are currently no commercially approved therapeutic agents which act directly upon the trabecular meshwork, the site of aqueous humor drainage where increased resistance to aqueous humor outflow is responsible for elevated IOP. Therefore, a medical need remains for improved IOP-lowering medications that target this structure. Pharmacological agents which target the trabecular meshwork may provide relief to the significant numbers of patients that do not respond adequately to current IOP-lowering medications and/or cannot tolerate the side effects associated with these agents. Additionally, these molecules may prove beneficial as adjunctive therapy in combination with other classes of IOP-lowering medications.

U.S. Pat. Nos. 6,586,425, 6,110,912, and 5,798,380 disclose a method for the treatment of glaucoma using compounds that affect the actin filament integrity of the eye to enhance aqueous humor outflow. These patents also specifically disclose kinase inhibitors as well as latrunculin-A, latrunculin-B, swinholide-A, and jasplakinolide, which cause a perturbation of the actin cytoskeleton and tight junctional complexes in the trabecular meshwork or the modulation of its interactions with the underlying membrane. Perturbation of the cytoskeleton and the associated adhesions reduces the resistance of aqueous humor flow through the trabecular meshwork and thereby reduces intraocular pressure.

Wound healing is another approach in which these classes of molecules can aid in modulating IOP. Trabeculectomy is the most common form of glaucoma filtration surgery and remains as the first-line therapy for surgical reduction of pharmacologically uncontrolled intraocular pressure in primary open angle glaucoma. This procedure establishes a limbal fistula through which aqueous humor drains into the subconjunctival space establishing a filtering bleb to lower intraocular pressure. The success of the procedure is highly dependent on pharmacological modulation/inhibition of wound healing.

A major advance in the surgical management of glaucoma has been the use of antimetabolites to prevent scarring after glaucoma filtration surgery. Postoperative scarring of the filtering bleb is the most crucial factor in determining the short and long-term outcome of modern glaucoma filtration surgery. The antimetabolites mitomycin C (MMC) and 5-fluorouracil (5-FU) are widely used to suppress scarring and thus failure of the filtering bleb. In a large retrospective study, conventionally performed trabeculectomy has shown a failure rate of up to 30% within 3 months after surgery. To lower the incidence of this detrimental complication, various methods have been investigated in order to avoid scarring of the filtering bleb, mostly dealing with the intraoperative or postoperative application of antimetabolic drugs Despite their positive long-term effect on prolonged filtration, the application of cytotoxic drugs to a surgically opened eye increases the incidence of severe complications such as concomitant increases in vision threatening complications. MMC exhibits a high incidence of severe post-application complications, as does 5-FU; although its side effects mainly affect the corneal epithelium its clinical use is limited by severe pain and discomfort to the patient. No sufficient method has been established to achieve satisfying postoperative long-term surgical results with only minimal or no side effects for the patient.

There exists a need for effective and cost-practical cytoskeletal active compounds to treat glaucoma, to modulate wound healing after trabeculectomy, and to treat other diseases or disorders that are affected by the integrity of the actin cytoskeleton. ROCK inhibitors impact diverse physiological functions associated with cytoskeletal rearrangement leading to changes in cell morphology, cell contractility, cell motility and cytokinesis. They play a key role in modulating focal adhesion and stress fiber formation in trabecular meshwork cells which express a dense, dynamic cytoskeletal network. Thus, altering the contractility of these cells leads to drainage-surface expansion of the trabecular meshwork and Schlemm's canal. Additionally, loss of cell-substratum adhesions may influence paracellular fluid flow across Schlemm's canal or alter the fluid flow pathway through the juxtacanalicular tissue of the trabecular meshwork. Both are likely the basis for intraocular pressure-lowering effect of ROCK inhibitors. Thus, there exists a need for novel cytoskeletal active compounds that can be obtained using practical synthetic procedures.

SUMMARY OF THE INVENTION

The present invention is directed to compounds of Formula I and Formula II, which are inhibitors of rho kinase. The present invention is also directed to pharmaceutical compositions comprising such compounds and a pharmaceutically acceptable carrier.

The present invention is also directed to a method of preventing or treating diseases or conditions associated with cellular relaxation and/or changes in cell-substratum adhesions The invention provides a method of reducing intraocular pressure, including treating glaucoma such as primary open-angle glaucoma; a method of treating constriction of the visual field; a method of inhibiting wound healing after trabeculectomy; a method of treating posterior capsule opacification following extracapsular cataract extraction and intraocular lens implantation; a method of inhibiting angiogenesis; a method of modulating fluid transport on the ocular surface; a method of controlling vasospasm; a method of increasing tissue perfusion; a method of neuroprotection; and a method of vasoprotection to atherogenic agents.

The methods comprise the steps of identifying a subject in need of treatment, and administering to the subject a compound of Formula I or Formula II, in an amount effective to alter the actin cytoskeleton, such as by inhibiting actomyosin interactions.

BRIEF DESCRIPTION OF THE FIGURES

FIGS. 2-1 to 2-3 show the intraocular pressure of animals after treated with the test compounds or vehicle.

DETAILED DESCRIPTION OF THE INVENTION

Figure 1:
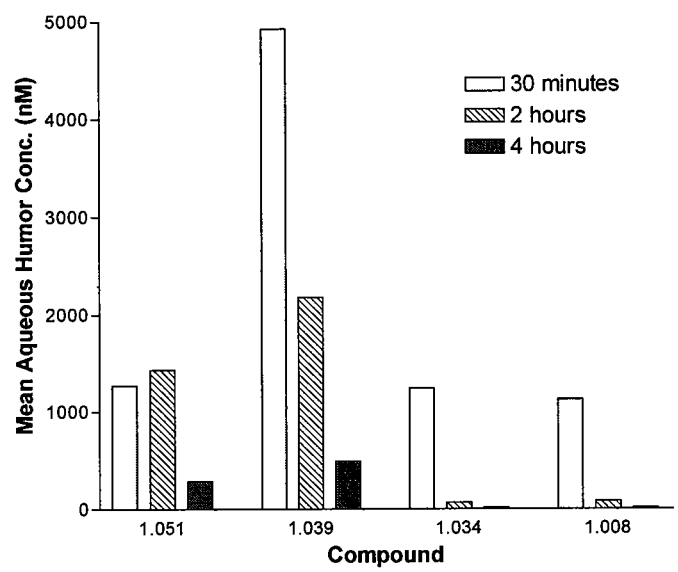
FIG. 1 shows the observed aqueous humor concentrations of the test compounds at 0.5, 2, and 4 hours after instillation of the compounds in the animal eyes.

The inventors of the present invention have discovered compounds that are cytoskeletal active agents, which modify cell contractility, cell-cell and cell-substrate interactions, for example by inhibiting actomyosin interactions. These compounds contain structural features that render them suitable for use as therapeutic agents, especially for use in topical formulations, for example for use in the treatment of ophthalmic disorders. The structures described herein provide new compounds with therapeutic utility.

DEFINITIONS

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl- groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl- groups preferably having from 2 to 6 carbon atoms in the alkenyl moiety and from 6 to 10 carbon atoms inclusively in the aryl moiety.

"Arylalkynyl" refers to aryl-alkynyl- groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl- groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl- groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl- groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl- groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl- groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl- groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

"Heterocycle-alkyl" refers to heterocycle-alkyl- groups preferably having from 1 to 6 carbon atoms inclusively in the alkyl moiety and from 6 to 10 atoms inclusively in the heterocycle moiety. Such heterocycle-alkyl groups are exemplified by morpholino-ethyl, pyrrolidinylmethyl, and the like.

"Heterocycle-alkenyl" refers to heterocycle-alkenyl- groups preferably having from 2 to 6 carbon atoms inclusively in the alkenyl moiety and from 6 to 10 atoms inclusively in the heterocycle moiety.

"Heterocycle-alkynyl" refers to heterocycle-alkynyl- groups preferably having from 2 to 6 carbon atoms inclusively in the alkynyl moiety and from 6 to 10 atoms inclusively in the heterocycle moiety.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

The term "heteroatom-containing substituent" refers to substituents containing at least one non-halogen heteroatom. Examples of such substituents include, but are not limited to, hydroxy, oxo, nitro, methoxy, ethoxy, alkoxy, substituted alkoxy, trifluoromethoxy, haloalkoxy, hydroxyalkyl, alkoxyalkyl, thio, alkylthio, acyl, carboxy, alkoxycarbonyl, carboxamido, substituted carboxamido, alkylsulfonyl, alkylsulfonylamino, sulfonamido, substituted sulfonamido, cyano, amino, substituted amino, alkylamino, dialkylamino, aminoalkyl, acylamino, amidino, amidoximo, hydroxamoyl, aryloxy, pyridyl, imidazolyl, heteroaryl, substituted heteroaryl, heteroaryloxy, heteroarylalkyl, heteroarylalkenyl, heteroarylalkynyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$.

"Tautomers" are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

"Solvates" are addition complexes in which a compound of Formula I or Formula II is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definitions of compounds in Formula I and Formula II encompass all possible hydrates and solvates, in any proportion, which possess the stated activity.

Rho Kinase Inhibitor Compounds

The rho kinase inhibitor compounds useful for this invention include compounds of general Formula I and Formula II, and/or tautomers thereof, and/or pharmaceutically-acceptable salts, and/or solvates, and/or hydrates thereof.

A compound according to Formula I or Formula II can exist in several diastereomeric forms. The general structures of Formula I and Formula II include all diastereomeric forms of such materials, when not specified otherwise. Formula I and Formula II also include mixtures of compounds of these Formulae, including mixtures of enantiomers, diastereomers and/or other isomers in any proportion.

A. Formula I

Compounds of Formula I are as follows:

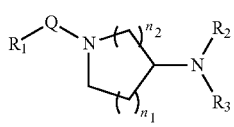

Formula I wherein:
$R_1$ is aryl or heteroaryl, optionally substituted;
Q is C=O, $SO_2$, or $(CR_4R_5)_{n3}$;
$n_1$ is 1, 2, or 3;
$n_2$ is 1 or 2;
$n_3$ is 0, 1, 2, or 3;

wherein the ring represented by

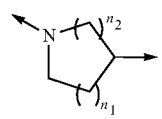

is optionally substituted by alkyl, halo, oxo, $OR_6$, $NR_6R_7$, or $SR_6$;

$R_2$ is selected from the following heteroaryl systems, optionally substituted:

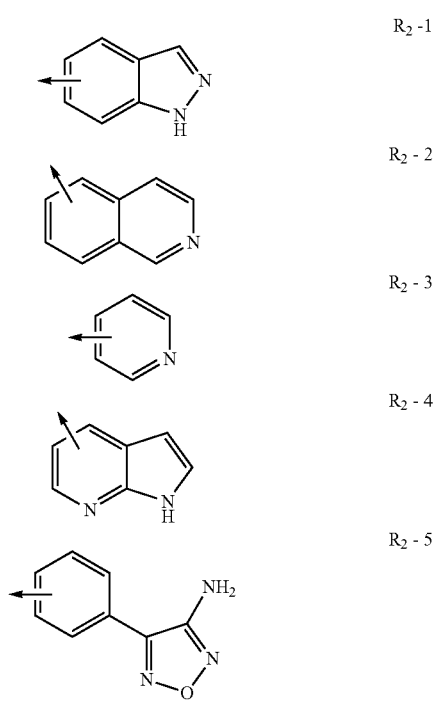

$R_3$-$R_7$ are independently H, alkyl, alkenyl, alkynyl, cycloalkyl, cycloalkenyl, cycloalkylalkyl, cycloalkylalkenyl, or cycloalkylalkynyl optionally substituted.

In Formula I, the preferred $R_1$ is substituted aryl, the more preferred $R_1$ is substituted phenyl, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, and the preferred $R_3$-$R_7$ are H.

[1] One embodiment of the invention is represented by Formula I, in which $R_2$ is 5-indazolyl or 6-indazolyl ($R_2$-1), optionally substituted.

[1a] In embodiment 1, $R_2$-1 is substituted by one or more alkyl or halo substituents.

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula I in which $R_2$ is 5-isoquinolinyl or 6-isoquinolinyl ($R_2$-2), optionally substituted.

[2a] In embodiment 2, $R_2$-2 is substituted by one or more alkyl or halo substituents.

[2b] In embodiment 2, $R_2$-2 is substituted by one or more amino, alkylamino, hydroxyl, or alkoxy substituents.

[2c] In embodiment 2, $R_2$-2 is unsubstituted.

[3] In another embodiment, the invention is represented by Formula I in which $R_2$ is 4-pyridyl or 3-pyridyl ($R_2$-3), optionally substituted.

[3a] In embodiment 3, $R_2$-3 is substituted by one or more alkyl or halo substituents.

[3b] In embodiment 3, $R_2$-3 is substituted by one or more amino, alkylamino, hydroxyl, or alkoxy substituents.

[3c] In embodiment 3, $R_2$-3 is unsubstituted.

[4] In another embodiment, the invention is represented by Formula I in which $R_2$ is 7-azaindol-4-yl or 7-azaindol-5-yl ($R_2$-4), optionally substituted.

[4a] In embodiment 4, $R_2$-4 is substituted by one or more alkyl or halo substituents.

[4b] In embodiment 4, $R_2$-4 is substituted by one or more amino, alkylamino, hydroxyl, or alkoxy substituents.

[4c] In embodiment 4, $R_2$-4 is unsubstituted.

[5] In another embodiment, the invention is represented by Formula I in which $R_2$ is 4-(3-amino-1,2,5-oxadiazol-4-yl)phenyl or 3-(3-amino-1,2,5-oxadiazol-4-yl)phenyl ($R_2$-5), optionally substituted.

[5a] In embodiment 5, $R_2$-5 is unsubstituted.

[6] In another embodiment, the invention is represented by Formula I in which $R_2$ is one of the groups $R_2$-1-$R_2$-5, substituted by one or more alkyl, halo, amino, alkylamino, hydroxyl, or alkoxy substituents.

[6a] In embodiment 6, $R_2$ is substituted by one or more alkyl or halo substituents.

[6b] In embodiment 6, $R_2$ is substituted by one or more amino, alkylamino, hydroxyl, or alkoxy substituents.

[7] In another embodiment, the invention is represented by Formula I in which $R_2$ is one of the groups $R_2$-1-$R_2$-5, and is unsubstituted.

[8] In another embodiment, the invention is represented by Formula I in which $R_3$ is H.

[9] In another embodiment, the invention is represented by Formula I in which Q is $(CR_4R_5)_{n3}$, and $n_3$ is 1 or 2.

[10] In another embodiment, the invention is represented by Formula I in which Q is $(CH_2)_{n3}$, and $n_3$ is 1.

[11] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table I.

[12] In another embodiment, the invention is represented by Formula I in which $R_1$ is aryl or heteroaryl substituted with one or more heteroatom-containing substituents, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S—".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table I.

[13] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, which are further substituted with one or more heteroatom-containing substituents, with the proviso that if the $R_1$ substituent is acyclic and its heteroatom-containing substituent falls on the carbon by which it is attached to $R_1$, then the heteroatom-containing substituent contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, and 1.122, shown below in Table I.

[14] In another embodiment, the invention is represented by Formula I in which $R_1$ is aryl or heteroaryl substituted with one or more alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, optionally further substituted, and $R_2$ is 5-indazolyl ($R_2$-1) or 5-isoquinolinyl ($R_2$-2), optionally substituted.

[14a] In embodiment 14, $R_2$ is 5-indazolyl ($R_2$-1), optionally substituted by one or more alkyl, halo, amino, alkylamino, hydroxyl, or alkoxy substituents.

[14b] In embodiment 14, $R_2$ is 5-isoquinolinyl ($R_2$-2), optionally substituted by one or more alkyl, halo, amino, alkylamino, hydroxyl, or alkoxy substituents.

[14c] In embodiment 14, $R_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table I.

[15] In another embodiment, the invention is represented by Formula I in which $R_1$ is aryl or heteroaryl substituted with one or more heteroatom-containing substituents, and $R_2$ is 5-indazolyl ($R_2$-1) or 5-isoquinolinyl ($R_2$-2), optionally substituted, with the proviso that if the $R_1$ substituent is acyclic and is connected to $R_1$ by a carbon atom, then this substituent contains at least one nitrogen or sulfur atom, with the second proviso that if the substituent is acyclic and is connected to $R_1$ by an oxygen or nitrogen atom, then this substituent contains at least one additional oxygen, nitrogen or sulfur atom, and with the third proviso that if the substituent is connected to $R_1$ by a sulfone linkage "—$SO_2$—", then $R_2$ is not nitrogen- or oxygen-substituted $R_2$-2.

[15a] In embodiment 15, $R_2$ is 5-indazolyl ($R_2$-1), optionally substituted by one or more alkyl, halo, amino, alkylamino, hydroxyl, or alkoxy substituents.

[15b] In embodiment 15, $R_2$ is 5-isoquinolinyl ($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table I.

[16] In another embodiment, the invention is represented by Formula I in which $R_1$ is aryl or heteroaryl substituted with one or more alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl substituents, at least one of which is further substituted with one or more heteroatom-containing substituents, and $R_2$ is 5-indazolyl ($R_2$-1) or 5-isoquinolinyl ($R_2$-2), optionally substituted, with the proviso that if the $R_1$ substituent is acyclic and its heteroatom-containing substituent falls on the carbon by which it is attached to $R_1$, then the heteroatom-containing substituent contains at least one nitrogen or sulfur atom.

[16a] In embodiment 16, $R_2$ is 5-indazolyl ($R_2$-1), optionally substituted by one or more alkyl, halo, amino, alkylamino, hydroxyl, or alkoxy substituents.

[16b] In embodiment 16, $R_2$ is 5-isoquinolinyl ($R_2$-2), optionally substituted by one or more alkyl, halo, amino, alkylamino, hydroxyl, or alkoxy substituents.

[16c] In embodiment 16, $R_2$ is unsubstituted.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, and 1.122, shown below in Table I.

B. Formula II

A preferred compound of Formula I is where $R_1$=Ar—X, shown below as Formula II:

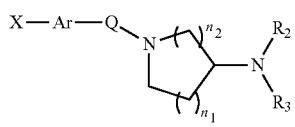

Formula II wherein:

Ar is a monocyclic or bicyclic aryl or heteroaryl ring, such as phenyl;

X is from 1 to 3 substituents on Ar, each independently in the form Y—Z, in which Z is attached to Ar;

Y is one or more substituents on Z, and each is chosen independently from H, halogen, or the heteroatom-containing substituents, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$;

Each instance of Z is chosen independently from alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, heterocycle, (heterocycle)alkyl, (heterocycle)alkenyl, (heterocycle)alkynyl, or is absent;

$R_8$ is H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, or $NR_{11}C(=O)NR_{12}R_{13}$;

$R_9$ and $R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents, including but not limited to $OR_{14}$, $NR_{14}R_{15}$, $NO_2$, $SR_{14}$, $SOR_{14}$, $SO_2R_{14}$, $SO_2NR_{14}R_{15}$, $NR_{14}SO_2R_{15}$, $OCF_3$, $CONR_{14}R_{15}$, $NR_{14}C(=O)R_{15}$, $NR_{14}C(=O)OR_{15}$, $OC(=O)NR_{14}R_{15}$, or $NR_{14}C(=O)NR_{15}R_{16}$;

any two of the groups $R_8$, $R_9$ and $R_{10}$ are optionally joined with a link selected from the group consisting of bond, —O—, —S—, —SO—, —SO$_2$—, and —NR$_{17}$— to form a ring;

$R_{11}$-$R_{17}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

In Formula II, the preferred Y is H, halogen, $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, the more preferred Y is H, halogen, $OR_8$, $SR_8$, $SOR_8$, $SO_2R_8$, $SO_2NR_8R_9$, $NR_8SO_2R_9$, $CONR_8R_9$, or $NR_8C(=O)NR_9R_{10}$, the preferred Z is alkyl, alkenyl, alkynyl, cycloalkyl, cycloalkenyl, cycloalkylalkyl, or is absent; the more preferred Z is alkyl, alkenyl, alkynyl, cycloalkyl, or is absent, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, the preferred $R_3$-$R_7$ are H, the preferred $R_8$ is H, alkyl, arylalkyl, cycloalkyl, cycloalkylalkyl, or heterocycle, the preferred $R_8$ substituents are H, halogen, $OR_{11}$, $NR_{11}R_{12}$, $SR_{11}$, $SOR_{11}$, $SO_2R_{11}$, $SO_2NR_{11}R_{12}$, $NR_{11}SO_2R_{12}$, $CONR_{11}R_{12}$, $NR_{11}C(=O)R_{12}$, and the preferred $R_9$-$R_{17}$ are H or alkyl.

[1] One embodiment of the invention is represented by Formula II in which $R_2$ is 5-indazolyl or 6-indazolyl ($R_2$-1), optionally substituted.

[1a] In embodiment 1, $R_2$-1 is substituted by one or more alkyl or halo substituents.

[1b] In embodiment 1, $R_2$-1 is substituted by one or more amino, alkylamino, hydroxyl, or alkoxy substituents.

[1c] In embodiment 1, $R_2$-1 is unsubstituted.

[2] In another embodiment, the invention is represented by Formula II in which $R_2$ is 5-isoquinolinyl or 6-isoquinolinyl ($R_2$-2), optionally substituted.

[2a] In embodiment 2, $R_2$-2 is substituted by one or more alkyl or halo substituents.

[2b] In embodiment 2, $R_2$-2 is substituted by one or more amino, alkylamino, hydroxyl, or alkoxy substituents.

[2c] In embodiment 2, $R_2$-2 is unsubstituted.

[3] In another embodiment, the invention is represented by Formula II in which $R_2$ is 4-pyridyl or 3-pyridyl ($R_2$-3), optionally substituted.

[3a] In embodiment 3, $R_2$-3 is substituted by one or more alkyl or halo substituents.

[3b] In embodiment 3, $R_2$-3 is substituted by one or more amino, alkylamino, hydroxyl, or alkoxy substituents.

[3c] In embodiment 3, $R_2$-3 is unsubstituted.

[4] In another embodiment, the invention is represented by Formula II in which $R_2$ is 7-azaindol-4-yl or 7-azaindol-5-yl ($R_2$-4), optionally substituted.

[4a] In embodiment 4, $R_2$-4 is substituted by one or more alkyl or halo substituents.

[4b] In embodiment 4, $R_2$-4 is substituted by one or more amino, alkylamino, hydroxyl, or alkoxy substituents.

[4c] In embodiment 4, $R_2$-4 is unsubstituted.

[5] In another embodiment, the invention is represented by Formula II in which $R_2$ is 4-(3-amino-1,2,5-oxadiazol-4-yl) phenyl or 3-(3-amino-1,2,5-oxadiazol-4-yl)phenyl ($R_2$-5), optionally substituted.

[5a] In embodiment 5, $R_2$-5 is unsubstituted.

[6] In another embodiment, the invention is represented by Formula II in which $R_2$ is one of the groups $R_2$-1-$R_2$-5, substituted by one or more alkyl, halo, amino, alkylamino, hydroxyl, or alkoxy substituents.

[6a] In embodiment 6, $R_2$ is substituted by one or more alkyl or halo substituents.

[6b] In embodiment 6, $R_2$ is substituted by one or more amino, alkylamino, hydroxyl, or alkoxy substituents.

[7] In another embodiment, the invention is represented by Formula II in which $R_2$ is one of the groups $R_2$-1-$R_2$-5, and is unsubstituted.

[8] In another embodiment, the invention is represented by Formula II in which $R_3$ is H.

[9] In another embodiment, the invention is represented by Formula II in which Q is $(CR_4R_5)_{n3}$, and $n_3$ is 1 or 2.

[10] In another embodiment, the invention is represented by Formula II in which Q is $(CH_2)_{n3}$, and $n_3$ is 1.

[11] In another embodiment, the invention is represented by Formula II in which Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkylalkenyl, cycloalkenyl, cycloalkylalkyl, heterocycle, (heterocycle)alkyl, (heterocycle)alkenyl, or (heterocycle)alkynyl.

Compounds exemplifying embodiment 11 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table I.

[12] In another embodiment, the invention is represented by Formula II in which Z is absent, Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, or $NR_8C(=O)NR_9R_{10}$, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$—", then $R_2$ is not nitrogen- or oxygen-substituted $R_2$-2.

[12a] In embodiment 12, the heteroatom-containing substituent is connected to $R_1$ by an oxygen or nitrogen atom.

[12b] In embodiment 12, the heteroatom-containing substituent is connected to $R_1$ by a sulfide linkage, "—S—".

Compounds exemplifying embodiment 12 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table I.

[13] In another embodiment, the invention is represented by Formula II in which Z is alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, with the proviso that if Z is acyclic and Y falls on the carbon by which Z is attached to Ar, then Y contains at least one nitrogen or sulfur atom.

Compounds exemplifying embodiment 13 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, and 1.122, shown below in Table I.

[14] In another embodiment, the invention is represented by Formula II in which Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and $R_2$ is 5-indazolyl ($R_2$-1) or 5-isoquinolinyl ($R_2$-2), optionally substituted.

[14a] In embodiment 14, $R_2$ is 5-indazolyl ($R_2$-1), optionally substituted by one or more alkyl, halo, amino, alkylamino, hydroxyl, or alkoxy substituents.

[14b] In embodiment 14, $R_2$ is 5-isoquinolinyl ($R_2$-2), optionally substituted by one or more alkyl, halo, amino, alkylamino, hydroxyl, or alkoxy substituents.

[14c] In embodiment 14, $R_2$ is unsubstituted.

Compounds exemplifying embodiment 14 include compounds 1.009, 1.010, 1.011, 1.012, 1.020, 1.021, 1.030, 1.034, 1.037, 1.044, 1.047, 1.076, 1.077, 1.083, 2.010, 2.011, 2.019, 2.020, 2.022, 2.023, and 2.031, shown below in Table I.

[15] In another embodiment, the invention is represented by Formula II in which Z is absent, Y is a heteroatom-containing substituent, including but not limited to $OR_8$, $NR_8R_9$, $SR_8$, $SOR_8$, $SO_2R_8$, $SO_2NR_8R_9$, $NR_8SO_2R_9$, $CONR_8R_9$, $NR_8C(=O)R_9$, $NR_8C(=O)OR_9$, $OC(=O)NR_8R_9$, or $NR_8C(=O)NR_9R_{10}$, and $R_2$ is 5-indazolyl ($R_2$-1) or 5-isoquinolinyl ($R_2$-2), optionally substituted, with the proviso that if the substituent Y is acyclic and is connected to Ar by a carbon atom, then this substituent contains at least one nitrogen or sulfur atom, with the second proviso that if the substituent Y is acyclic and is connected to Ar by an oxygen or nitrogen atom, then this substituent contains at least one additional oxygen, nitrogen or sulfur atom, and with the third proviso that if the substituent Y is connected to Ar by a sulfone linkage "—$SO_2$—", then $R_2$ is not nitrogen- or oxygen-substituted $R_2$-2.

[15a] In embodiment 15, $R_2$ is 5-indazolyl ($R_2$-1), optionally substituted by one or more alkyl, halo, amino, alkylamino, hydroxyl, or alkoxy substituents.

[15b] In embodiment 15, $R_2$ is 5-isoquinolinyl ($R_2$-2), optionally substituted by one or more alkyl, halo, amino, alkylamino, hydroxyl, or alkoxy substituents.

[15c] In embodiment 15, $R_2$ is unsubstituted.

[15d] In embodiment 15, the heteroatom-containing substituent is connected to $R_1$ by an oxygen or nitrogen atom.

[15e] In embodiment 15, the heteroatom-containing substituent is connected to $R_1$ by a sulfide linkage, "—S—".

Compounds exemplifying embodiment 15 include compounds 1.001, 1.002, 1.004, 1.005, 1.038, 1.048, 1.055, 1.056, 2.002, 2.003, 2.005, 2.007, 1.003, 1.006, 1.007, 1.018, 1.039, 1.051, 1.058, 1.060, 1.084, 1.085, 1.086, 1.087, 1.088, 1.090, 1.091, 1.092, 1.093, 1.094, 1.095, 1.096, 1.097, 1.098, 1.102, 1.111, 1.113, 1.115, 1.116, 1.117, 1.118, 1.120, 1.121, 1.123, 1.124, 1.125, 1.126, 1.127, 1.128, 1.129, 1.130, 2.004, 2.008, 2.032, 2.033, 2.034, 2.035, 2.036, 2.037, 2.038, 2.039, 2.040, 2.041, 2.042, 2.043, 2.044, 1.008, 1.017, 1.026, 1.040, 1.074, 1.075, 2.009, 2.012, 2.021, 2.024, 2.026, and 2.029, shown below in Table I.

[16] In another embodiment, the invention is represented by Formula II in which Z is alkyl, alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, or (heterocycle)alkynyl, and Y is a heteroatom-containing substituent, including but not limited to $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$, and $R_2$ is 5-indazolyl ($R_2$-1) or 5-isoquinolinyl ($R_2$-2), optionally substituted, with the proviso that if Z is acyclic and Y falls on the carbon by which Z is attached to Ar, then Y contains at least one nitrogen or sulfur atom.

[16a] In embodiment 16, $R_2$ is 5-indazolyl ($R_2$-1), optionally substituted by one or more alkyl, halo, amino, alkylamino, hydroxyl, or alkoxy substituents.

[16b] In embodiment 16, $R_2$ is 5-isoquinolinyl ($R_2$-2), optionally substituted by one or more alkyl, halo, amino, alkylamino, hydroxyl, or alkoxy substituents.

[16c] In embodiment 16, $R_2$ is unsubstituted.

Compounds exemplifying embodiment 16 include compounds 1.019, 1.027, 1.028, 1.029, 1.035, 1.041, 1.042, 1.043, 1.057, 1.061, 1.099, 1.101, 1.103, 1.104, 1.105, 1.106, 1.107, 1.108, 1.109, 1.112, 1.114, 1.119, and 1.122, shown below in Table I.

In Embodiments 11-16 of Formula II, the preferred Q is $(CR_4R_5)_{n3}$, the more preferred Q is $CH_2$, the preferred $n_1$ is 1 or 2, the preferred $n_2$ is 1, the preferred $n_3$ is 1 or 2, and the preferred $R_3$ is H.

The present compounds are useful for ophthalmic use, particularly in reducing intraocular pressure or treating glaucoma. To be therapeutically effective in ophthalmic use, the compounds must have both adequate potency and proper pharmacokinetic properties such as good permeability across the ocular surface. In general, compounds bearing polar functionality have preferred absorption properties and are particularly suitable for topical optical use. In general, compounds bearing small lipophilic functional groups have good ROCK inhibitory potency.

The inventors have discovered that the $R_1$ substitution in Formula I and X in Formula II are important factors for pharmacokinetic properties and ROCK inhibitory potency. The inventors have optimized and selected compounds that have improved ocular permeability and ROCK inhibitory potency. Specifically, compounds bearing polar functionality, especially those specified in the embodiments 11, 12, 13, 14, 15, and 16 in Formulae I and II, above, are particularly suitable for topical optical use with adequate ROCK inhibiting activity. Compounds bearing small lipophilic functional groups, as specified in the embodiments 11, 12, 13, 14, 15, and 16 in Formulae I and II, above, display ROCK inhibition with adequate ocular permeability.

Specific Compounds illustrative of Formula I and Formula II are shown in the following Table I. The example compounds have been numbered in such a way that numbers of the form 1.nnn indicate compounds in which $R_2$ is $R_2$-1, numbers of the form 2.nnn indicate compounds in which $R_2$ is $R_2$-2, and so on in a similar fashion for the remaining compound numbers and groups $R_2$. In the following structures, hydrogens are omitted from the drawings for the sake of simplicity. Tautomers drawn represent all tautomers possible. Structures are drawn to indicate the preferred stereochemistry; where stereoisomers may be generated in these compounds, structures are taken to mean any of the possible stereoisomers alone or a mixture of stereoisomers in any ratio.

TABLE I

Example Compounds.

| Compound | Structure | Embodiments |
|---|---|---|
| 1.001 | 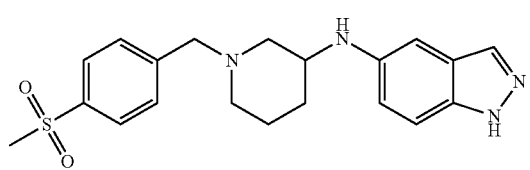 [SMILES: CS(=O)(=O)c1ccc(CN2CCCC(Nc3ccc4[nH]ncc4c3)C2)cc1]<br>N-(1-(4-(methylsulfonyl)benzyl)piperidin-3-yl)-1H-indazol-5-amine | 1c, 7, 8, 9, 10, 12, 15c |

TABLE I-continued

Example Compounds.

| Compound | Structure | Embodiments |
|---|---|---|
| 1.002 | 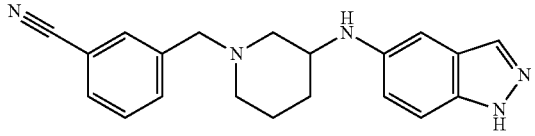 [SMILES: N#Cc1cccc(CN2CCCC(Nc3ccc4[nH]ncc4c3)C2)c1]<br>3-((3-(1H-indazol-5-ylamino)piperidin-1-yl)methyl)benzonitrile | 1c, 7, 8, 9, 10, 12, 15c |
| 1.003 | 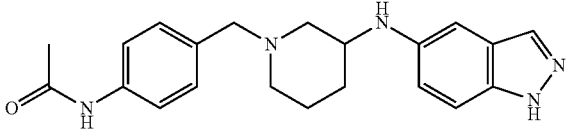 [SMILES: CC(=O)Nc1ccc(CN2CCCC(Nc3ccc4[nH]ncc4c3)C2)cc1]<br>N-(4-((3-(1H-indazol-5-ylamino)piperidin-1-yl)methyl)phenyl)acetamide | 1c, 7, 8, 9, 10, 12a, 15c, 15d |
| 1.004 | 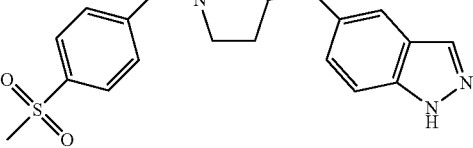<br>N-(1-(4-(methylsulfonyl)benzyl)pyrrolidin-3-yl)-1H-indazol-5-amine | 1c, 7, 8, 9, 10, 12, 15c |
| 1.005 | 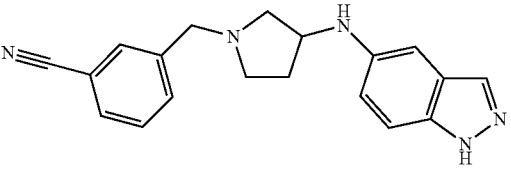 [SMILES: N#Cc1cccc(CN2CCC(Nc3ccc4[nH]ncc4c3)C2)c1]<br>3-((3-(1H-indazol-5-ylamino)pyrrolidin-1-yl)methyl)benzonitrile | 1c, 7, 8, 9, 10, 12, 15c |
| 1.006 | 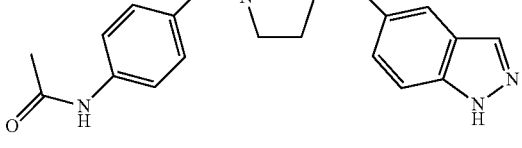<br>N-(4-((3-(1H-indazol-5-ylamino)pyrrolidin-1-yl)methyl)phenyl)acetamide | 1c, 7, 8, 9, 10, 12a, 15c, 15d |
| 1.007 | 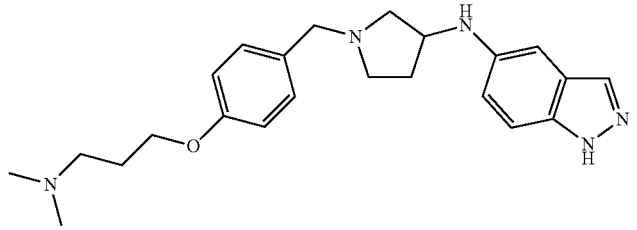 [SMILES: CN(C)CCCOc1ccc(CN2CCC(Nc3ccc4[nH]ncc4c3)C2)cc1]<br>N-(1-(4-(3-(dimethylamino)propoxy)benzyl)pyrrolidin-3-yl)-1H-indazol-5-amine | 1c, 7, 8, 9, 10, 12a, 15c, 15d |

TABLE I-continued

Example Compounds.

| Compound | Structure | Embodiments |
|---|---|---|
| 1.008 | N-(1-(4-(methylthio)benzyl)piperidin-3-yl)-1H-indazol-5-amine | 1c, 7, 8, 9, 10, 12b, 15c, 15e |
| 1.009 | N-(1-(biphenyl-4-ylmethyl)piperidin-3-yl)-1H-indazol-5-amine | 1c, 7, 8, 9, 10, 11, 14c |
| 1.010 | N-(1-(1H-imidazol-1-yl)benzyl)piperidin-3-yl)-1H-indazol-5-amine | 1c, 7, 8, 9, 10, 11, 14c |
| 1.011 | N-(1-(4-(pyrrolidin-1-yl)benzyl)piperidin-3-yl)-1H-indazol-5-amine | 1c, 7, 8, 9, 10, 11, 14c |
| 1.012 | N-(1-(4-morpholinobenzyl)piperidin-3-yl)-1H-indazol-5-amine | 1c, 7, 8, 9, 10, 11, 14c |
| 1.013 | N-(1-(4-isobutylbenzyl)piperidin-3-yl)-1H-indazol-5-amine | 1c, 7, 8, 9, 10 |

TABLE I-continued

Example Compounds.

| Compound | Structure | Embodiments |
| --- | --- | --- |
| 1.014 | N-(1-(4-butylbenzyl)piperidin-3-yl)-1H-indazol-5-amine | 1c, 7, 8, 9, 10 |
| 1.015 | N-(1-(4-isopropoxybenzyl)piperidin-3-yl)-1H-indazol-5-amine | 1c, 7, 8, 9, 10 |
| 1.016 | N-(1-(2,3-dimethylbenzyl)piperidin-3-yl)-1H-indazol-5-amine | 1c, 7, 8, 9, 10 |
| 1.017 | N-(1-(4-(ethylthio)benzyl)piperidin-3-yl)-1H-indazol-5-amine | 1c, 7, 8, 9, 10, 12b, 15c, 15e |
| 1.018 | 2-(4-((3-(1H-indazol-5-ylamino)piperidin-1-yl)methyl)phenoxy)ethanol | 1c, 7, 8, 9, 10, 12a, 15c, 15d |
| 1.019 | N-(1-(4-((dimethylamino)methyl)benzyl)piperidin-3-yl)-1H-indazol-5-amine | 1c, 7, 8, 9, 10, 13, 16c |
| 1.020 | N-(1-(4-cyclopropylbenzyl)piperidin-3-yl)-1H-indazol-5-amine | 1c, 7, 8, 9, 10, 11, 14c |

TABLE I-continued

Example Compounds.

| Compound | Structure | Embodiments |
|---|---|---|
| 1.021 | N-(1-(3-cyclopropylbenzyl)piperidin-3-yl)-1H-indazol-5-amine | 1c, 7, 8, 9, 10, 11, 14c |
| 1.022 | N-(1-(4-(trifluoromethoxy)benzyl)piperidin-3-yl)-1H-indazol-5-amine | 1c, 7, 8, 9, 10 |
| 1.023 | N-(1-(4-isopropylbenzyl)piperidin-3-yl)-1H-indazol-5-amine | 1c, 7, 8, 9, 10 |
| 1.024 | N-(1-(2,4-dimethylbenzyl)piperidin-3-yl)-1H-indazol-5-amine | 1c, 7, 8, 9, 10 |
| 1.025 | (4-((3-(1H-indazol-5-ylamino)piperidin-1-yl)methyl)phenyl)methanol | 1c, 7, 8, 9, 10 |
| 1.026 | N-(1-(4-(cyclopropylthio)benzyl)piperidin-3-yl)-1H-indazol-5-amine | 1c, 7, 8, 9, 10, 12b, 15c, 15e |
| 1.027 | tert-butyl 4-((3-(1H-indazol-5-ylamino)piperidin-1-yl)methyl)benzylcarbamate | 1c, 7, 8, 9, 10, 13, 16c |

TABLE I-continued

Example Compounds.

| Compound | Structure | Embodiments |
|---|---|---|
| 1.028 | N-(1-(4-(methylthiomethyl)benzyl)piperidin-3-yl)-1H-indazol-5-amine | 1c, 7, 8, 9, 10, 13, 16c |
| 1.029 | N-(1-(4-(methylsulfonylmethyl)benzyl)piperidin-3-yl)-1H-indazol-5-amine | 1c, 7, 8, 9, 10, 13, 16c |
| 1.030 | N-(1-(4-(thiophen-2-yl)benzyl)piperidin-3-yl)-1H-indazol-5-amine | 1c, 7, 8, 9, 10, 11, 14c |
| 1.031 | N-(1-benzylazepan-4-yl)-1H-indazol-5-amine | 1c, 7, 8, 9, 10 |
| 1.032 | N-(1-(4-(dimethylamino)benzyl)piperidin-3-yl)-1H-indazol-5-amine | 1c, 7, 8, 9, 10 |
| 1.033 | N-(1-(4-ethylbenzyl)piperidin-3-yl)-1H-indazol-5-amine | 1c, 7, 8, 9, 10 |
| 1.034 | N-(1-(4-ethynylbenzyl)piperidin-3-yl)-1H-indazol-5-amine | 1c, 7, 8, 9, 10, 11, 14c |

TABLE I-continued

Example Compounds.

| Compound | Structure | Embodiments |
|---|---|---|
| 1.035 | N-(1-(4-(aminomethyl)benzyl)piperidin-3-yl)-1H-indazol-5-amine | 1c, 7, 8, 9, 10, 13, 16c |
| 1.036 | 1-(4-((3-(1H-indazol-5-ylamino)piperidin-1-yl)methyl)phenyl)ethanone | 1c, 7, 8, 9, 10 |
| 1.037 | N-(1-(4-vinylbenzyl)piperidin-3-yl)-1H-indazol-5-amine | 1c, 7, 8, 9, 10, 11, 14c |
| 1.038 | 4-((3-(1H-indazol-5-ylamino)piperidin-1-yl)methyl)benzonitrile | 1c, 7, 8, 9, 10, 12, 15c |
| 1.039 | 2-(3-((3-(1H-indazol-5-ylamino)piperidin-1-yl)methyl)phenoxy)ethanol | 1c, 7, 8, 9, 10, 12a, 15c, 15d |
| 1.040 | N-(1-(3-(methylthio)benzyl)piperidin-3-yl)-1H-indazol-5-amine | 1c, 7, 8, 9, 10, 12b, 15c, 15e |
| 1.041 | N-(1-(3-(methylsulfonylmethyl)benzyl)piperidin-3-yl)-1H-indazol-5-amine | 1c, 7, 8, 9, 10, 13, 16c |

TABLE I-continued

Example Compounds.

| Compound | Structure | Embodiments |
|---|---|---|
| 1.042 | 3-(4-((3-(1H-indazol-5-ylamino)piperidin-1-yl)methyl)phenyl)prop-2-yn-1-ol | 1c, 7, 8, 9, 10, 13, 16c |
| 1.043 | 4-(4-((3-(1H-indazol-5-ylamino)piperidin-1-yl)methyl)phenyl)but-3-yn-1-ol | 1c, 7, 8, 9, 10, 13, 16c |
| 1.044 | N-(1-(4-(cyclopropylethynyl)benzyl)piperidin-3-yl)-1H-indazol-5-amine | 1c, 7, 8, 9, 10, 11, 14c |
| 1.045 | N-(1-(3-bromobenzyl)piperidin-3-yl)-1H-indazol-5-amine | 1c, 7, 8, 9, 10 |
| 1.046 | 3-((3-(1H-indazol-5-ylamino)piperidin-1-yl)methyl)phenol | 1c, 7, 8, 9, 10 |
| 1.047 | N-(1-(3-ethynylbenzyl)piperidin-3-yl)-1H-indazol-5-amine | 1c, 7, 8, 9, 10, 11, 14c |
| 1.048 | N-(1-(3-(methylsulfonyl)benzyl)piperidin-3-yl)-1H-indazol-5-amine | 1c, 7, 8, 9, 10, 12, 15c |

TABLE I-continued

Example Compounds.

| Compound | Structure | Embodiments |
|---|---|---|
| 1.049 | N-(1-benzylpiperidin-3-yl)-3-methyl-1H-indazol-5-amine | 1a, 6a, 8, 9, 10 |
| 1.050 | N5-(1-benzylpiperidin-3-yl)-1H-indazole-3,5-diamine | 1b, 6b, 8, 9, 10 |
| 1.051 | N-(3-((3-(1H-indazol-5-ylamino)piperidin-1-yl)methyl)phenyl)methanesulfonamide | 1c, 7, 8, 9, 10, 12a, 15c, 15d |
| 1.052 | N-(1-(benzofuran-5-ylmethyl)piperidin-3-yl)-1H-indazol-5-amine | 1c, 7, 8, 9, 10 |
| 1.053 | N-(1-((2,3-dihydrobenzo[b][1,4]dioxin-6-yl)methyl)piperidin-3-yl)-1H-indazol-5-amine | 1c, 7, 8, 9, 10 |
| 1.054 | N-(1-(benzo[b]thiophen-5-ylmethyl)piperidin-3-yl)-1H-indazol-5-amine | 1c, 7, 8, 9, 10 |
| 1.055 | 3-((3-(1H-indazol-5-ylamino)piperidin-1-yl)methyl)benzamide | 1c, 7, 8, 9, 10, 12, 15c |

TABLE I-continued

Example Compounds.

| Compound | Structure | Embodiments |
|---|---|---|
| 1.056 | 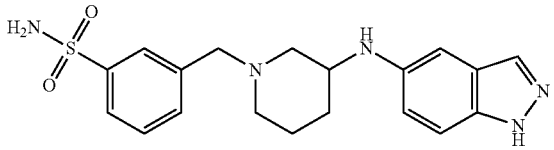 [SMILES: NS(=O)(=O)c1cccc(CN2CCCC(Nc3ccc4[nH]ncc4c3)C2)c1]<br>3-((3-(1H-indazol-5-ylamino)piperidin-1-yl)methyl)benzenesulfonamide | 1c, 7, 8, 9, 10, 12, 15c |
| 1.057 | 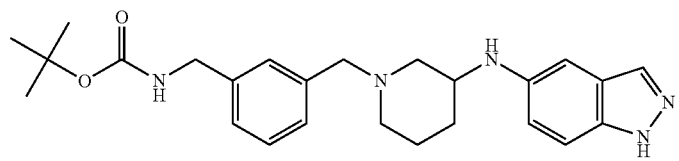 [SMILES: CC(C)(C)OC(=O)NCc1cccc(CN2CCCC(Nc3ccc4[nH]ncc4c3)C2)c1]<br>tert-butyl 3-((3-(1H-indazol-5-ylamino)piperidin-1-yl)methyl)benzylcarbamate | 1c, 7, 8, 9, 10, 13, 16c |
| 1.058 | 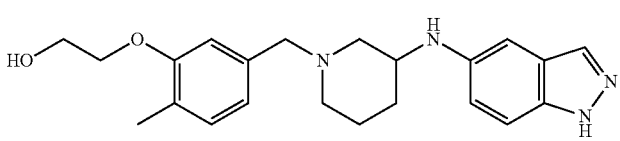 [SMILES: Cc1ccc(CN2CCCC(Nc3ccc4[nH]ncc4c3)C2)cc1OCCO]<br>2-(5-((3-(1H-indazol-5-ylamino)piperidin-1-yl)methyl)-2-methylphenoxy)ethanol | 1c, 7, 8, 9, 10, 12a, 15c, 15d |
| 1.059 | 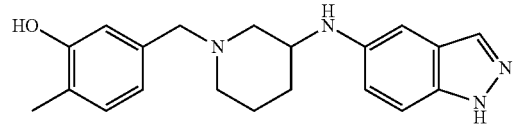 [SMILES: Cc1ccc(CN2CCCC(Nc3ccc4[nH]ncc4c3)C2)cc1O]<br>5-((3-(1H-indazol-5-ylamino)piperidin-1-yl)methyl)-2-methylphenol | 1c, 7, 8, 9, 10 |
| 1.060 | 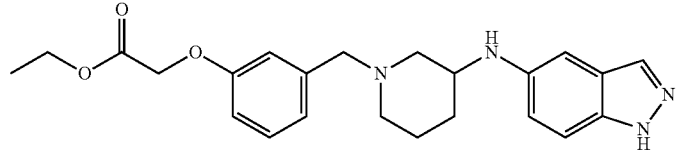 [SMILES: CCOC(=O)COc1cccc(CN2CCCC(Nc3ccc4[nH]ncc4c3)C2)c1]<br>ethyl 2-(3-((3-(1H-indazol-5-ylamino)piperidin-1-yl)methyl)phenoxy)acetate | 1c, 7, 8, 9, 10, 12a, 15c, 15d |
| 1.061 | 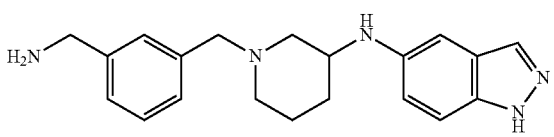 [SMILES: NCc1cccc(CN2CCCC(Nc3ccc4[nH]ncc4c3)C2)c1]<br>N-(1-(3-(aminomethyl)benzyl)piperidin-3-yl)-1H-indazol-5-amine | 1c, 7, 8, 9, 10, 13, 16c |
| 1.062 | 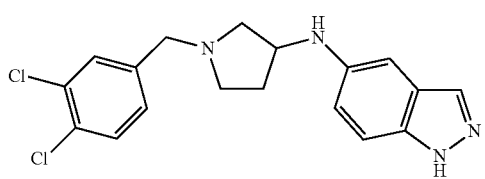 [SMILES: Clc1ccc(CN2CCC(Nc3ccc4[nH]ncc4c3)C2)cc1Cl]<br>N-(1-(3,4-dichlorobenzyl)pyrrolidin-3-yl)-1H-indazol-5-amine | 1c, 7, 8, 9, 10 |

TABLE I-continued

Example Compounds.

| Compound | Structure | Embodiments |
|---|---|---|
| 1.063 | 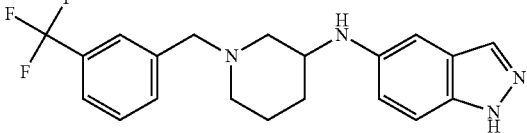<br>N-(1-(3-(trifluoromethyl)benzyl)piperidin-3-yl)-1H-indazol-5-amine | 1c, 7, 8, 9, 10 |
| 1.064 | 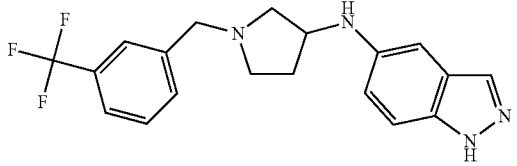 [SMILES: FC(F)(F)c1cccc(CN2CCC(Nc3ccc4[nH]ncc4c3)C2)c1]<br>N-(1-(3-(trifluoromethyl)benzyl)pyrrolidin-3-yl)-1H-indazol-5-amine | 1c, 7, 8, 9, 10 |
| 1.065 | 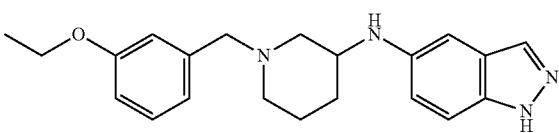 [SMILES: CCOc1cccc(CN2CCCC(Nc3ccc4[nH]ncc4c3)C2)c1]<br>N-(1-(3-ethoxybenzyl)piperidin-3-yl)-1H-indazol-5-amine | 1c, 7, 8, 9, 10 |
| 1.066 | 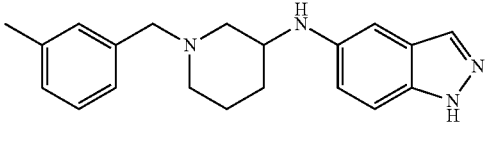 [SMILES: Cc1cccc(CN2CCCC(Nc3ccc4[nH]ncc4c3)C2)c1]<br>N-(1-(3-methylbenzyl)piperidin-3-yl)-1H-indazol-5-amine | 1c, 7, 8, 9, 10 |
| 1.067 | 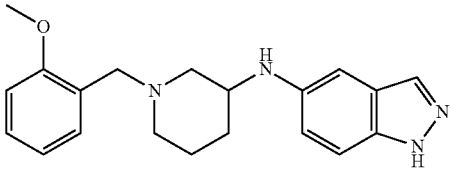 [SMILES: COc1ccccc1CN1CCCC(Nc2ccc3[nH]ncc3c2)C1]<br>N-(1-(2-methoxybenzyl)piperidin-3-yl)-1H-indazol-5-amine | 1c, 7, 8, 9, 10 |
| 1.068 | 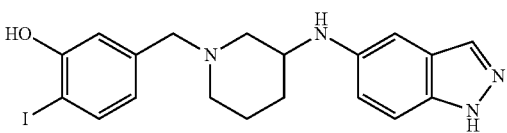 [SMILES: Oc1cc(CN2CCCC(Nc3ccc4[nH]ncc4c3)C2)ccc1I]<br>5-((3-(1H-indazol-5-ylamino)piperidin-1-yl)methyl)-2-iodophenol | 1c, 7, 8, 9, 10 |
| 1.069 | 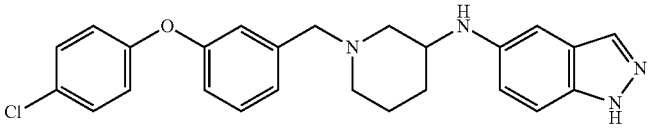 [SMILES: Clc1ccc(Oc2cccc(CN3CCCC(Nc4ccc5[nH]ncc5c4)C3)c2)cc1]<br>N-(1-(3-(4-chlorophenoxy)benzyl)piperidin-3-yl)-1H-indazol-5-amine | 1c, 7, 8, 9, 10 |

TABLE I-continued

Example Compounds.

| Compound | Structure | Embodiments |
|---|---|---|
| 1.070 | N-(1-(3-(3-(trifluoromethyl)phenoxy)benzyl)piperidin-3-yl)-1H-indazol-5-amine | 1c, 7, 8, 9, 10 |
| 1.071 | N-(1-(2,5-dibromobenzyl)piperidin-3-yl)-1H-indazol-5-amine | 1c, 7, 8, 9, 10 |
| 1.072 | (S)-N-(1-(3,4-difluorobenzyl)piperidin-3-yl)-1H-indazol-5-amine | 1c, 7, 8, 9, 10 |
| 1.073 | (R)-N-(1-(3,4-difluorobenzyl)piperidin-3-yl)-1H-indazol-5-amine | 1c, 7, 8, 9, 10 |
| 1.074 | (R)-N-(1-(4-(methylthio)benzyl)piperidin-3-yl)-1H-indazol-5-amine | 1c, 7, 8, 9, 10, 12b, 15c, 15e |
| 1.075 | (S)-N-(1-(4-(methylthio)benzyl)piperidin-3-yl)-1H-indazol-5-amine | 1c, 7, 8, 9, 10, 12b, 15c, 15e |
| 1.076 | (R)-N-(1-(4-ethynylbenzyl)piperidin-3-yl)-1H-indazol-5-amine | 1c, 7, 8, 9, 10, 11, 14c |

TABLE I-continued

Example Compounds.

| Compound | Structure | Embodiments |
|---|---|---|
| 1.077 | 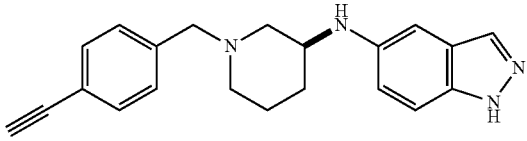 [SMILES: C#Cc1ccc(CN2CCC[C@H](Nc3ccc4[nH]ncc4c3)C2)cc1]<br>(S)-N-(1-(4-ethynylbenzyl)piperidin-3-yl)-1H-indazol-5-amine | 1, 7, 8, 9, 10, 11, 14c |
| 1.078 | 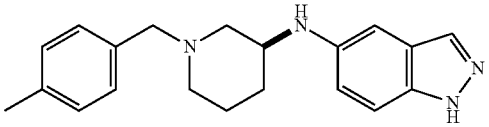 [SMILES: Cc1ccc(CN2CCC[C@H](Nc3ccc4[nH]ncc4c3)C2)cc1]<br>(S)-N-(1-(4-methylbenzyl)piperidin-3-yl)-1H-indazol-5-amine | 1c, 7, 8, 9, 10 |
| 1.079 | 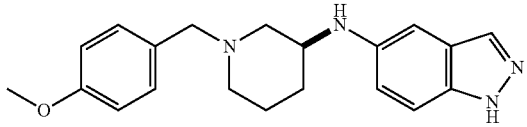 [SMILES: COc1ccc(CN2CCC[C@H](Nc3ccc4[nH]ncc4c3)C2)cc1]<br>(S)-N-(1-(4-methoxybenzyl)piperidin-3-yl)-1H-indazol-5-amine | 1c, 7, 8, 9, 10 |
| 1.080 | 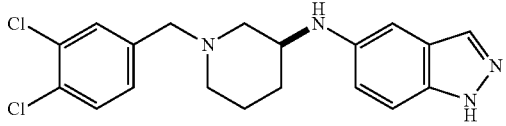 [SMILES: Clc1ccc(CN2CCC[C@H](Nc3ccc4[nH]ncc4c3)C2)cc1Cl]<br>(S)-N-(1-(3,4-dichlorobenzyl)piperidin-3-yl)-1H-indazol-5-amine | 1c, 7, 8, 9, 10 |
| 1.081 | 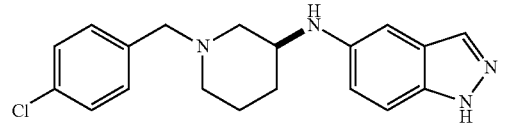 [SMILES: Clc1ccc(CN2CCC[C@H](Nc3ccc4[nH]ncc4c3)C2)cc1]<br>(S)-N-(1-(4-chlorobenzyl)piperidin-3-yl)-1H-indazol-5-amine | 1c, 7, 8, 9, 10 |
| 1.082 | 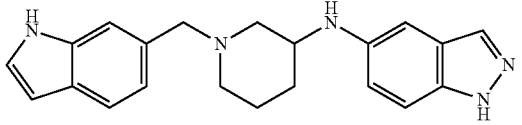 [SMILES: c1cc2ccc(CN3CCCC(Nc4ccc5[nH]ncc5c4)C3)cc2[nH]1]<br>N-(1-((1H-indol-6-yl)methyl)piperidin-3-yl)-1H-indazol-5-amine | 1c, 7, 8, 9, 10 |
| 1.083 | 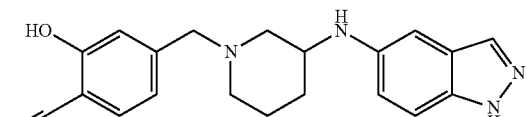<br>5-((3-(1H-indazol-5-ylamino)piperidin-1-yl)methyl)-2-ethynylphenol | 1c, 7, 8, 9, 10, 11, 14c |

TABLE I-continued

Example Compounds.

| Compound | Structure | Embodiments |
|---|---|---|
| 1.084 | 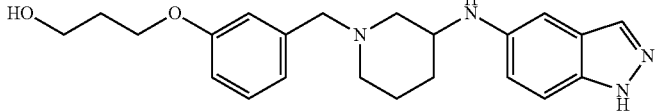<br>3-(3-((3-(1H-indazol-5-ylamino)piperidin-1-yl)methyl)phenoxy)propan-1-ol | 1c, 7, 8, 9, 10, 12a, 15c, 15d |
| 1.085 | 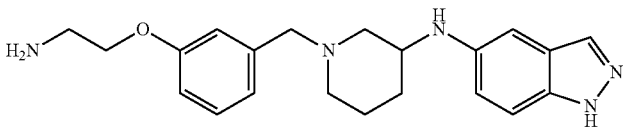 [SMILES: NCCOc1cccc(CN2CCCC(Nc3ccc4[nH]ncc4c3)C2)c1]<br>N-(1-(3-(2-aminoethoxy)benzyl)piperidin-3-yl)-1H-indazol-5-amine | 1c, 7, 8, 9, 10, 12a, 15c, 15d |
| 1.086 | 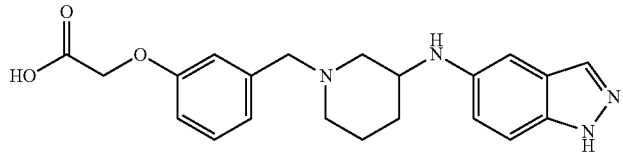 [SMILES: O=C(O)COc1cccc(CN2CCCC(Nc3ccc4[nH]ncc4c3)C2)c1]<br>2-(3-((3-(1H-indazol-5-ylamino)piperidin-1-yl)methyl)phenoxy)acetic acid | 1c, 7, 8, 9, 10, 12a, 15c, 15d |
| 1.087 | 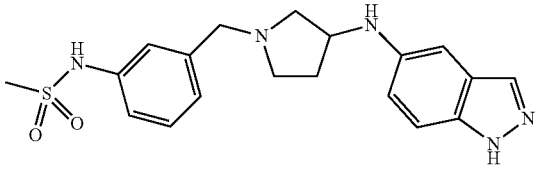<br>N-(3-((3-(1H-indazol-5-ylamino)pyrrolidin-1-yl)methyl)phenyl)methanesulfonamide | 1c, 7, 8, 9, 10, 12a, 15c, 15d |
| 1.088 | 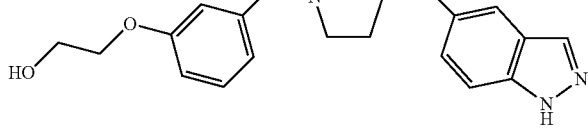<br>2-(3-((3-(1H-indazol-5-ylamino)pyrrolidin-1-yl)methyl)phenoxy)ethanol | 1c, 7, 8, 9, 10, 12a, 15c, 15d |
| 1.089 | 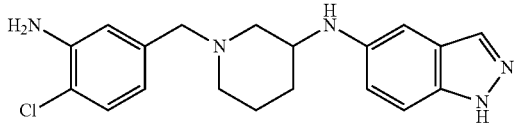 [SMILES: Nc1cc(CN2CCCC(Nc3ccc4[nH]ncc4c3)C2)ccc1Cl]<br>N-(1-(3-amino-4-chlorobenzyl)piperidin-3-yl)-1H-indazol-5-amine | 1c, 7, 8, 9, 10 |
| 1.090 | 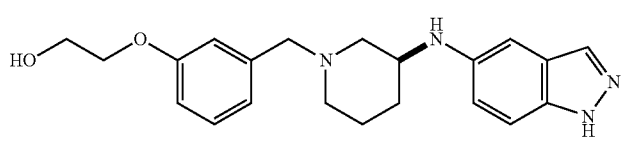 [SMILES: OCCOc1cccc(CN2CCC[C@H](Nc3ccc4[nH]ncc4c3)C2)c1]<br>(S)-2-(3-((3-(1H-indazol-5-ylamino)piperidin-1-yl)methyl)phenoxy)ethanol | 1c, 7, 8, 9, 10, 12a, 15c, 15d |

TABLE I-continued

Example Compounds.

| Compound | Structure | Embodiments |
|---|---|---|
| 1.091 | (S)-N-(3-((3-(1H-indazol-5-ylamino)piperidin-1-yl)methyl)phenyl)methanesulfonamide | 1c, 7, 8, 9, 10, 12a, 15c, 15d |
| 1.092 | (R)-2-(3-((3-(1H-indazol-5-ylamino)piperidin-1-yl)methyl)phenoxy)ethanol | 1c, 7, 8, 9, 10, 12a, 15c, 15d |
| 1.093 | (R)-N-(3-((3-(1H-indazol-5-ylamino)piperidin-1-yl)methyl)phenyl)methanesulfonamide | 1c, 7, 8, 9, 10, 12a, 15c, 15d |
| 1.094 | (S)-2-(3-((3-(1H-indazol-5-ylamino)pyrrolidin-1-yl)methyl)phenoxy)ethanol | 1c, 7, 8, 9, 10, 12a, 15c, 15d |
| 1.095 | (S)-N-(3-((3-(1H-indazol-5-ylamino)pyrrolidin-1-yl)methyl)phenyl)methanesulfonamide | 1c, 7, 8, 9, 10, 12a, 15c, 15d |
| 1.096 | (R)-2-(3-((3-(1H-indazol-5-ylamino)pyrrolidin-1-yl)methyl)phenoxy)ethanol | 1c, 7, 8, 9, 10, 12a, 15c, 15d |

TABLE I-continued

Example Compounds.

| Compound | Structure | Embodiments |
|---|---|---|
| 1.097 | (R)-N-(3-((3-(1H-indazol-5-ylamino)pyrrolidin-1-yl)methyl)phenyl)methanesulfonamide | 1c, 7, 8, 9, 10, 12a, 15c, 15d |
| 1.098 | 2-(3-((3-(1H-indazol-5-ylamino)piperidin-1-yl)methyl)phenoxy)acetamide | 1c, 7, 8, 9, 10, 12a, 15c, 15d |
| 1.099 | 2-(6-((3-(1H-indazol-5-ylamino)piperidin-1-yl)methyl)-1H-indol-1-yl)acetamide | 1c, 7, 8, 9, 10, 13, 16c |
| 1.100 | N-(1-((1H-indol-5-yl)methyl)piperidin-3-yl)-1H-indazol-5-amine | 1c, 7, 8, 9, 10 |
| 1.101 | 2-(6-((3-(1H-indazol-5-ylamino)piperidin-1-yl)methyl)-1H-indol-1-yl)ethanol | 1c, 7, 8, 9, 10, 13, 16c |
| 1.102 | N-(5-((3-(1H-indazol-5-ylamino)piperidin-1-yl)methyl)-2-chlorophenyl)methanesulfonamide | 1c, 7, 8, 9, 10, 12a, 15c, 15d |

TABLE I-continued

Example Compounds.

| Compound | Structure | Embodiments |
|---|---|---|
| 1.103 | 2-(6-((3-(1H-indazol-5-ylamino)piperidin-1-yl)methyl)-1H-indol-1-yl)acetic acid | 1c, 7, 8, 9, 10, 13, 16c |
| 1.104 | 2-(6-((3-(1H-indazol-5-ylamino)piperidin-1-yl)methyl)indolin-1-yl)ethanol | 1c, 7, 8, 9, 10, 13, 16c |
| 1.105 | 2-(5-((3-(1H-indazol-5-ylamino)piperidin-1-yl)methyl)-1H-indol-1-yl)acetamide | 1c, 7, 8, 9, 10, 13, 16c |
| 1.106 | (R)-2-(6-((3-(1H-indazol-5-ylamino)piperidin-1-yl)methyl)-1H-indol-1-yl)acetamide | 1c, 7, 8, 9, 10, 13, 16c |
| 1.107 | (S)-2-(6-((3-(1H-indazol-5-ylamino)piperidin-1-yl)methyl)-1H-indol-1-yl)acetamide | 1c, 7, 8, 9, 10, 13, 16c |

TABLE I-continued

Example Compounds.

| Compound | Structure | Embodiments |
|---|---|---|
| 1.108 | 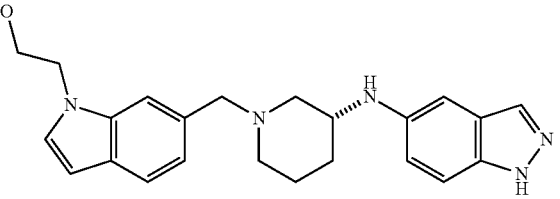<br>(R)-2-(6-((3-(1H-indazol-5-ylamino)piperidin-1-yl)methyl)-1H-indol-1-yl)ethanol | 1c, 7, 8, 9, 10, 13, 16c |
| 1.109 | 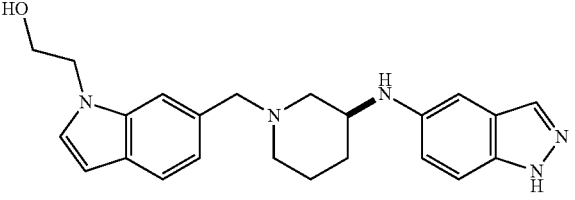 [SMILES: OCCn1ccc2ccc(CN3CCC[C@H](Nc4ccc5[nH]ncc5c4)C3)cc21]<br>(S)-2-(6-((3-(1H-indazol-5-ylamino)piperidin-1-yl)methyl)-1H-indol-1-yl)ethanol | 1c, 7, 8, 9, 10, 13, 16c |
| 1.110 | 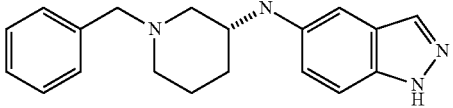<br>(R)-N-(1-benzylpiperidin-3-yl)-1H-indazol-5-amine | 1c, 7, 8, 9, 10 |
| 1.111 | 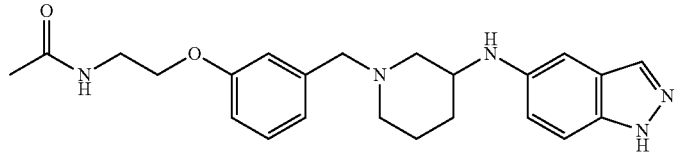 [SMILES: CC(=O)NCCOc1cccc(CN2CCCC(Nc3ccc4[nH]ncc4c3)C2)c1]<br>N-(2-(3-((3-(1H-indazol-5-ylamino)piperidin-1-yl)methyl)phenoxy)ethyl)acetamide | 1c, 7, 8, 9, 10, 12a, 15c, 15d |
| 1.112 | 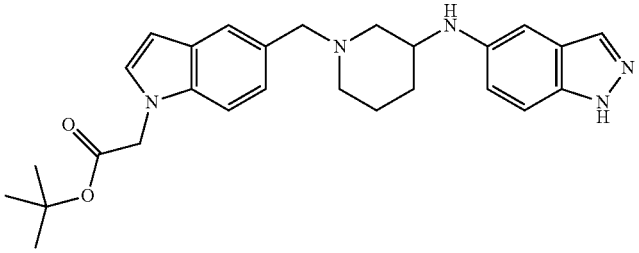 [SMILES: CC(C)(C)OC(=O)Cn1ccc2cc(CN3CCCC(Nc4ccc5[nH]ncc5c4)C3)ccc21]<br>tert-butyl 2-(5-((3-(1H-indazol-5-ylamino)piperidin-1-yl)methyl)-1H-indol-1-yl)acetate | 1c, 7, 8, 9, 10, 13, 16c |
| 1.113 | 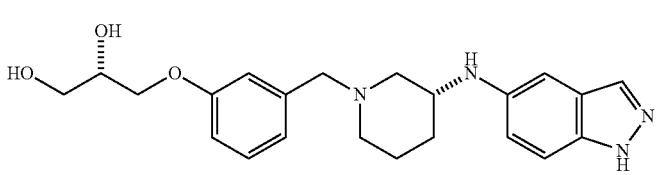 [SMILES: OC[C@H](O)COc1cccc(CN2CCC[C@@H](Nc3ccc4[nH]ncc4c3)C2)c1]<br>(S)-3-(3-(((R)-3-(1H-indazol-5-ylamino)piperidin-1-yl)methyl)phenoxy)propane-1,2-diol | 1c, 7, 8, 9, 10, 12a, 15c, 15d |

TABLE I-continued

Example Compounds.

| Compound | Structure | Embodiments |
|---|---|---|
| 1.114 | 2-(5-((3-(1H-indazol-5-ylamino)piperidin-1-yl)methyl)-1H-indol-1-yl)ethanol | 1c, 7, 8, 9, 10, 13, 16c |
| 1.115 | (R)-3-(3-(((R)-3-(1H-indazol-5-ylamino)piperidin-1-yl)methyl)phenoxy)propane-1,2-diol | 1c, 7, 8, 9, 10, 12a, 15c, 15d |
| 1.116 | (R)-1-(3-(((R)-3-(1H-indazol-5-ylamino)piperidin-1-yl)methyl)phenoxy)propan-2-ol | 1c, 7, 8, 9, 10, 12a, 15c, 15d |
| 1.117 | (R)-3-(3-(((S)-3-(1H-indazol-5-ylamino)piperidin-1-yl)methyl)phenoxy)propane-1,2-diol | 1c, 7, 8, 9, 10, 12a, 15c, 15d |
| 1.118 | (R)-1-(3-(((S)-3-(1H-indazol-5-ylamino)piperidin-1-yl)methyl)phenoxy)propan-2-ol | 1c, 7, 8, 9, 10, 12a, 15c, 15d |
| 1.119 | 2-(5-((3-(1H-indazol-5-ylamino)piperidin-1-yl)methyl)-1H-indol-1-yl)acetic acid | 1c, 7, 8, 9, 10, 13, 16c |

TABLE I-continued

Example Compounds.

| Compound | Structure | Embodiments |
|---|---|---|
| 1.120 | N-(3-((3-(1H-indazol-5-ylamino)piperidin-1-yl)methyl)phenyl)ethanesulfonamide | 1c, 7, 8, 9, 10, 12a, 15c, 15d |
| 1.121 | N-(3-((3-(1H-indazol-5-ylamino)piperidin-1-yl)methyl)phenyl)-N-methylmethanesulfonamide | 1c, 7, 8, 9, 10, 12a, 15c, 15d |
| 1.122 | N-(3-((3-(1H-indazol-5-ylamino)piperidin-1-yl)methyl)benzyl)acetamide | 1c, 7, 8, 9, 10, 13, 16c |
| 1.123 | (R)-N-(3-((3-(1H-indazol-5-ylamino)piperidin-1-yl)methyl)phenyl)ethanesulfonamide | 1c, 7, 8, 9, 10, 12a, 15c, 15d |
| 1.124 | (S)-N-(3-((3-(1H-indazol-5-ylamino)piperidin-1-yl)methyl)phenyl)ethanesulfonamide | 1c, 7, 8, 9, 10, 12a, 15c, 15d |
| 1.125 | (R)-2-(3-((3-(1H-indazol-5-ylamino)piperidin-1-yl)methyl)phenoxy)acetic acid | 1c, 7, 8, 9, 10, 12a, 15c, 15d |
| 1.126 | (R)-2-(3-((3-(1H-indazol-5-ylamino)piperidin-1-yl)methyl)phenoxy)-N-(pyridin-3-yl)acetamide | 1c, 7, 8, 9, 10, 12a, 15c, 15d |

TABLE I-continued

Example Compounds.

| Compound | Structure | Embodiments |
|---|---|---|
| 1.127 | 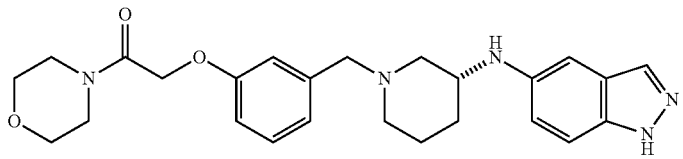 [SMILES: O=C(COc1cccc(CN2CCC[C@@H](Nc3ccc4[nH]ncc4c3)C2)c1)N1CCOCC1]
(R)-2-(3-((3-(1H-indazol-5-ylamino)piperidin-1-yl)methyl)phenoxy)-1-morpholinoethanone | 1c, 7, 8, 9, 10, 12a, 15c, 15d |
| 1.128 | 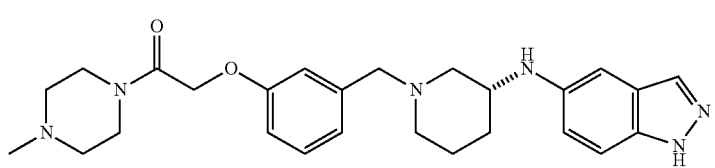 [SMILES: CN1CCN(C(=O)COc2cccc(CN3CCC[C@@H](Nc4ccc5[nH]ncc5c4)C3)c2)CC1]
(R)-2-(3-((3-(1H-indazol-5-ylamino)piperidin-1-yl)methyl)phenoxy)-1-(4-methylpiperazin-1-yl)ethanone | 1c, 7, 8, 9, 10, 12a, 15c, 15d |
| 1.129 | 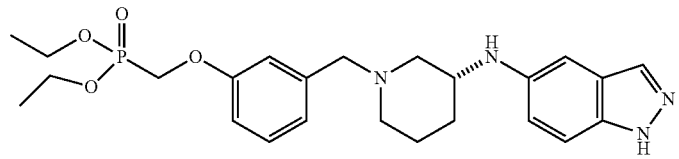 [SMILES: CCOP(=O)(COc1cccc(CN2CCC[C@@H](Nc3ccc4[nH]ncc4c3)C2)c1)OCC]
(R)-diethyl (3-((3-(1H-indazol-5-ylamino)piperidin-1-yl)methyl)phenoxy)methylphosphonate | 1c, 7, 8, 9, 10, 12a, 15c, 15d |
| 1.130 | 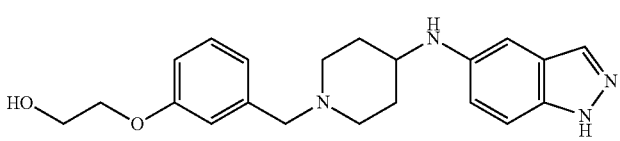 [SMILES: OCCOc1cccc(CN2CCC(Nc3ccc4[nH]ncc4c3)CC2)c1]
2-(3-((4-(1H-indazol-5-ylamino)piperidin-1-yl)methyl)phenoxy)ethanol | 1c, 7, 8, 9, 10, 12a, 15c, 15d |
| 1.131 | 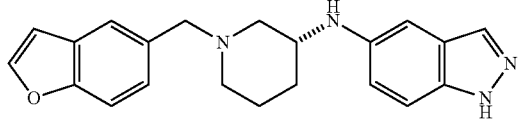 [SMILES: c1cc2cc(CN3CCC[C@@H](Nc4ccc5[nH]ncc5c4)C3)ccc2o1]
(R)-N-(1-(benzofuran-5-ylmethyl)piperidin-3-yl)-1H-indazol-5-amine | 1c, 7, 8, 9, 10 |
| 1.132 | 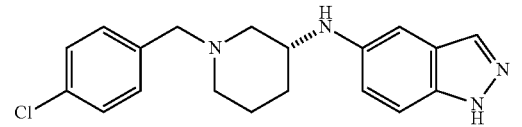 [SMILES: Clc1ccc(CN2CCC[C@@H](Nc3ccc4[nH]ncc4c3)C2)cc1]
(R)-N-(1-(4-chlorobenzyl)piperidin-3-yl)-1H-indazol-5-amine | 1c, 7, 8, 9, 10 |
| 1.133 | 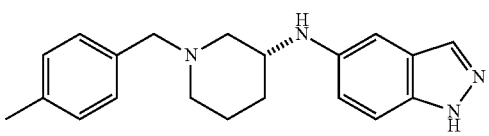 [SMILES: Cc1ccc(CN2CCC[C@@H](Nc3ccc4[nH]ncc4c3)C2)cc1]
(R)-N-(1-(4-methylbenzyl)piperidin-3-yl)-1H-indazol-5-amine | 1c, 7, 8, 9, 10 |

TABLE I-continued

Example Compounds.

| Compound | Structure | Embodiments |
|---|---|---|
| 1.134 | 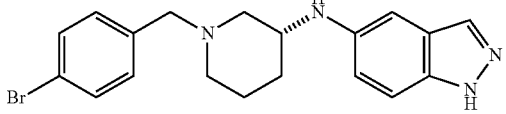 (R)-N-(1-(4-bromobenzyl)piperidin-3-yl)-1H-indazol-5-amine | 1c, 7, 8, 9, 10 |
| 1.136 | 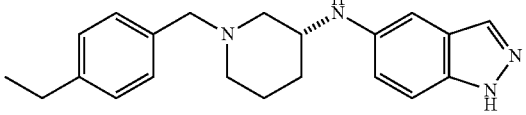 (R)-N-(1-(4-ethylbenzyl)piperidin-3-yl)-1H-indazol-5-amine | 1c, 7, 8, 9, 10 |
| 1.137 | 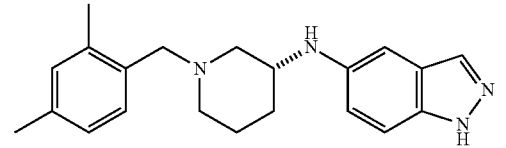 [SMILES: Cc1ccc(CN2CCC[C@@H](Nc3ccc4[nH]ncc4c3)C2)c(C)c1] (R)-N-(1-(2,4-dimethylbenzyl)pipendin-3-yl)-1H-indazol-5-amine | 1c, 7, 8, 9, 10 |
| 1.138 | 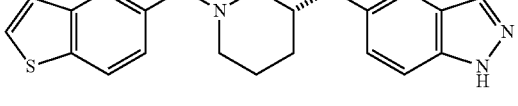 (R)-N-(1-(benzo[b]thiophen-5-ylmethyl)piperidin-3-yl)-1H-indazol-5-amine | 1c, 7, 8, 9, 10 |
| 2.001 | 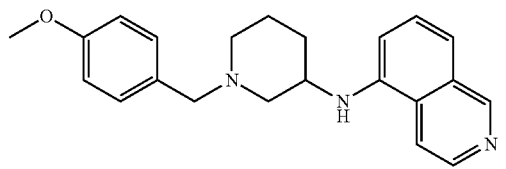 [SMILES: COc1ccc(CN2CCCC(Nc3cccc4cnccc34)C2)cc1] N-(1-(4-methoxybenzyl)piperidin-3-yl)isoquinolin-5-amine | 2c, 7, 8, 9, 10 |
| 2.002 | 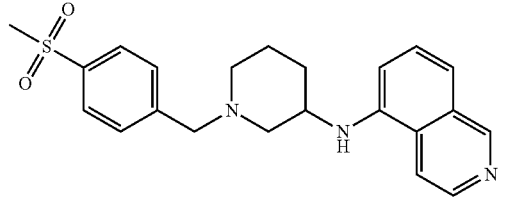 [SMILES: CS(=O)(=O)c1ccc(CN2CCCC(Nc3cccc4cnccc34)C2)cc1] N-(1-(4-(methylsulfonyl)benzyl)piperidin-3-yl)isoquinolin-5-amine | 2c, 7, 8, 9, 10, 12, 15c |
| 2.003 | 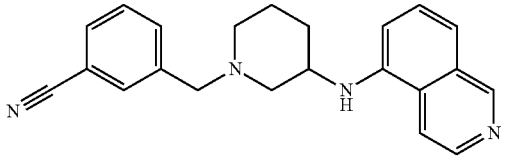 [SMILES: N#Cc1cccc(CN2CCCC(Nc3cccc4cnccc34)C2)c1] 3-((3-(isoquinolin-5-ylamino)piperidin-1-yl)methyl)benzonitrile | 2c, 7, 8, 9, 10, 12, 15c |

TABLE I-continued

Example Compounds.

| Compound | Structure | Embodiments |
|---|---|---|
| 2.004 | N-(4-((3-(isoquinolin-5-ylamino)piperidin-1-yl)methyl)phenyl)acetamide | 2c, 7, 8, 9, 10, 12a, 15c, 15d |
| 2.005 | N-(1-(4-(methylsulfonyl)benzyl)pyrrolidin-3-yl)isoquinolin-5-amine | 2c, 7, 8, 9, 10, 12, 15c |
| 2.006 | N-(1-benzylpyrrolidin-3-yl)isoquinolin-5-amine | 2c, 7, 8, 9, 10 |
| 2.007 | 3-((3-(isoquinolin-5-ylamino)pyrrolidin-1-yl)methyl)benzonitrile | 2c, 7, 8, 9, 10, 12, 15c |
| 2.008 | N-(4-((3-(isoquinolin-5-ylamino)pyrrolidin-1-yl)methyl)phenyl)acetamide | 2c, 7, 8, 9, 10, 12a, 15c, 15d |
| 2.009 | N-(1-(4-(methylthio)benzyl)piperidin-3-yl)isoquinolin-5-amine | 2c, 7, 8, 9, 10, 12b, 15c, 15e |

TABLE I-continued

Example Compounds.

| Compound | Structure | Embodiments |
|---|---|---|
| 2.010 | N-(1-(4-cyclopropylbenzyl)piperidin-3-yl)isoquinolin-5-amine | 2c, 7, 8, 9, 10, 11, 14c |
| 2.011 | N-(1-(3-cyclopropylbenzyl)piperidin-3-yl)isoquinolin-5-amine | 2c, 7, 8, 9, 10, 11, 14c |
| 2.012 | N-(1-(4-(cyclopropylthio)benzyl)piperidin-3-yl)isoquinolin-5-amine | 2c, 7, 8, 9, 10, 12b, 15c, 15e |
| 2.013 | N-(1-benzylazepan-4-yl)isoquinolin-5-amine | 2c, 7, 8, 9, 10 |
| 2.014 | N-(1-(3,4-dichlorobenzyl)piperidin-3-yl)isoquinolin-5-amine | 2c, 7, 8, 9, 10 |
| 2.015 | N-(1-(3-(trifluoromethyl)benzyl)piperidin-3-yl)isoquinolin-5-amine | 2c, 7, 8, 9, 10 |

TABLE I-continued

Example Compounds.

| Compound | Structure | Embodiments |
|---|---|---|
| 2.016 | N-(1-(3,4-dichlorobenzyl)pyrrolidin-3-yl)isoquinolin-5-amine | 2c, 7, 8, 9, 10 |
| 2.017 | N-(1-(4-methoxybenzyl)pyrrolidin-3-yl)isoquinolin-5-amine | 2c, 7, 8, 9, 10 |
| 2.018 | N-(1-(3-(trifluoromethyl)benzyl)pyrrolidin-3-yl)isoquinolin-5-amine | 2c, 7, 8, 9, 10 |
| 2.019 | (S)-N-(1-(4-cyclopropylbenzyl)pyrrolidin-3-yl)isoquinolin-5-amine | 2c, 7, 8, 9, 10, 11, 14c |
| 2.020 | (R)-N-(1-(3-cyclopropylbenzyl)pyrrolidin-3-yl)isoquinolin-5-amine | 2c, 7, 8, 9, 10, 11, 14c |
| 2.021 | (R)-N-(1-(4-(cyclopropylthio)benzyl)pyrrolidin-3-yl)isoquinolin-5-amine | 2c, 7, 8, 9, 10, 12b, 15c, 15e |

TABLE I-continued

Example Compounds.

| Compound | Structure | Embodiments |
|---|---|---|
| 2.022 | 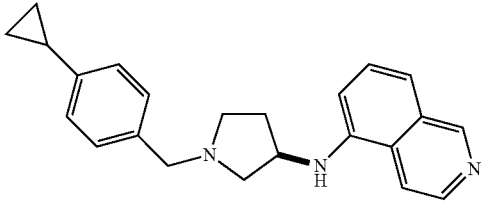 [SMILES: c1cc(N[C@@H]2CCN(Cc3ccc(C4CC4)cc3)C2)c2ccncc2c1]<br>(R)-N-(1-(4-cyclopropylbenzyl)pyrrolidin-3-yl)isoquinolin-5-amine | 2c, 7, 8, 9, 10, 11, 14c |
| 2.023 | 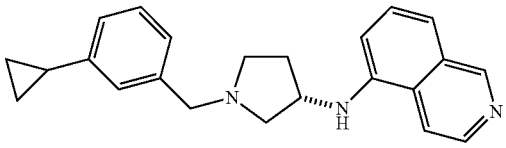 [SMILES: c1cc(CN2CC[C@H](Nc3cccc4cnccc34)C2)cc(C2CC2)c1]<br>(S)-N-(1-(3-cyclopropylbenzyl)pyrrolidin-3-yl)isoquinolin-5-amine | 2c, 7, 8, 9, 10, 11, 14c |
| 2.024 | 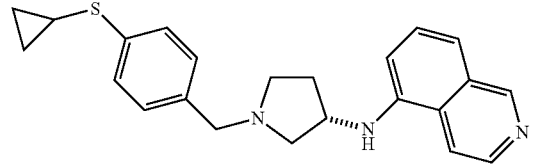 [SMILES: c1cc(N[C@H]2CCN(Cc3ccc(SC4CC4)cc3)C2)c2ccncc2c1]<br>(S)-N-(1-(4-(cyclopropylthio)benzyl)pyrrolidin-3-yl)isoquinolin-5-amine | 2c, 7, 8, 9, 10, 12b, 15c, 15e |
| 2.025 | 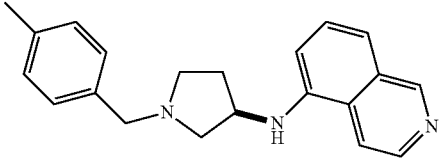 [SMILES: Cc1ccc(CN2CC[C@@H](Nc3cccc4cnccc34)C2)cc1]<br>(R)-N-(1-(4-methylbenzyl)pyrrolidin-3-yl)isoquinolin-5-amine | 2c, 7, 8, 9, 10 |
| 2.026 | 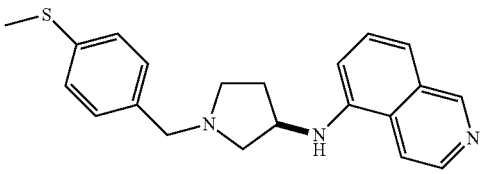 [SMILES: CSc1ccc(CN2CC[C@@H](Nc3cccc4cnccc34)C2)cc1]<br>(R)-N-(1-(4-(methylthio)benzyl)pyrrolidin-3-yl)isoquinolin-5-amine | 2c, 7, 8, 9, 10, 12b, 15c, 15e |
| 2.027 | 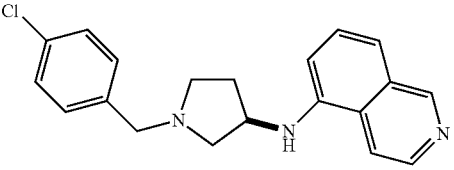 [SMILES: Clc1ccc(CN2CC[C@@H](Nc3cccc4cnccc34)C2)cc1]<br>(R)-N-(1-(4-chlorobenzyl)pyrrolidin-3-yl)isoquinolin-5-amine | 2c, 7, 8, 9, 10 |

TABLE I-continued

Example Compounds.

| Compound | Structure | Embodiments |
|---|---|---|
| 2.028 | (S)-N-(1-(4-methylbenzyl)pyrrolidin-3-yl)isoquinolin-5-amine | 2c, 7, 8, 9, 10 |
| 2.029 | (S)-N-(1-(4-(methylthio)benzyl)pyrrolidin-3-yl)isoquinolin-5-amine | 2c, 7, 8, 9, 10, 12b, 15c, 15e |
| 2.030 | (S)-N-(1-(4-chlorobenzyl)pyrrolidin-3-yl)isoquinolin-5-amine | 2c, 7, 8, 9, 10 |
| 2.031 | (R)-N-(1-(4-ethynylbenzyl)pyrrolidin-3-yl)isoquinolin-5-amine | 2c, 7, 8, 9, 10, 11, 14c |
| 2.032 | (S)-2-(3-((3-(isoquinolin-5-ylamino)pyrrolidin-1-yl)methyl)phenoxy)ethanol | 2c, 7, 8, 9, 10, 12a, 15c, 15d |
| 2.033 | (R)-N-(3-((3-(isoquinolin-5-ylamino)piperidin-1-yl)methyl)phenyl)methanesulfonamide | 2c, 7, 8, 9, 10, 12a, 15c, 15d |

TABLE I-continued

Example Compounds.

| Compound | Structure | Embodiments |
|---|---|---|
| 2.034 | (R)-2-(3-((3-(isoquinolin-5-ylamino)piperidin-1-yl)methyl)phenoxy)ethanol | 2c, 7, 8, 9, 10, 12a, 15c, 15d |
| 2.035 | (S)-N-(3-((3-(isoquinolin-5-ylamino)pyrrolidin-1-yl)methyl)phenyl)methanesulfonamide | 2c, 7, 8, 9, 10, 12a, 15c, 15d |
| 2.036 | (S)-2-(3-((3-(isoquinolin-5-ylamino)piperidin-1-yl)methyl)phenoxy)ethanol | 2c, 7, 8, 9, 10, 12a, 15c, 15d |
| 2.037 | (S)-N-(3-((3-(isoquinolin-5-ylamino)piperidin-1-yl)methyl)phenyl)methanesulfonamide | 2c, 7, 8, 9, 10, 12a, 15c, 15d |
| 2.038 | (R)-N-(3-((3-(isoquinolin-5-ylamino)pyrrolidin-1-yl)methyl)phenyl)methanesulfonamide | 2c, 7, 8, 9, 10, 12a, 15c, 15d |
| 2.039 | (R)-2-(3-((3-(isoquinolin-5-ylamino)pyrrolidin-1-yl)methyl)phenoxy)ethanol | 2c, 7, 8, 9, 10, 12a, 15c, 15d |

TABLE I-continued

Example Compounds.

| Compound | Structure | Embodiments |
|---|---|---|
| 2.040 | (R)-2-(3-((3-(isoquinolin-5-ylamino)pyrrolidin-1-yl)methyl)phenoxy)acetamide | 2c, 7, 8, 9, 10, 12a, 15c, 15d |
| 2.041 | (R)-N-(3-((3-(isoquinolin-5-ylamino)pyrrolidin-1-yl)methyl)phenyl)ethanesulfonamide | 2c, 7, 8, 9, 10, 12a, 15c, 15d |
| 2.042 | 2-(3-((3-(isoquinolin-5-ylamino)pyrrolidin-1-yl)methyl)phenoxy)ethanol | 2c, 7, 8, 9, 10, 12a, 15c, 15d |
| 2.043 | (R)-2-(3-((3-(isoquinolin-5-ylamino)pyrrolidin-1-yl)methyl)phenoxy)-1-morpholinoethanone | 2c, 7, 8, 9, 10, 12a, 15c, 15d |
| 2.044 | (R)-2-(3-((3-(isoquinolin-5-ylamino)pyrrolidin-1-yl)methyl)phenoxy)acetic acid | 2c, 7, 8, 9, 10, 12a, 15c, 15d |
| 3.001 | N-(1-benzylpiperidin-3-yl)pyridin-4-amine | 3c, 7, 8, 9, 10 |
| 3.002 | N-(1-benzylpyrrolidin-3-yl)pyridin-4-amine | 3c, 7, 8, 9, 10 |

TABLE I-continued

Example Compounds.

| Compound | Structure | Embodiments |
|---|---|---|
| 4.001 | N-(1-benzylpiperidin-3-yl)-1H-pyrrolo[2,3-b]pyridin-4-amine | 4c, 7, 8, 9, 10 |
| 4.002 | N-(1-benzylpyrrolidin-3-yl)-1H-pyrrolo[2,3-b]pyridin-4-amine | 4c, 7, 8, 9, 10 |
| 5.001 | 4-(4-(1-benzylpiperidin-3-ylamino)phenyl)-1,2,5-oxadiazol-3-amine | 5a, 7, 8, 9, 10 |
| 5.002 | 4-(4-(1-benzylpyrrolidin-3-ylamino)phenyl)-1,2,5-oxadiazol-3-amine | 5a, 7, 8, 9, 10 |

Preparation of Compounds of Formula I and Formula II

The present invention is additionally directed to procedures for preparing compounds of Formula I and Formula II. General approaches for preparations of the compounds of the Formulae are described in Scheme 1 and Scheme 2. Those having skill in the art will recognize that the starting materials can be varied and additional steps can be employed to produce compounds encompassed by the present invention. In some cases, protection of certain reactive functionalities may be necessary to achieve some of the above transformations. In general, the need for such protecting groups as well as the conditions necessary to attach and remove such groups will be apparent to those skilled in the art of organic synthesis.

Those skilled in the art will recognize various synthetic methodologies that can be employed to prepare non-toxic pharmaceutically acceptable prodrugs, for example acylated prodrugs, of the compounds of this invention.

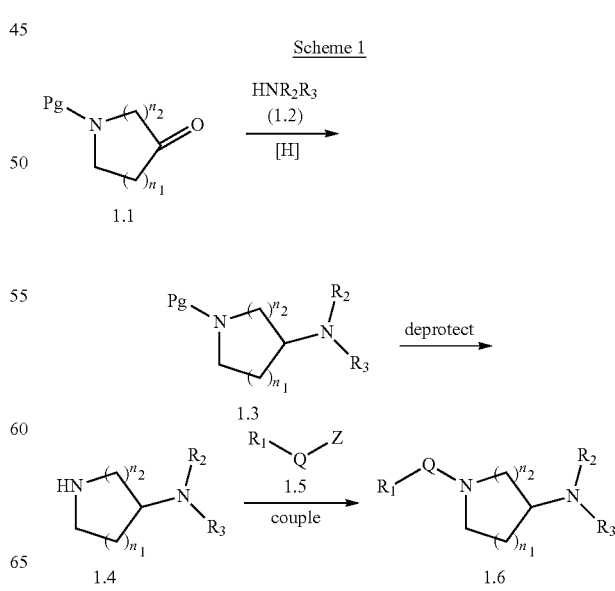

The preparation of materials described by the Formulae is shown in Scheme 1. In this Scheme, a protected heterocyclic ketone 1.1, readily available using preparations well known in the literature, is treated with an amine 1.2 under reductive amination conditions, typically using a borohydride reducing agent such as sodium triacetoxyborohydride. The resulting protected diamine 1.3 is deprotected using conditions appropriate to the choice of protecting group, for example, acid conditions for a BOC protecting group or reductive conditions for a CBZ group. The deprotected product 1.4 is then coupled with a coupling partner 1.5 with functionality Q-Z that is suitable for introducing the substituent $R_1$-Q. Typical example coupling reactions with 1.5 include reductive amination with an aldehyde, alkylation with an alkyl halide, and acylation with an acyl halide or sulfonyl halide. This coupling reaction provides compound 1.6, an example of the substances described by the Formulae.

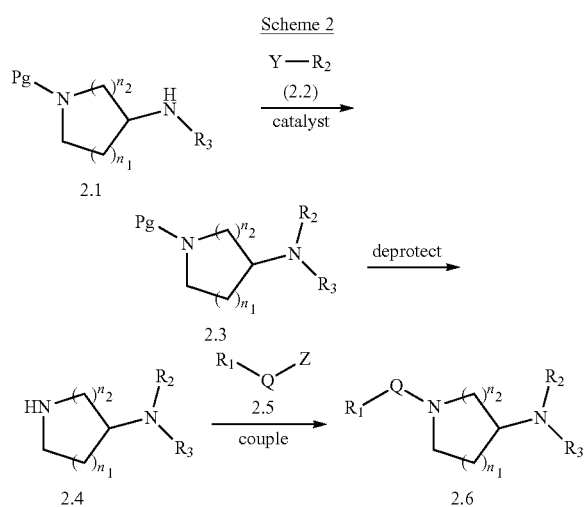

Scheme 2

An additional preparation of materials described by Formula I and Formula II is shown in Scheme 2. In this Scheme, a protected diamine 2.1, readily available using preparations well known in the literature, is allowed to react with a suitably activated form of the substituent $R_2$, 2.2, optionally in the presence of a catalyst. Example activating groups Y include halides and triflates, and palladium catalysts are typically used. This coupling reaction produces the protected diamine product 2.3, which is analogous to protected diamine 1.3 in Scheme 1, and which is elaborated in the same sequence of transformations to yield 2.6, an example of the substances described by the Formulae. As protected diamines 2.1 are readily available in optically active form using methods well known in the literature, the methods of Scheme 2 provide convenient methods to prepare the compounds of the Formulae in optically active form. It will be seen that modifications of the above two synthetic schemes using well-known procedures will allow the preparation of other members in the scope of the Formulae.

Appropriate protection of interfering function groups can be important for obtaining satisfactory reaction of 2.1 and 2.2 to give 2.3. In particular, when $R_2$ is indazolyl, protection of any unsubstituted indazole nitrogen is critical to the success of the reaction. Preferred protecting groups in this situation are p-methoxybenzyl (PMB) and 2-tetrahydropyranyl (THP), with THP being most preferred. Use of the THP protecting group provides high yields in the protection, coupling, and deprotection steps, and allows the protecting group to be removed without the need for scavenger reagents, which are otherwise needed for clean deprotection.

Pharmaceutical Composition and Use

The present invention also provides pharmaceutical compositions. The pharmaceutical compositions are pharmaceutically acceptable formulations comprising a pharmaceutically acceptable carrier and one or more compounds of Formula I and/or Formula II, pharmaceutically acceptable salts, solvates, and/or hydrates thereof. The pharmaceutically acceptable carrier can be selected by those skilled in the art using conventional criteria. Pharmaceutically acceptable carriers include, but are not limited to, aqueous- and non-aqueous based solutions, suspensions, emulsions, microemulsions, micellar solutions, gels, and ointments. The pharmaceutically active carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, hydronium, phosphate, citrate, acetate, borate, and tromethamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and polysaccharides such as dextrans, and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

In one embodiment of the invention, the compositions are formulated as topical ophthalmic preparations, with a pH of about 3-9, preferably 4 to 8. The compounds of the invention are generally contained in these formulations in an amount of at least 0.001% by weight, for example, 0.001% to 5% by weight, preferably about 0.003% to about 2% by weight, with an amount of about 0.02% to about 1% by weight being most preferred. For topical administration, one to two drops of these formulations are delivered to the surface of the eye one to four times per day according to the routine discretion of a skilled clinician.

In one embodiment of the invention, the compositions are formulated as aqueous pharmaceutical formulations comprising at least one compound of Formula I and/or Formula II in an amount of 0.001-2% w/v, and a tonicity agent to maintain a tonicity between 200-400 mOsm/kG, wherein the pH of the formulation is 3-9.

In yet another embodiment, the aqueous pharmaceutical formulation comprises at least one compound of Formula I and/or Formula II in an amount of 0.001-2% w/v, one or more complexing and/or solubilizing agents, 0.01-0.5% preservative, 0.01-1% chelating agent, and a tonicity agent to maintain a tonicity between 200-400 mOsm/kG, wherein the pH of the formulation is 4-8. The preferred amount of the compound is 0.01-1% w/v.

The delivery of such ophthalmic preparations may be done using a single unit dose vial wherein the inclusion of a preservative may be precluded. Alternatively, the ophthalmic preparation may be contained in an ophthalmic dropper container intended for multi-use. In such an instance, the multi-use product container may or may not contain a preservative, especially in the event the formulation is self-preserving. Furthermore, the dropper container is designed to deliver a certain fixed volume of product preparation in each drop. The typical drop volume of such an ophthalmic preparation will range from 20-60 microliters, preferably 25-55 microliters, more preferably 30-50 microliters, with 35-50 microliters being most preferred.

Glaucoma is an ophthalmic disease that leads to irreversible visual impairment. Primary open-angle glaucoma is characterized by abnormally high resistance to fluid (aqueous humor) drainage from the eye. Cellular contractility and changes in cell-cell and cell-trabeculae adhesion in the trabecular meshwork are major determinants of the resistance to flow. The compounds of the present invention cause a transient, pharmacological perturbation of both cell contractility and cell adhesions, mainly via disruption of the actomyosin-associated cytoskeletal structures and/or the modulation of their interactions with the membrane. Altering the contractility of trabecular meshwork cells leads to drainage-surface expansion. Loss of cell-cell, cell-trabeculae adhesion may influence paracellular fluid flow across Schlemm's canal or alter the fluid flow pathway through the juxtacanalicular tissue of the trabecular meshwork. Both mechanisms likely reduce the resistance of the trabecular meshwork to fluid flow and thereby reduce intraocular pressure in a therapeutically useful manner.

The compounds of the present invention are useful for modulation of wound healing after trabeculectomy. The compounds in general are less toxic to both corneal epithelial and endothelial cells than the antimetabolites such as 5-fluorouracil or mitomycin C. The compounds inhibit actomyosin-driven contractility, leading to deterioration of the actin microfilament system and perturbation of its membrane anchorage, which weakens the cell-extracellular matrix adhesions. These properties inhibit wound healing and thereby reduce bleb failure following the surgery.

A frequent complication of extracapsular cataract extraction and intraocular lens (IOL) implantation is posterior capsule opacification (PCO); a type of secondary cataract caused by residual epithelial cells following lens removal. Perturbation of the actin cytoskeleton and focal adhesions through rho kinase inhibition may facilitate surgical removal of all cells from the capsular bag and thereby reduce PCO.

Angiogenesis is characterized by the development of new vasculature from pre-existing vessels and plays a central role in physiological processes such as embryogenesis, wound healing and female reproductive function, as well as pathophysiologic events including cancer, rheumatoid arthritis and diabetic retinopathy. The growth and metastasis of tumors is critically dependent upon angiogenesis. Angiogenesis is a multistep process involving the endothelial cell (EC) cytoskeleton in migration, proliferation, and barrier stabilization. Angiogenesis is also involved in several ocular diseases such as age-related macular degeneration, diabetic retinopathy, retinopathy of prematurity, corneal angiogenesis, choroidal neovascularization, neovascular, glaucoma, ocular tumorigenesis. Applicants believe that interactions between the cytoskeleton and apoptosis are involved in the intracellular pathways by which angiogenic tube formation occurs. The compounds of the present invention are useful in inhibiting angiogenesis and treating tumors and angiogenesis-associated ophthalmic diseases.

Regulation of the actin cytoskeleton is important in the modulation of fluid transport. Antimitotic drugs markedly interfere with antidiuretic response, strongly implying that cytoskeleton integrity is essential to this function. This role of the cytoskeleton in controlling the epithelial transport is a necessary step in the translocation of the water channel containing particle aggregates and in their delivery to the apical membrane. Osmolality-dependent reorganization of the cytoskeleton and expression of specific stress proteins are important components of the regulatory systems involved in the adaptation of medullary cells to osmotic stress. The compounds of the present invention are useful in directing epithelial function and modulating fluid transport, particularly modulating fluid transport on the ocular surface.

Rho-associated protein kinase inhibitors, due to their regulation of smooth muscle contractility, are useful in the treatment of vasospasm, specifically retinal vasospasm. Relaxation of retinal vasculature increases perfusion rates thereby providing a neuroprotective mechanism (decreased apoptosis and necrosis) in retinal diseases and retinopathies such as glaucoma, ocular hypertension, age-related macular degeneration or retinitis pigmentosa. Additionally, these kinase inhibitors regulate vascular endothelial permeability and as such can play a vasoprotective role to various atherogenic agents.

The present invention provides a method of reducing intraocular pressure, including treating glaucoma such as primary open-angle glaucoma; a method of treating constriction of the visual field; a method of inhibiting wound healing after trabeculectomy; a method of treating posterior capsule opacification following extracapsular cataract extraction and intraocular lens implantation; a method of inhibiting angiogenesis; a method of modulating fluid transport on the ocular surface; a method of controlling vasospasm; a method of increasing tissue perfusion; a method of neuroprotection; and a method of vasoprotection to atherogenic agents. The method comprises the steps of identifying a subject in need of treatment, and administering to the subject a compound of Formula I or Formula II, in an amount effective to alter the actin cytoskeleton, such as by inhibiting actomyosin interactions.

In one embodiment, the pharmaceutical composition of the present invention is administered locally to the eye (e.g., topical, intracameral, intravitreal, subretinal, subconjunctival, retrobulbar or via an implant) in the form of ophthalmic formulations. The compounds of the invention can be combined with ophthalmologically acceptable preservatives, surfactants, viscosity enhancers, penetration enhancers, bioadhesives, antioxidants, buffers, sodium chloride, and water to form an aqueous or non-aqueous, sterile ophthalmic suspension, emulsion, microemulsion, gel, or solution to form the compositions of the invention.

The active compounds disclosed herein can be administered to the eyes of a patient by any suitable means, but are preferably administered by administering a liquid or gel suspension of the active compound in the form of drops, spray or gel. Alternatively, the active compounds can be applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses that are placed on the eye. Another embodiment of the present invention involves the active compound contained within a swab or sponge that can be applied to the ocular surface. Another embodiment of the present invention involves the active compound contained within a liquid spray that can be applied to the ocular surface. Another embodiment of the present invention involves an injection of the active compound directly into the lacrimal tissues or onto the eye surface.

In addition to the topical administration of the compounds to the eye, the compounds of the invention can be administered systematically by any methods known to a skilled person when used for the purposes described above.

The invention is illustrated further by the following examples that are not to be construed as limiting the invention in scope to the specific procedures described in them.

EXAMPLES

Example 1

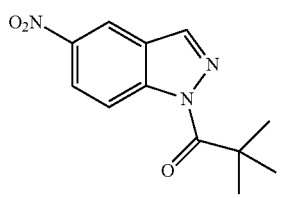 [SMILES: CC(C)(C)C(=O)n1ncc2cc([N+](=O)[O-])ccc21]

2,2-Dimethyl-1-(5-nitro-1H-indazol-1-yl)propan-1-one

A 4 L 3-neck round bottom flask fitted with a nitrogen inlet and mechanical stirrer was charged with a solution of 5-nitroindazole (80.0 g, 0.49 mol) in tetrahydrofuran (1 L). The mixture was cooled to 0° C. and triethylamine (85.4 mL, 0.61 mol) was added. To the mixture was added pivaloyl chloride (63.4 mL, 0.52 mol) dropwise over a period of 15 minutes. The reaction was allowed to warm to 20° C. over a period of 2 hours. The reaction was filtered and concentrated to a dark red oil. To the oil was added methylene chloride (60 mL). The resulting slurry was stirred vigorously, giving a white precipitate that was isolated by filtration. The solid was dried in a vacuum oven at 40° C. overnight to afford the title compound (95 g, 79%).

Example 2

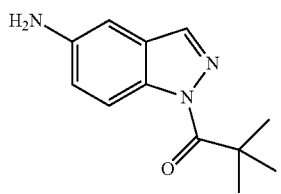 [SMILES: CC(C)(C)C(=O)n1ncc2cc(N)ccc21]

1-(5-Amino-1H-indazol-1-yl)-2,2-dimethylpropan-1-one Maleate

Into a 0.5 L stainless steel reaction vessel were added 2,2-dimethyl-1-(5-nitro-1H-indazol-1-yl)propan-1-one (25.0 g, 0.10 mol), ethanol (300 mL) and 10% palladium on charcoal (2.0 g, 1.9 mmol). The vessel was sealed, evacuated and refilled with nitrogen three times, and evacuated and refilled with hydrogen to 75 psi. As the hydrogen was consumed, the vessel was refilled until a pressure of 75 psi was maintained. The vessel was degassed and the reaction mixture was removed, filtered over celite, and concentrated to give the desired product as a yellow oil (~22 g, 100% yield). The crude product was dissolved in ethanol (220 mL). A solution of maleic acid (11.8 g, 0.10 mol) in ethanol (60 mL) was added in one portion. The mixture was stirred vigorously. As a precipitate began to form, the mixture was cooled to 0° C. and stirred for thirty minutes. The precipitate was isolated by filtration and dried in a vacuum oven at 30° C. overnight to provide the title compound as a solid (30 g, 90%).

$^1$H NMR (DMSO-d6, 300 MHz): δ 1.45 (s, 9H), 6.22 (s, 2H), 7.00 (m, 2H), 8.07 (m, 1H), 8.23 (s, 1H).

Example 3

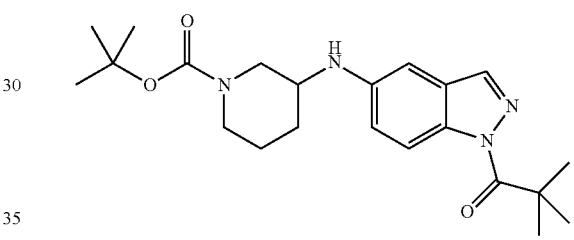

tert-Butyl 3-(1-Pivaloyl-1H-indazol-5-ylamino)piperidine-1-carboxylate

Into a 1 L 3-neck round bottom flask fitted with a nitrogen inlet and mechanical stirrer was added tert-butyl 3-oxopiperidine-1-carboxylate (14.2 g, 0.07 mol), 1,2-dichloroethane (300 mL), and 1-(5-amino-1H-indazol-1-yl)-2,2-dimethylpropan-1-one maleate salt (23.0 g, 0.07 mol). The vessel was purged with nitrogen and stirred at 20° C. for one hour. Sodium triacetoxyborohydride (19.0 g, 0.09 mol) was added, and the reaction was monitored by analytical TLC to completion. The reaction was diluted with 100 mL of saturated sodium bicarbonate. The organic phase was isolated, dried over MgSO$_4$, filtered and evaporated to dryness to afford the title compound as a yellow solid (25.0 g, 91%).

Example 4

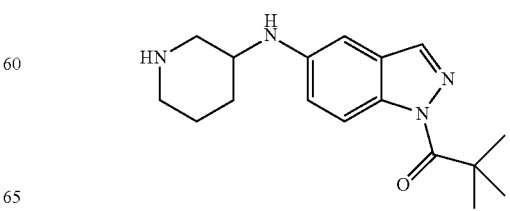

2,2-Dimethyl-1-(5-(piperidin-3-ylamino)-1H-indazol-1-yl)propan-1-one

Into a 1 L 3-neck round bottom flask equipped with an additional funnel and a magnetic stir bar were added tert-butyl 3-(1-pivaloyl-1H-indazol-5-ylamino)piperidine-1-carboxylate (25.0 g, 0.06 mol) and dichloromethane (150 mL). The mixture was cooled to 0° C. and trifluoroacetic acid (150 mL) was added dropwise. The reaction was monitored by HPLC for disappearance of the starting material. Upon completion the reaction was concentrated to give the trifluoroacetate salt of the desired product. Residual trifluoroacetic acid was removed under vacuum. The salt was converted to its free base by partitioning between 75 mL of saturated sodium bicarbonate and ethyl acetate (300 mL). The organic phase was separated, dried over MgSO$_4$, filtered and concentrated to give the title compound as an amorphous solid (15.5 g, 83%).

Example 5

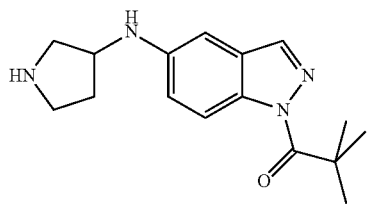 [SMILES: CC(C)(C)C(=O)n1ncc2cc(NC3CCNC3)ccc21]

2,2-Dimethyl-1-(5-(pyrrolidin-3-ylamino)-1H-indazol-1-yl)propan-1-one

Reaction of tert-butyl 3-oxopyrrolidine-1-carboxylate and 1-(5-amino-1H-indazol-1-yl)-2,2-dimethylpropan-1-one maleate salt using the method of Example 3 followed by deprotection using the method of Example 4 afforded the title compound.

Example 6

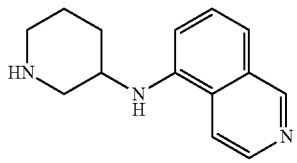 [SMILES: c1cc(NC2CCCNC2)c2ccncc2c1]

N-(Piperidin-3-yl)isoquinolin-5-amine

Reaction of tert-butyl 3-oxopiperidine-1-carboxylate and isoquinolin-5-amine using the method of Example 3 followed by deprotection using the method of Example 4 afforded the title compound.

Example 7

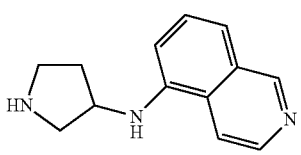

N-(Pyrrolidin-3-yl)isoquinolin-5-amine

Reaction of tert-butyl 3-oxopyrrolidine-1-carboxylate and isoquinolin-5-amine using the method of Example 3 followed by deprotection using the method of Example 4 afforded the title compound.

Example 8

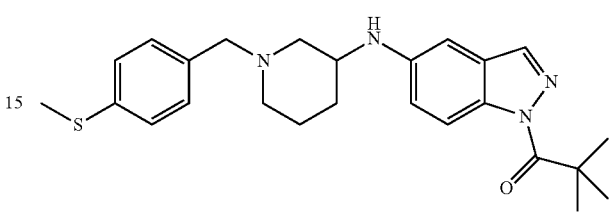

2,2-Dimethyl-1-(5-(1-(4-(methylthio)benzyl)piperidin-3-ylamino)-1H-indazol-1-yl)propan-1-one Into a 25 mL round bottom flask were combined 2,2-dimethyl-1-(5-(piperidin-3-ylamino)-1H-indazol-1-yl)propan-1-one (0.250 g, 0.8 mmol), 1,2-dichloroethane (5 mL), 4-(methylthio)benzaldehyde (0.127 g, 0.8 mmol), glacial acetic acid (50 µL, 0.8 mmol), and sodium triacetoxyborohydride (0.229 g, 1.1 mmol). The reaction was evacuated and refilled with nitrogen. The reaction was monitored by HPLC and was complete upon the disappearance of the starting amine. The reaction was diluted with saturated sodium bicarbonate (10 mL) and dichloromethane (5 mL). After mixing, the organic phase was isolated, dried over MgSO$_4$, filtered and concentrated to give the crude product. Chromatography of the residue on silica gel gave the title compound as an off-white solid (250 mg, 69%).

Example 9

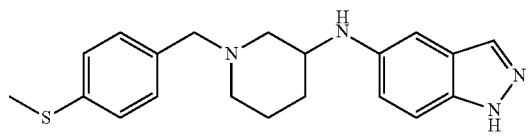 [SMILES: CSc1ccc(CN2CCCC(Nc3ccc4[nH]ncc4c3)C2)cc1]

N-(1-(4-(Methylthio)benzyl)piperidin-3-yl)-1H-indazol-5-amine, Compound 1.008

Into a 25 mL round bottom flask were added 2,2-dimethyl-1-(5-(1-(4-(methylthio)benzyl)piperidin-3-ylamino)-1H-indazol-1-yl)propan-1-one (250 mg, 0.6 mmol), methanol (5 mL), and sodium methoxide (93 mg, 1.7 mmol). The reaction was stirred at room temperature until the starting material was consumed as monitored by HPLC. The mixture was diluted with ethyl acetate (10 mL), washed with water (2×10 mL), and the organic phase was separated, dried over MgSO$_4$, filtered and evaporated to dryness to afford the title compound (180 mg, 89%).

$^1$H NMR (CDCl$_3$, 300 MHz): δ 9.8 (bs, 1H), 7.86 (s, 1H), 7.3-7.18 (m, 5H), 6.82 (m, 2H), 3.6-3.4 (m, 3H), 2.74 (m, 1H), 2.47 (s, 3H), 2.41-2.30 (m, 3H), 1.75 (m, 2H) 1.56 (m, 3H).

Example 10

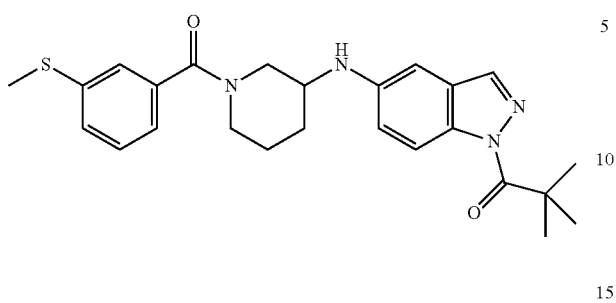

2,2-Dimethyl-1-(5-(1-(3-(methylthio)benzoyl)piperidin-3-ylamino)-1H-indazol-1-yl)propan-1-one To a solution of 3-(methylthio)benzoic acid (200 mg, 1.2 mmol) in DMF (4.5 mL) was added in succession N-(3-dimethylaminopropyl)-N'-ethylcarbodiimide hydroiodide (345 mg, 1.75 mmol) 1-hydroxybenzotriazole hydrate (186 mg, 1.2 mmol) and diisopropylethylamine (0.630 mL, 3.6 mmol). After stirring at room temperature for 10 min, 2,2-dimethyl-1-(5-(piperidin-3-ylamino)-1H-indazol-1-yl)propan-1-one (300 mg, 1.0 mmol) was added in one portion. The solution was stirred under a nitrogen atmosphere overnight. The solution was poured into 1.0 M HCl (20 mL), extracted twice with EtOAc, and the organic phases were washed with 10% NaOH, dried over $Na_2SO_4$ and evaporated. Chromatography of the residue on silica gel, eluting with EtOAc/heptane, gave the title compound as a pale yellow foam (240 mg, 53%).

Example 11

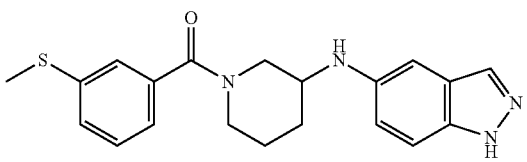 [SMILES: CSc1cccc(C(=O)N2CCCC(Nc3ccc4[nH]ncc4c3)C2)c1]

N-(1-(3-(Methylthio)benzyl)piperidin-3-yl)-1H-indazol-5-amine, Compound 1.040

Into a round bottom flask was added 2,2-dimethyl-1-(5-(1-(3-(methylthio)benzoyl)-piperidin-3-ylamino)-1H-indazol-1-yl)propan-1-one (240 mg, 0.655 mmol) and THF (3 mL). The solution was heated to 60° C. and borane-dimethyl sulfide complex in THF (3.0 mL of a 2.0M solution in THF, 6.0 mmol) was added, allowing dimethyl sulfide to distill off. After the starting material was consumed, the reaction was evaporated, 5N NaOH (10 mL) was added, and the mixture was extracted with EtOAc. The organic phases were dried, evaporated, and the residue was chromatographed on silica gel, eluting with 3/1-EtOAc/Heptane to afford the title compound (95 mg, 41%).

$^1$H NMR (CDCl$_3$, 300 MHz): δ 7.87 (s, 1H), 7.26-7.15 (m, 4H), 7.11 (t, J=7.2 Hz, 1H), 6.83 (m, 2H), 3.61 (m, 1H) 3.50 (m, 2H), 2.80 (m, 1H), 2.49 (s, 3H), 2.43 (bs, 2H), 2.29 (bs, 1H), 1.75 (m, 2H) 1.59 (m, 3H).

Example 12

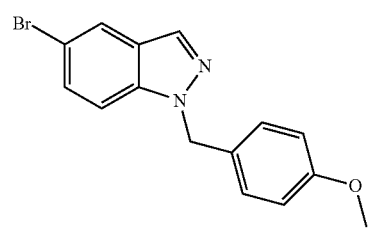 [SMILES: COc1ccc(Cn2ncc3cc(Br)ccc32)cc1]

5-Bromo-1-(4-methoxybenzyl)-1H-indazole

To a suspension of KOtBu (8.13 g, 72.4 mmol) in THF (60 mL) was added 5-bromo-1H-indazole (12.98 g, 65.9 mmol) in THF (60 mL). After 30 min, 4-methoxybenzyl chloride (9.38 mL, 69.2 mmol) was added (neat) and the resulting pale yellow solution was stirred 48 h. The reaction was quenched by addition of saturated NH$_4$Cl solution, and the mixture was extracted with EtOAc. Evaporation of the organic phase followed by column chromatography of the residue on silica gel, eluting with 1/9-EtOAc/heptane, afforded the title compound, which was recrystallized from toluene/heptane (1/5) to afford the title compound as colorless cubes (7.65 g, 37%). Also recovered from the chromatography was 5-bromo-2-(4-methoxybenzyl)-2H-indazole (8.0 g, 38%)

Example 13

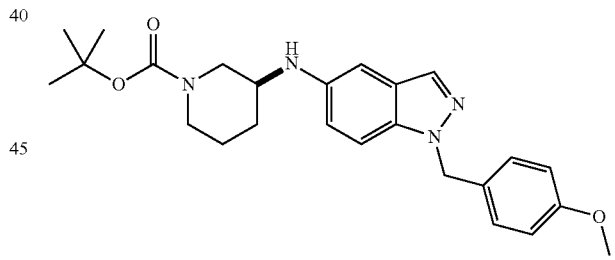

(S)-tert-Butyl 3-(1-(4-Methoxybenzyl)-1H-indazol-5-ylamino)piperidine-1-carboxylate To a solution of 5-bromo-1-(4-methoxybenzyl)-1H-indazole (870 mg, 2.75 mmol) in toluene (10 mL) was added in succession (S)-tert-butyl 3-aminopiperidine-1-carboxylate (660 mg, 3.3 mmol), sodium tert-butoxide (475 mg, 5 mmol), and rac-(±)-BINAP (180 mg, 0.29 mmol). The flask was evacuated and refilled with nitrogen three times, after which Pd$_2$dba$_3$ (83 mg, 1.5 mol %) was added. The flask was again purged with nitrogen three times, and was then heated to 80° C. overnight. The solution was cooled to room temperature and then filtered through a pad of celite, washing with additional toluene. The toluene solution was then loaded directly onto a silica gel column that had been packed with heptane.

The column was flushed with 2 column volumes of heptane, and then eluted with 40/60-EtOAc/heptane to afford the title compound (1.00 g 82%).

Example 14

(S)—N-(Piperidin-3-yl)-1H-indazol-5-amine

A solution of (S)-tert-butyl 3-(1-(4-methoxybenzyl)-1H-indazol-5-ylamino)piperidine-1-carboxylate (240 mg, 0.55 mmol) in TFA (2 mL) was stirred at room temperature for 15 min, after which the solvent was evaporated. Chromatography of the residue on silica gel, eluting first with dichloromethane and then with 90:9:1 dichloromethane:MeOH:NH$_4$OH, afforded the material in which the BOC protecting group had been removed.

The residue thus obtained was then dissolved again in TFA (2 mL), along with 1,3-dimethoxybenzene (151 mg, 1.1 mmol) and was heated to reflux overnight. The TFA was removed by evaporation, and the residue was again chromatographed as described above to afford the title compound (90 mg, 75% over the 2 steps).

Example 15

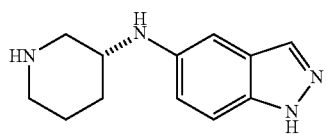

(R)—N-(Piperidin-3-yl)-1H-indazol-5-amine

Reaction of 5-bromo-1-(4-methoxybenzyl)-1H-indazole and (R)-tert-butyl 3-aminopiperidine-1-carboxylate using the method of Example 13 followed by deprotection using the method of Example 14 afforded the title compound.

Example 16

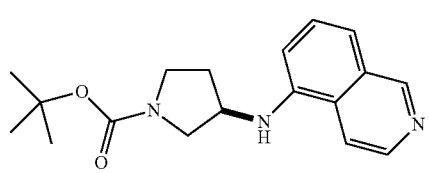 [SMILES: CC(C)(C)OC(=O)N1CC[C@@H](Nc2cccc3cnccc23)C1]

(R)-tert-Butyl 3-(Isoquinolin-5-ylamino)pyrrolidine-1-carboxylate

Into a 50 mL round bottom flask were added 5-bromoisoquinoline (1.12 g, 5.4 mmol), toluene (10 mL), (R)-tert-butyl 3-aminopyrrolidine-1-carboxylate (1.00 g, 5.4 mmol), palladium acetate (0.18 g, 0.8 mmol), rac-(±)-BINAP (0.500 g, 0.8 mmol), and cesium carbonate (2.80 g, 8.6 mmol). The vessel was evacuated, refilled with nitrogen and stirred at 80° C. for 12 h. The mixture was diluted with ethyl acetate (20 mL), washed with water (10 mL), and the organic phase was dried over MgSO$_4$, filtered and evaporated to afford the title compound (1.00 g, 59%). This material was of sufficient quality to be used without further purification.

Example 17

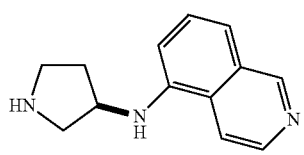 [SMILES: c1cc(N[C@@H]2CCNC2)c2ccncc2c1]

(R)—N-(Pyrrolidin-3-yl)isoquinolin-5-amine

Deprotection of (R)-tert-butyl 3-(isoquinolin-5-ylamino)pyrrolidine-1-carboxylate following the method of Example 4 afforded the title compound.

Example 18

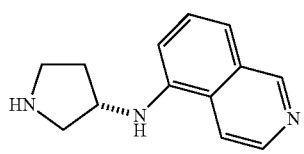 [SMILES: c1cc(N[C@H]2CCNC2)c2ccncc2c1]

(S)—N-(Pyrrolidin-3-yl)isoquinolin-5-amine

Reaction of (S)-tert-butyl 3-aminopyrrolidine-1-carboxylate and 5-bromoisoquinoline using the method of Example 16 followed by deprotection using the method of Example 4 afforded the title compound.

Example 19

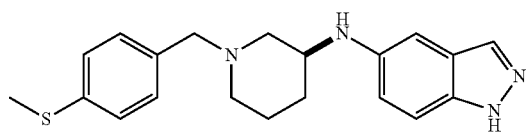

(S)—N-(1-(4-(Methylthio)benzyl)piperidin-3-yl)-1H-indazol-5-amine, Compound 1.075

Reaction of (S)—N-(piperidin-3-yl)-1H-indazol-5-amine and 4-(methylthio)-benzaldehyde using the method of Example 8 and using THF as the reaction solvent afforded the title compound.

Example 20

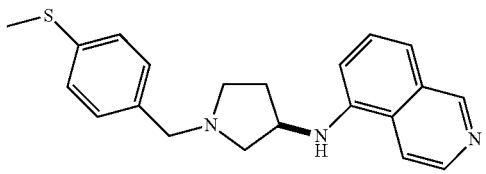 [SMILES: CSc1ccc(CN2CC[C@@H](Nc3cccc4cnccc34)C2)cc1]

(R)—N-(1-(4-(Methylthio)benzyl)pyrrolidin-3-yl)isoquinolin-5-amine, Compound 2.026

Reaction of (R)—N-(pyrrolidin-3-yl)isoquinolin-5-amine and 4-(methylthio)-benzaldehyde using the method of Example 8 afforded the title compound.

Example 21

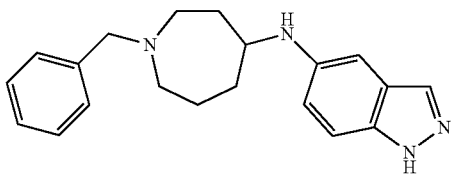 [SMILES: c1ccc(CN2CCCC(Nc3ccc4[nH]ncc4c3)CC2)cc1]

N-(1-Benzylazepan-4-yl)-1H-indazol-5-amine, Compound 1.031

The title compound was prepared by reaction of 2,2-dimethyl-1-(5-(piperidin-3-ylamino)-1H-indazol-1-yl)propan-1-one with tert-butyl 4-oxoazepane-1-carboxylate using the method of Example 3, deprotection using the method of Example 4, reaction with benzaldehyde following the method of Example 8, and final deprotection using the method of Example 9.

$^1$H NMR (CDCl$_3$, 300 MHz): δ 7.88 (s, 1H), 7.36-7.26 (m, 6H), 6.80 (m, 2H), 3.75 (m, 1H), 3.67 (s, 2H), 2.80-2.57 (m, 4H), 2.05-1.27 (m, 8H).

Examples 22-81

Reaction of 2,2-dimethyl-1-(5-(piperidin-3-ylamino)-1H-indazol-1-yl)propan-1-one with the appropriate aldehydes using the method of Example 8 followed by deprotection using the method of Example 9 afforded the compounds in Examples 22-81:

Example 22

N-(1-(4-(Methylsulfonyl)benzyl)piperidin-3-yl)-1H-indazol-5-amine, Compound 1.001

$^1$H NMR (DMSO-d$^6$ 300 MHz): δ 12.53 (bs, 1H), 7.86 (s, 1H), 7.34 (m, 4H), 7.22 (d, J=9.0 Hz, 1H), 6.78 (dd, J=1.8, 9.0 Hz, 1H), 6.60 (s, 1H), 5.05 (s, J=8.4 Hz, 1H), 3.47 (bs, 2H), 3.30 (m, 4H), 2.90 (d, J=9.3 Hz, 1H), 2.60 (m, 1H), 2.03 (m, 1H), 1.85 (m, 2H), 1.65 (m, 1H), 1.55 (m, 1H) 1.22 (m, 1H).

Example 23

3-((3-(1H-Indazol-5-ylamino)piperidin-1-yl)methyl)benzonitrile, Compound 1.002

$^1$H NMR (CDCl$_3$, 300 MHz): δ 7.88 (s, 1H), 7.65 (s, 1H), 7.53 (m, 2H), 7.39 (t, J=7.5 Hz, 1H), 7.31 (m, 1H), 6.82 (m, 2H), 3.61 (bs, 1H), 3.51 (m, 2H), 2.78 (m, 1H), 2.45-2.35 (m, 3H), 1.77 (m, 2H), 1.57 (m, 2H).

Example 24

N-(4-((3-(1H-Indazol-5-ylamino)piperidin-1-yl)methyl)phenyl)acetamide, Compound 1.003

$^1$H NMR (CDCl$_3$, 300 MHz): δ 9.80 (bs, 1H), 7.85 (s, 1H), 7.42 (m, 2H), 7.30-7.26 (m, 3H), 7.08 (s, 1H), 6.82 (m, 2H), 3.60 (bs, 1H), 3.45 (m, 2H), 2.74 (m, 1H), 2.45-2.35 (m, 3H), 2.18 (s, 3H), 1.76 (m, 2H), 1.60 (m, 2H).

Example 25

N-(1-(Biphenyl-4-ylmethyl)piperidin-3-yl)-1H-indazol-5-amine, Compound 1.009

$^1$H NMR (CDCl$_3$, 300 MHz): δ 7.86 (s, 1H), 7.59 (m, 4H), 7.43-7.29 (m, 6H), 6.84 (m, 2H), 3.62 (bs, 1H), 3.56 (dd, J=10.2, 21.0 Hz, 2H), 2.80 (m, 1H), 2.45-2.30 (m, 3H), 1.75 (m, 2H) 1.55 (m, 3H).

Example 26

N-(1-(1H-Imidazol-1-yl)benzyl)piperidin-3-yl)-1H-indazol-5-amine, Compound 1.010

$^1$H NMR (CDCl$_3$, 300 MHz): δ 7.86 (s, 1H), 7.83 (s, 1H), 7.42 (m, 2H), 7.29 (m, 5H), 6.82 (m, 2H), 3.63 (bs, 1H), 3.56 (dd, J=13.5, 27.3 Hz, 2H), 2.78 (m, 1H), 2.42-2.30 (m, 3H), 1.75 (m, 2H) 1.58 (m, 2H).

Example 27

N-(1-(4-(Pyrrolidin-1-yl)benzyl)piperidin-3-yl)-1H-indazol-5-amine, Compound 1.011

$^1$H NMR (CDCl$_3$, 300 MHz): δ 10.15 (bs, 1), 7.86 (s, 1H), 7.27 (m, 1H), 7.16 (d, J=8.4 Hz, 2H), 6.82 (m, 2H), 6.52 (d, J=8.4 Hz, 2H), 3.64 (bs, 1H), 3.53 (bs, 2H), 3.23 (m, 5H), 2.83 (bs, 1H), 2.42-2.30 (m, 3H), 2.00 (m, 4H), 1.75 (m, 2H) 1.58 (m, 2H).

Example 28

N-(1-(4-Morpholinobenzyl)piperidin-3-yl)-1H-indazol-5-amine, Compound 1.012

$^1$H NMR (CDCl$_3$, 300 MHz): δ 7.86 (s, 1H), 7.27 (m, 3H), 6.84 (m, 4H), 3.87 (m, 4H), 3.60 (bs, 1H), 3.47 (m, 2H), 3.13 (m, 4H), 2.76 (m, 1H), 2.42-2.30 (m, 3H), 1.75 (m, 2H) 1.58 (m, 2H).

Example 29

N-(1-(4-Isobutylbenzyl)piperidin-3-yl)-1H-indazol-5-amine, Compound 1.013

$^1$H NMR (CDCl$_3$, 300 MHz): δ 9.95 (bs, 1H), 7.86 (s, 1H), 7.27 (m, 3H), 7.08 (d, J=7.8 Hz, 2H), 6.82 (m, 2H), 3.95 (bs, 1H), 3.60 (bs, 1H), 3.50 (m, 2H), 2.76 (m, 1H), 2.42-2.30 (m, 5H), 1.86 (m, 1H), 1.75 (m, 2H) 1.58 (m, 3H), 0.89 (d, J=6.6 Hz, 6H).

Example 30

N-(1-(4-Butylbenzyl)piperidin-3-yl)-1H-indazol-5-amine, Compound 1.014

$^1$H NMR (CDCl$_3$, 300 MHz): δ 9.85 (bs, 1H), 7.86 (s, 1H), 7.27 (m, 1H), 7.22 (d, J=8.1 Hz, 2H), 7.12 (d, J=8.1 Hz, 2H), 6.82 (m, 2H), 3.60 (bs, 1H), 3.49 (m, 2H), 2.76 (d, J=9.6 Hz, 1H), 2.56 (t, J=7.8 Hz, 2H), 2.42-2.30 (m, 3H), 1.75 (m, 2H) 1.58 (m, 4H), 1.30 (sex, J=7.8 Hz, 2H), 0.92 (t, J=7.8 Hz, 3H).

Example 31

N-(1-(4-Isopropoxybenzyl)piperidin-3-yl)-1H-indazol-5-amine, Compound 1.015

$^1$H NMR (CDCl$_3$, 300 MHz): δ 9.80 (bs, 1H), 7.86 (s, 1H), 7.25 (m, 3H), 6.83 (m, 4H), 4.52 (p, J=6 Hz, 2H), 3.60 (bs, 1H), 3.45 (bs, 2H), 2.76 (m, 1H), 2.42-2.30 (m, 3H), 1.73 (m, 2H) 1.57 (m, 2H), 1.32 (d, J=6 Hz, 6H).

Example 32

N-(1-(2,3-Dimethylbenzyl)piperidin-3-yl)-1H-indazol-5-amine, Compound 1.016

$^1$H NMR (CDCl$_3$, 300 MHz): δ 7.86 (s, 1H), 7.28 (m, 1H), 7.05 (m, 3H) 6.82 (m, 2H), 3.60 (bs, 1H), 3.45 (m, 2H), 2.70 (m, 1H), 2.42 (m, 2H), 2.30 (s, 6H), 1.75 (m, 2H) 1.58 (m, 3H).

Example 33

N-(1-(4-(Ethylthio)benzyl)piperidin-3-yl)-1H-indazol-5-amine, Compound 1.017

$^1$H NMR (CDCl$_3$, 300 MHz): δ 10.15 (bs, 1H), 7.87 (s, 1H), 7.25 (m, 5H), 6.82 (m, 2H), 3.95 (bs, 2H), 3.60 (bs, 1H), 3.49 (dd, J=13.5, 20.7 Hz, 2H), 2.91 (q, J=7.2 Hz, 2H), 2.76 (d, J=9.6 Hz, 1H), 2.42-2.30 (m, 3H), 1.75 (m, 2H) 1.58 (m, 2H), 1.30 (t, J=7.2 Hz, 3H).

Example 34

2-(4-((3-(1H-Indazol-5-ylamino)piperidin-1-yl)methyl)phenoxy)ethanol, Compound 1.018

$^1$H NMR (CDCl$_3$, 300 MHz): δ 7.85 (s, 1H), 7.21 (m, 3H), 6.79 (m, 4H), 4.05 (m, 2H), 3.95 (m, 2H), 3.59 (bs, 1H), 3.50 (dd, J=11.7, 24.3 Hz, 2H), 2.74 (d, J=8.7 Hz, 1H), 2.42-2.30 (m, 3H), 1.77 (m, 2H) 1.58 (m, 2H).

Example 35

N-(1-(4-((Dimethylamino)methyl)benzyl)piperidin-3-yl)-1H-indazol-5-amine, Compound 1.019

$^1$H NMR (CDCl$_3$, 300 MHz): δ 10.30 (bs, 1H), 7.85 (s, 1H), 7.30-7.20 (m, 5H), 6.80 (m, 2H), 3.95 (bs, 2H), 3.59 (bs, 1H), 3.49 (dd, J=13.2, 18.6 Hz, 2H), 3.42 (s, 2H), 2.74 (d, J=8.7 Hz, 1H), 2.42-2.30 (m, 3H), 2.24 (s, 6H), 1.76 (m, 2H) 1.58 (m, 2H).

Example 36

N-(1-(4-Cyclopropylbenzyl)piperidin-3-yl)-1H-indazol-5-amine, Compound 1.020

$^1$H NMR (CDCl$_3$, 300 MHz): δ 9.85 (bs, 1H), 7.87 (s, 1H), 7.30-7.20 (m, 3H), 7.03 (m, 2H), 6.83 (m, 2H), 4.0 (bs, 1H), 3.60 (bs, 1H), 3.53 (dd, J=13.2, 18.9 Hz, 2H), 2.74 (d, J=8.7 Hz, 1H), 2.42-2.30 (m, 3H), 1.87 (m, 1H), 1.76 (m, 2H) 1.58 (m, 2H), 0.98 (m, 2H), 0.72 (m, 1H).

Example 37

N-(1-(3-Cyclopropylbenzyl)piperidin-3-yl)-1H-indazol-5-amine, Compound 1.021

$^1$H NMR (CDCl$_3$, 300 MHz): δ 9.85 (bs, 1H), 7.87 (s, 1H), 7.32 (m, 1H), 7.21 (m, 1H), 7.18 (m, 1H), 7.10 (m, 1H), 6.97 (m, 1H), 6.83 (m, 2H), 4.0 (bs, 1H), 3.62 (bs, 1H), 3.49 (m, 2H), 2.76 (m, 1H), 2.42-2.30 (m, 3H), 1.89 (m, 1H), 1.76 (m, 2H) 1.58 (m, 2H), 0.98 (m, 2H), 0.72 (m, 1H).

Example 38

N-(1-(4-(Trifluoromethoxy)benzyl)piperidin-3-yl)-1H-indazol-5-amine, Compound 1.022

$^1$H NMR (CDCl$_3$, 300 MHz): δ 9.90 (bs, 1H), 7.86 (s, 1H), 7.35 (d, J=8.4 Hz, 2H), 7.27 (m, 1H), 7.15 (d, J=8.1 Hz, 2H), 6.83 (m, 2H), 3.62 (bs, 1H), 3.51 (m, 2H), 2.76 (m, 1H), 2.42-2.30 (m, 3H), 1.76 (m, 2H) 1.60 (m, 2H).

Example 39

N-(1-(4-Isopropylbenzyl)piperidin-3-yl)-1H-indazol-5-amine, Compound 1.023

$^1$H NMR (CDCl$_3$, 300 MHz): δ 7.86 (s, 1H), 7.27 (m, 5H), 6.82 (m, 2H), 3.60 (bs, 1H), 3.50 (m, 2H), 2.90 (m, 1H), 2.76 (m, 1H), 2.42-2.30 (m, 3H), 1.75 (m, 2H) 1.58 (m, 3H), 1.15 (m, 6H).

Example 40

N-(1-(2,4-Dimethylbenzyl)piperidin-3-yl)-1H-indazol-5-amine, Compound 1.024

$^1$H NMR (CDCl$_3$, 300 MHz): δ 7.85 (s, 1H), 7.27 (d, J=9.0 Hz, 1H), 7.13 (d, J=7.8 Hz, 1H), 6.94 (m, 2H), 6.80 (m, 2H), 3.60 (bs, 1H), 3.43 (m, 2H), 2.70 (m, 1H), 2.48-2.30 (m, 3H), 2.37 (s, 3H), 2.29 (s, 3H), 1.68 (m, 2H) 1.56 (m, 2H).

Example 41

(4-((3-(1H-Indazol-5-ylamino)piperidin-1-yl)methyl)phenyl)methanol, Compound 1.025

$^1$H NMR (CDCl$_3$, 300 MHz): δ 10.2 (bs, 1H), 7.86 (s, 1H), 7.37 (dd, J=1.5, 7.5 Hz, 1H), 7.25 (m, 2H), 6.93 (t, J=7.5 Hz, 1H), 6.83 (m, 3H), 3.80 (s, 3H), 3.60 (bs, 1H), 2.85 (m, 1H), 2.48-2.30 (m, 3H), 1.75 (m, 2H) 1.56 (m, 2H).

Example 42

N-(1-(4-(Cyclopropylthio)benzyl)piperidin-3-yl)-1H-indazol-5-amine, Compound 1.026

$^1$H NMR (CDCl$_3$, 300 MHz): δ 7.89 (s, 1H), 7.3-7.23 (m, 5H), 6.83 (m, 2H), 3.62 (m, 1H), 3.51 (dd, J=13.5, 21.6 Hz, 2H), 2.77 (d, J=8.1 Hz, 1H), 2.45-2.30 (m, 3H), 2.12 (m, 1H), 1.75 (m, 2H) 1.56 (m, 3H), 1.05 (m, 2H), 0.70 (m, 2H).

Example 43 tert-Butyl 4-((3-(1H-Indazol-5-ylamino)piperidin-1-yl)methyl)benzylcarbamate, Compound 1.027

$^1$H NMR (CDCl$_3$, 300 MHz): δ 7.85 (s, 1H), 7.3-7.20 (m, 5H), 6.80 (m, 2H), 4.85 (bs, 1H), 4.28 (d, J=4.5 Hz, 2H), 3.75-3.53 (m, 4H), 2.80 (m, 1H), 2.45-2.30 (m, 3H), 1.75 (m, 2H) 1.56 (m, 3H), 1.46 (s, 9H).

Example 44

N-(1-(4-(Methylthiomethyl)benzyl)piperidin-3-yl)-1H-indazol-5-amine, Compound 1.028

$^1$H NMR (CDCl$_3$, 300 MHz): δ 7.86 (s, 1H), 7.3-7.23 (m, 5H), 6.82 (m, 2H), 3.65 (s, 2H), 3.62 (m, 1H), 3.53 (m, 2H), 2.80 (m, 1H), 2.45-2.30 (m, 3H), 1.97 (s, 3H), 1.75 (m, 2H) 1.56 (m, 3H).

Example 45

N-(1-(4-(Methylsulfonylmethyl)benzyl)piperidin-3-yl)-1H-indazol-5-amine, Compound 1.029

$^1$H NMR (CDCl$_3$, 300 MHz): δ 7.85 (s, 1H), 7.39-7.26 (m, 5H), 6.82 (m, 2H), 4.21 (s, 2H), 3.61 (bs, 1H), 3.54 (dd, J=10.2, 19.5 Hz, 2H), 2.74 (m, 1H), 2.69 (s, 3H), 2.45-2.35 (m, 3H), 1.76 (m, 2H), 1.60 (m, 2H).

Example 46

N-(1-(4-(Thiophen-2-yl)benzyl)piperidin-3-yl)-1H-indazol-5-amine, Compound 1.030

Example 47

N-(1-(4-(Dimethylamino)benzyl)piperidin-3-yl)-1H-indazol-5-amine, Compound 1.032

$^1$H NMR (CDCl$_3$, 300 MHz): δ 7.88 (s, 1H), 7.23 (m, 3H), 6.82 (m, 2H), 6.69 (d, J=8.4 Hz, 2H), 3.60 (bs, 1H), 3.47 (m, 2H), 2.93 (s, 6H), 2.80 (m, 1H), 2.45-2.30 (m, 3H), 1.75 (m, 2H) 1.56 (m, 3H).

Example 48

N-(1-(4-Ethylbenzyl)piperidin-3-yl)-1H-indazol-5-amine, Compound 1.033

$^1$H NMR (CDCl$_3$, 300 MHz): δ 10.30 (bs, 1H), 7.87 (s, 1H), 7.25 (m, 3H), 7.16 (m, 2H), 6.82 (m, 2H), 4.00 (bs, 1H), 3.60 (bs, 1H), 3.51 (m, 2H), 2.75 (m, 1H), 2.63 (q, J=7.5 Hz, 2H), 2.50-2.35 (m, 3H), 1.75 (m, 2H), 1.55 (m, 2H), 1.23 (t, J=7.5 Hz, 3H).

Example 49

N-(1-(4-Ethynylbenzyl)piperidin-3-yl)-1H-indazol-5-amine, Compound 1.034

Prepared by deprotection of Compound 1.027 using the method of Example 4.

$^1$H NMR (CDCl$_3$, 300 MHz): δ 7.86 (s, 1H), 7.43 (d, J=8.4 Hz, 2H), 7.26 (m, 3H), 6.84 (m, 2H), 3.60 (bs, 1H), 3.49 (dd, J=5.4, 9.1 Hz, 2H), 3.05 (s, 1H), 2.74 (m, 1H), 2.41-2.30 (m, 3H), 1.75 (m, 2H) 1.56 (m, 3H).

Example 50

N-(1-(4-(Aminomethyl)benzyl)piperidin-3-yl)-1H-indazol-5-amine, Compound 1.035

$^1$H NMR (CDCl$_3$, 300 MHz): δ 7.85 (s, 1H), 7.39-7.26 (m, 7H), 6.82 (m, 2H), 4.65 (s, 2H), 4.21 (s, 2H), 3.61-3.4 (m, 5H), 2.74 (m, 1H), 2.45-2.35 (m, 3H), 1.76 (m, 2H), 1.60 (m, 2H).

Example 51

1-(4-((3-(1H-Indazol-5-ylamino)piperidin-1-yl)methyl)phenyl)ethanone, Compound 1.036

$^1$H NMR (CDCl$_3$, 300 MHz): δ 7.89 (m, 3H), 7.42 (d, J=7.8 Hz, 2H), 7.33 (m, 1H), 6.84 (m, 2H), 3.60 (bs, 1H), 3.57 (dd, J=13.5, 24.9 Hz, 2H), 2.74 (m, 1H), 2.59 (s, 3H), 2.41-2.30 (m, 3H), 1.75 (m, 2H) 1.56 (m, 3H).

Example 52

N-(1-(4-Vinylbenzyl)piperidin-3-yl)-1H-indazol-5-amine, Compound 1.037

$^1$H NMR (CDCl$_3$, 300 MHz): δ 7.86 (s, 1H), 7.32 (d, J=9.0 Hz, 2H), 7.29 (m, 3H), 6.84 (m, 2H), 6.70 (dd, J=10.8, 17.7 Hz, 1H), 5.73 (d, J=17.7 Hz, 1H), 5.22 (d, J=10.8 Hz, 1H), 3.60 (bs, 1H), 3.54 (m, 2H), 2.74 (m, 1H), 2.41-2.30 (m, 3H), 1.75 (m, 2H) 1.56 (m, 3H).

Example 53

4-((3-(1H-Indazol-5-ylamino)piperidin-1-yl)methyl)benzonitrile, Compound 1.038

$^1$H NMR (CDCl$_3$, 300 MHz): δ 7.86 (s, 1H), 7.68 (d, J=8.4 Hz, 2H), 7.38 (d, J=8.1 Hz, 2H), 7.29 (d, J=8.7 Hz, 1H), 6.84 (m, 2H), 3.92 (s, 2H), 3.60 (bs, 1H), 3.54 (dd, J=13.2, 21.6 Hz, 2H), 2.74 (m, 1H), 2.41-2.30 (m, 3H), 1.75 (m, 2H) 1.56 (m, 3H).

Example 54

2-(3-((3-(1H-Indazol-5-ylamino)piperidin-1-yl)methyl)phenoxy)ethanol, Compound 1.039

$^1$H NMR (CDCl$_3$, 300 MHz): δ 7.86 (s, 1H), 7.31-7.2 (m, 2H), 6.94 (m, 2H), 6.83 (m, 3H), 4.09 (m, 2H), 3.96 (m, 2H), 3.61 (m, 1H) 3.50 (m, 2H), 2.80 (m, 1H), 2.45 (m, 3H), 1.75 (m, 2H) 1.59 (m, 3H).

Example 55

N-(1-(3-(Methylsulfonylmethyl)benzyl)piperidin-3-yl)-1H-indazol-5-amine, Compound 1.041

$^1$H NMR (CDCl$_3$, 300 MHz): δ 7.85 (s, 1H), 7.41 (s, 1H), 7.36-7.26 (m, 4H), 6.83 (dd, J=2.1, 9.3 Hz, 1H), 6.79 (d, J=1.5 Hz, 1H), 4.20 (s, 2H), 3.63 (m, 1H) 3.55 (dd, J=13.5, 34.2 Hz, 2H), 2.70 (m, 1H), 2.67 (s, 3H), 2.41 (bs, 2H), 2.29 (bs, 1H), 1.75 (m, 2H) 1.59 (m, 3H).

Example 56

3-(4-((3-(1H-Indazol-5-ylamino)piperidin-1-yl)methyl)phenyl)prop-2-yn-1-ol, Compound 1.042

$^1$H NMR (CDCl$_3$, 300 MHz): δ 7.86 (s, 1H), 7.32 (d, J=8.4 Hz, 2H), 7.23 (m, 3H), 6.80 (m, 2H), 4.49 (s, 2H), 3.57 (bs, 1H) 3.48 (dd, J=13.2, 19.8 Hz, 2H), 2.69 (d, J=9.0 Hz, 1H), 2.42 (bs, 2H), 2.27 (bs, 1H), 1.75 (m, 2H) 1.56 (m, 3H).

Example 57

4-(4-((3-(1H-Indazol-5-ylamino)piperidin-1-yl)methyl)phenyl)but-3-yn-1-ol, Compound 1.043

$^1$H NMR (CDCl$_3$, 300 MHz): δ 7.86 (s, 1H), 7.32 (d, J=8.1 Hz, 2H), 7.23 (m, 3H), 6.80 (m, 2H), 3.82 (t, J=6.0 Hz, 2H), 3.55 (bs, 1H) 3.47 (dd, J=13.2, 19.5 Hz, 2H), 2.67 (t, J=6.0 Hz, 1H), 2.66 (m, 1H), 2.41 (bs, 2H), 2.26 (bs, 1H), 1.75 (m, 2H) 1.56 (m, 3H).

Example 58

N-(1-(4-(Cyclopropylethynyl)benzyl)piperidin-3-yl)-1H-indazol-5-amine, Compound 1.044

$^1$H NMR (CDCl$_3$, 300 MHz): δ 7.87 (s, 1H), 7.33-7.15 (m, 5H), 6.83 (m, 2H), 3.58 (bs, 1H) 3.48 (dd, J=13.5, 19.5 Hz, 2H), 2.75 (d, J=9.3 Hz, 1H), 2.35 (m, 3H), 1.75 (m, 2H) 1.59 (m, 3H), 1.44 (m, 1H), 0.93-0.76 (m, 4H).

Example 59

N-(1-(3-Bromobenzyl)piperidin-3-yl)-1H-indazol-5-amine, Compound 1.045

$^1$H NMR (CDCl$_3$, 300 MHz): δ 9.80 (bs, 1H) 7.87 (s, 1H), 7.52 (s, 1H), 7.38-7.14 (m, 4H), 6.83 (m, 2H), 3.90 (bs, 1H), 3.59 (m, 1H) 3.47 (dd, J=13.5, 15.3 Hz, 2H), 2.76 (d, J=9.9 Hz, 1H), 2.41 (bs, 2H), 2.29 (bs, 1H), 1.75 (m, 2H) 1.59 (m, 3H).

Example 60

3-((3-(1H-Indazol-5-ylamino)piperidin-1-yl)methyl)phenol, Compound 1.046

$^1$H NMR (CDCl$_3$, 300 MHz): δ 7.86 (s, 1H), 7.26 (d, J=9.3 Hz, 1H), 7.15 (t, J=7.8 Hz, 1H), 6.83 (m, 4H), 6.71 (dd, J=1.5, 7.5 Hz, 1H), 3.59 (m, 1H) 3.47 (dd, J=12.9, 20.1 Hz, 2H), 2.76 (d, J=9.3 Hz, 1H), 2.42 (bs, 2H), 2.36 (bs, 1H), 1.75 (m, 2H) 1.59 (m, 3H).

Example 61

N-(1-(3-Ethynylbenzyl)piperidin-3-yl)-1H-indazol-5-amine, Compound 1.047

$^1$H NMR (CDCl$_3$, 300 MHz): δ 7.87 (s, 1H), 7.48 (s, 1H), 7.37 (d, J=7.2 Hz, 1H), 7.33-7.24 (m, 3H), 6.82 (m, 2H), 3.60 (m, 1H) 3.48 (m, 2H), 3.08 (s, 1H), 2.76 (d, J=10.5 Hz, 1H), 2.40 (bs, 2H), 2.30 (bs, 1H), 1.75 (m, 2H) 1.59 (m, 3H).

Example 62

N-(1-(3-(Methylsulfonyl)benzyl)piperidin-3-yl)-1H-indazol-5-amine, Compound 1.048

$^1$H NMR (CDCl$_3$, 300 MHz): δ 7.95 (s, 1H), 7.87 (s, 1H), 7.80 (d, J=7.5 Hz, 1H), 7.62 (d, J=7.5 Hz, 1H), 7.50 (t, J=7.8 Hz, 1H), 7.28 (d, J=9.0 Hz, 1H), 6.83 (m, 2H), 3.60 (m, 1H) 3.56 (dd, J=13.2, 21.6 Hz, 2H), 3.02 (s, 3H), 2.76 (d, J=10.2 Hz, 1H), 2.45 (bs, 2H), 2.32 (bs, 1H), 1.77 (m, 2H) 1.61 (m, 3H).

Example 63

N-(3-((3-(1H-Indazol-5-ylamino)piperidin-1-yl)methyl)phenyl)methanesulfonamide, Compound 1.051

$^1$H NMR (CDCl$_3$, 300 MHz): δ 7.85 (s, 1H), 7.32-7.25 (m, 2H), 7.09 (m, 2H), 6.87 (dd, J=2.1, 9.0 Hz, 1H), 6.79 (s, 1H), 3.61 (m, 1H) 3.53 (dd, J=10.8, 35.1 Hz, 2H), 2.91 (s, 3H), 2.61 (m, 1H), 2.45 (m, 3H), 1.76 (m, 2H) 1.60 (m, 3H).

Example 64

N-(1-(Benzofuran-5-ylmethyl)piperidin-3-yl)-1H-indazol-5-amine, Compound 1.052

$^1$H NMR (CDCl$_3$, 300 MHz): δ 9.80 (bs, 1H), 7.84 (s, 1H), 7.56 (d, J=21.0 Hz, 1H), 7.44 (d, J=8.4 Hz, 1H), 7.29 (m, 4H) 6.81 (m, 3H), 3.60 (m, 3H), 2.80 (m, 1H), 2.42-2.30 (m, 3H), 1.75 (m, 2H) 1.58 (m, 3H).

Example 65

N-(1-((2,3-Dihydrobenzo[b][1,4]dioxin-6-yl)methyl)piperidin-3-yl)-1H-indazol-5-amine, Compound 1.053

$^1$H NMR (CDCl$_3$, 300 MHz): δ 9.75 (bs, 1H), 7.86 (s, 1H), 7.29 (m, 1H) 6.81 (m, 5H), 4.25 (s, 4H), 3.60 (bs, 1H), 3.40 (m, 2H), 2.74 (m, 1H), 2.42-2.30 (m, 3H), 1.75 (m, 2H) 1.58 (m, 3H).

Example 66

N-(1-(Benzo[b]thiophen-5-ylmethyl)piperidin-3-yl)-1H-indazol-5-amine, Compound 1.054

$^1$H NMR (CDCl$_3$, 300 MHz): δ 7.86 (s, 1H), 7.80 (m, 1H), 7.44-7.26 (m, 5H), 6.82 (m, 2H), 3.60 (m, 3H), 2.76 (m, 1H), 2.42-2.30 (m, 3H), 1.75 (m, 2H) 1.58 (m, 3H).

Example 67

3-((3-(1H-Indazol-5-ylamino)piperidin-1-yl)methyl)benzamide, Compound 1.055

$^1$H NMR (CDCl$_3$, 300 MHz): δ 7.85 (d, J=6.0 Hz, 2H), 7.65 (d, J=7.8 Hz, 1H), 7.49 (d, J=7.8 Hz, 1H), 7.38 (t, J=7.5 Hz, 1H), 7.27 (m, 1H), 6.83 (m, 2H), 6.15 (bs, 1H), 5.80 (bs, 1H), 3.60 (m, 1H) 3.56 (dd, J=13.5, 23.1 Hz, 2H), 2.75 (m, 1H), 2.45-2.25 (m, 3H), 1.71 (m, 2H) 1.56 (m, 3H).

Example 68

3-((3-(1H-Indazol-5-ylamino)piperidin-1-yl)methyl)benzenesulfonamide, Compound 1.056

$^1$H NMR (CDCl$_3$, 300 MHz): δ 7.84 (m, 2H), 7.65 (d, J=7.8 Hz, 1H), 7.49 (d, J=7.8 Hz, 1H), 7.38 (t, J=7.5 Hz, 1H), 7.27 (m, 1H), 6.83 (m, 2H), 6.10 (bs, 1H), 5.7 (bs, 1H), 3.60 (m, 1H) 3.56 (dd, J=13.5, 23.1 Hz, 2H), 2.75 (m, 1H), 2.45-2.25 (m, 3H), 1.71 (m, 2H) 1.56 (m, 3H).

Example 69 tert-Butyl 3-((3-(1H-Indazol-5-ylamino)piperidin-1-yl)methyl)benzylcarbamate, Compound 1.057

$^1$H NMR (CDCl$_3$, 300 MHz): δ 9.85 (bs, 1H), 7.86 (s, 1H), 7.39-7.26 (m, 7H), 6.82 (m, 2H), 4.80 (bs, 1H), 4.30 (d, J=5.4 Hz, 2H), 3.95 (bs, 1H), 3.68-3.4 (m, 3H), 2.74 (m, 1H), 2.45-2.35 (m, 3H), 1.76 (m, 2H), 1.60 (m, 2H), 1.46 (s, 9H).

Example 70

2-(5-((3-(1H-Indazol-5-ylamino)piperidin-1-yl)methyl)-2-methylphenoxy)ethanol, Compound 1.058

$^1$H NMR (CDCl$_3$, 300 MHz): δ 7.86 (s, 1H), 7.28 (d, J=8.7 Hz, 1H), 7.07 (d, J=7.5 Hz, 1H), 6.83 (m, 4H), 4.13 (m, 2H), 4.00 (m, 3H), 3.60 (m, 1H) 3.47 (dd, J=14.1, 27.3 Hz, 2H), 2.70 (m, 1H), 2.45-2.25 (m, 3H), 2.22 (s, 3H), 1.71 (m, 2H) 1.56 (m, 3H).

Example 71

5-((3-(1H-Indazol-5-ylamino)piperidin-1-yl)methyl)-2-methylphenol, Compound 1.059

$^1$H NMR (CD$_3$OD, 300 MHz): δ 7.78 (s, 1H), 7.31 (d, J=9.0 Hz, 1H), 6.97 (d, J=7.5 Hz, 1H), 6.90 (dd, J=2.1, 9.0 Hz, 1H), 6.85 (s, 1H), 6.74 (d, J=1.2 Hz, 1H), 6.66 (dd, J=1.2, 7.5 Hz, 1H), 3.48 (m, 1H), 3.44 (m, 2H), 3.00 (m, 1H), 2.70 (m, 1H), 2.14 (s, 3H), 2.13 (m, 1H), 1.97 (m, 2H), 1.80-1.60 (m, 2H), 1.3 (m, 1H).

Example 72

Ethyl 2-(3-((3-(1H-Indazol-5-ylamino)piperidin-1-yl)methyl)phenoxy)acetate, Compound 1.060

$^1$H NMR (CDCl$_3$, 300 MHz): δ 9.90 (bs, 1H), 7.85 (s, 1H), 7.35-7.26 (m, 2H), 6.95-6.82 (m, 5H), 4.60 (s, 2H), 4.25 (m, 2H), 3.60 (bs, 1H), 3.45 (m, 2H), 2.74 (m, 1H), 2.45-2.35 (m, 3H), 1.76 (m, 2H), 1.60 (m, 2H), 1.25 (m, 3H).

Example 73

N-(1-(3-(Aminomethyl)benzyl)piperidin-3-yl)-1H-indazol-5-amine, Compound 1.061

Prepared by deprotection of Compound 1.057 using the method of Example 4.

$^1$H NMR (CD$_3$OD, 300 MHz): δ 7.79 (s, 1H), 7.68 (d, J=8.7 Hz, 1H), 7.36 (d, J=9.0 Hz, 1H), 7.09 (m, 2H), 6.95 (m, 2H), 4.05 (m, 3H) 3.95 (m, 2H), 3.80 (m, 1H) 3.70 (m, 3H), 3.50 (m, 1H), 3.05 (m, 1H), 2.43-2.13 (m, 3H), 1.80-1.3 (m, 3H).

Example 74

N-(1-(3-(Trifluoromethyl)benzyl)piperidin-3-yl)-1H-indazol-5-amine, Compound 1.063

$^1$H NMR (CDCl$_3$, 300 MHz): δ 9.80 (bs, 1H), 7.86 (s, 1H), 7.85 (m, 2H), 7.53 (d, J=8.4 Hz, 2H), 7.30 (d, J=8.4 Hz, 1H), 6.84 (m, 2H), 3.60 (m, 3H), 2.76 (d, J=10.8 Hz, 1H), 2.43 (m, 3H), 1.75 (m, 2H) 1.59 (m, 3H).

Example 75

N-(1-(3-Ethoxybenzyl)piperidin-3-yl)-1H-indazol-5-amine, Compound 1.065

$^1$H NMR (CDCl$_3$, 300 MHz): δ 9.90 (bs, 1H), 7.86 (s, 1H), 7.30-7.18 (m, 2H), 6.90-6.76 (m, 5H), 4.03 (q, J=6.9 Hz, 2H) 3.60 (m, 1H) 3.44 (dd, J=13.2, 17.1 Hz, 2H), 2.76 (d, J=10.8 Hz, 1H), 2.43 (m, 3H), 2.35 (s, 3H), 1.75 (m, 2H) 1.59 (m, 3H), 1.42 (t, J=6.9 Hz, 3H).

Example 76

N-(1-(3-Methylbenzyl)piperidin-3-yl)-1H-indazol-5-amine, Compound 1.066

$^1$H NMR (CDCl$_3$, 300 MHz): δ 7.86 (s, 1H), 7.30-7.05 (m, 5H), 6.83 (m, 2H), 3.62 (m, 1H) 3.43 (m, 2H), 2.80 (m, 1H), 2.43 (m, 2H), 2.35 (s, 3H), 1.75 (m, 2H) 1.59 (m, 3H).

Example 77

N-(1-(2-Methoxybenzyl)piperidin-3-yl)-1H-indazol-5-amine, Compound 1.067

$^1$H NMR (CDCl$_3$, 300 MHz): δ 10.25 (bs, 1H), 7.86 (s, 1H), 7.37 (dd, J=1.5, 7.5 Hz, 1H), 7.24 (m, 2H), 6.93 (t, J=7.5 Hz, 1H), 6.80 (m, 3H), 3.80 (s, 3H), 3.60 (bs, 3H), 2.85 (m, 2H), 2.50-2.35 (m, 3H), 1.75 (m, 2H), 1.55 (m, 2H).

Example 78

5-((3-(1H-Indazol-5-ylamino)piperidin-1-yl)methyl)-2-iodophenol, Compound 1.068

$^1$H NMR (CDCl$_3$, 300 MHz): δ 7.86 (s, 1H), 7.63 (d, J=8.4 Hz, 1H), 7.26 (m, 2H), 6.93-6.80 (m, 3H), 6.50 (m, 1H), 3.62 (m, 1H) 3.43 (m, 2H), 2.60 (m, 3H), 2.4 (m, 1H), 1.71 (m, 2H) 1.56 (m, 3H).

Example 79

N-(1-(3-(4-Chlorophenoxy)benzyl)piperidin-3-yl)-1H-indazol-5-amine, Compound 1.069

$^1$H NMR (CDCl$_3$, 300 MHz): δ 9.8 (bs, 1H), 7.86 (s, 1H), 7.3-7.24 (m, 5H), 7.08 (d, J=7.5 Hz, 1H), 7.01 (s, 1H), 6.93 (dd, J=2.1, 6.6 Hz, 1H), 6.87 (dd, J=2.1, 6.6 Hz, 1H), 6.82 (m, 2H), 3.6 (m, 1H) 3.48 (dd, J=13.5, 18.9 Hz, 2H), 2.70 (m, 1H), 2.41-2.30 (m, 3H), 1.71 (m, 2H) 1.56 (m, 3H).

Example 80

N-(1-(3-(3-(Trifluoromethyl)phenoxy)benzyl)piperidin-3-yl)-1H-indazol-5-amine, Compound 1.070

$^1$H NMR (CDCl$_3$, 300 MHz): δ 9.8 (bs, 1H), 7.86 (s, 1H), 7.4-7.2 (m, 5H), 7.08 (m, 2H), 7.01 (s, 1H), 6.93 (m, 1H), 6.82 (m, 2H), 3.6 (m, 1H) 3.48 (m, 2H), 2.75 (m, 1H), 2.41-2.30 (m, 3H), 1.71 (m, 2H) 1.56 (m, 3H).

Example 81

N-(1-(2,5-Dibromobenzyl)piperidin-3-yl)-1H-indazol-5-amine, Compound 1.071

$^1$H NMR (CDCl$_3$, 300 MHz): δ 9.8 (bs, 1H), 7.86 (s, 1H), 7.62 (m, 1H), 7.4 (m, 1H), 7.2-7.05 (m, 2H), 6.82 (m, 2H), 3.65 (m, 1H) 3.48 (m, 2H), 2.80 (m, 1H), 2.5-2.30 (m, 3H), 1.71 (m, 2H) 1.56 (m, 3H).

Example 82

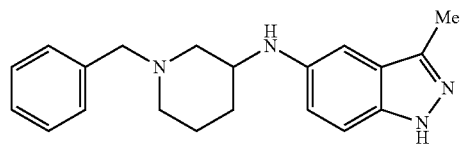 [SMILES: Cc1n[nH]c2ccc(NC3CCCN(Cc4ccccc4)C3)cc12]

N-(1-Benzylpiperidin-3-yl)-3-methyl-1H-indazol-5-amine, Compound 1.049

The title compound was prepared by reaction of 1-(5-amino-3-methyl-1H-indazol-1-yl)-2,2-dimethylpropan-1-one with tert-butyl 3-oxopiperidine-1-carboxylate using the method of Example 3, deprotection using the method of Example 4, reaction with benzaldehyde following the method of Example 8, and final deprotection using the method of Example 9.

$^1$H NMR (CDCl$_3$, 300 MHz): δ 7.4-7.18 (m, 6H), 6.80 (m, 2H), 6.70 (s, 1H), 3.6 (m, 1H), 3.45 (s, 2H), 2.74 (m, 1H), 2.50 (s, 3H), 2.40 (m, 2H), 2.30 (m, 1H), 1.75 (m, 2H) 1.56 (m, 2H).

Example 83

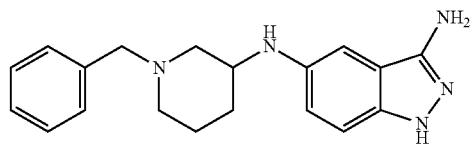 [SMILES: Nc1n[nH]c2ccc(NC3CCCN(Cc4ccccc4)C3)cc12]

$N^5$-(1-Benzylpiperidin-3-yl)-1H-indazole-3,5-diamine, Compound 1.050

Reaction of tert-butyl 3,5-diamino-1H-indazole-1-carboxylate with 1-benzylpiperidin-3-one using the method of Example 8, with the modification that sodium cyanoborohydride was used as the reductant and methanol was used as the solvent, followed by deprotection using the method of Example 4 afforded the title compound.

$^1$H NMR (CDCl$_3$, 300 MHz): δ 9.55 (bs, 1H), 7.3 (m, 5H), 7.10 (m, 1H), 6.80 (m, 1H), 6.60 (s, 1H), 3.90 (s, 2H), 3.6-3.4 (m, 3H), 2.80 (m, 1H), 2.47 (m, 3H), 2.41-2.30 (m, 3H), 1.75 (m, 2H) 1.56 (m, 3H).

Examples 84-89

Reaction of 2,2-dimethyl-1-(5-(pyrrolidin-3-ylamino)-1H-indazol-1-yl)propan-1-one with the appropriate aldehydes using the method of Example 8 followed by deprotection using the method of Example 9 afforded the compounds in Examples 84-89:

Example 84

N-(1-(4-(Methylsulfonyl)benzyl)pyrrolidin-3-yl)-1H-indazol-5-amine, Compound 1.004

$^1$H NMR (CDCl$_3$, 300 MHz): δ 9.80 (bs, 1H), 7.88 (m, 3H), 7.55 (d, J=8.1 Hz, 2H), 7.31 (d, J=8.7 Hz, 1H), 6.82 (dd, J=2.1, 8.7 Hz, 1H), 6.75 (d, J=2.1 Hz, 1H), 4.05 (m, 1H), 3.72 (m, 2H), 3.05 (s, 3H), 2.78 (m, 2H), 2.60 (dd, J=3.3, 9.6 Hz, 1H), 2.45-2.35 (m, 2H), 1.75 (m, 1H).

Example 85

3-((3-(1H-Indazol-5-ylamino)pyrrolidin-1-yl)methyl)benzonitrile, Compound 1.005

$^1$H NMR (CDCl$_3$, 300 MHz): δ 10.7 (bs, 1H), 7.9 (s, 1H), 7.65 (s, 1H), 7.55 (m, 2H), 7.40 (m, 2H), 7.28 (m, 1H) 6.84 (m, 2H), 4.05 (bs, 1), 3.65 (s, 2H), 2.8 (m, 2H), 2.65 (m, 1H) 2.45-2.25 (m, 2H), 1.75 (m, 2H).

Example 86

N-(4-((3-(1H-Indazol-5-ylamino)pyrrolidin-1-yl)methyl)phenyl)acetamide, Compound 1.006

$^1$H NMR (CDCl$_3$, 300 MHz): δ 7.88 (s, 1H), 7.43 (d, J=8.4 Hz, 2H), 7.24 (m, 3H), 7.18 (bs, 1H), 6.77 (m, 2H), 4.01 (m, 1H), 3.60 (m, 2H), 2.78 (m, 2H), 2.60 (dd, J=3.3, 9.6 Hz, 1H), 2.45-2.35 (m, 2H), 2.16 (s, 6H), 1.75 (m, 1H).

Example 87

N-(1-(4-(3-(Dimethylamino)propoxy)benzyl)pyrrolidin-3-yl)-1H-indazol-5-amine, Compound 1.007

$^1$H NMR (CDCl$_3$, 300 MHz): δ 10.45 (bs, 1H), 7.88 (s, 1H), 7.23 (m, 3H), 6.85-6.73 (m, 4H), 3.99 (t, J=6.3 Hz, 3H), 3.57 (m, 2H), 2.78 (m, 2H), 2.60 (m, 1H) 2.45 (t, J=7.5 Hz, 4H), 2.26 (s, 6H), 1.95 (m, 2H), 1.75 (m, 1H).

Example 88

N-(1-(3,4-Dichlorobenzyl)pyrrolidin-3-yl)-1H-indazol-5-amine, Compound 1.062

¹H NMR (CDCl₃, 300 MHz): δ 9.80 (bs, 1H), 7.86 (s, 1H), 7.40-7.20 (m, 3H), 6.84 (m, 3H), 4.05 (bs, 1), 3.60 (s, 2H), 2.8 (m, 2H), 2.60 (m, 1H) 2.45-2.25 (m, 2H), 1.75 (m, 2H).

Example 89

N-(1-(3-(Trifluoromethyl)benzyl)pyrrolidin-3-yl)-1H-indazol-5-amine, Compound 1.064

Examples 90-92

Reaction of (R)—N-(piperidin-3-yl)-1H-indazol-5-amine with the appropriate aldehydes using the method of Example 8 and using THF as the reaction solvent afforded the compounds in Examples 90-92:

Example 90

(R)—N-(1-(3,4-Difluorobenzyl)piperidin-3-yl)-1H-indazol-5-amine, Compound 1.073

¹H NMR (CDCl₃, 300 MHz): δ 7.87 (s, 1H), 7.29 (d, J=9.3 Hz, 1H), 7.23-7.04 (m, 3H), 6.83 (m, 2H), 3.63 (m, 1H), 3.49 (m, 2H), 2.75 (m, 1H), 2.45-2.25 (m, 3H), 1.80-1.50 (m, 5H).

Example 91

(R)—N-(1-(4-(Methylthio)benzyl)piperidin-3-yl)-1H-indazol-5-amine, Compound 1.074

¹H NMR (CDCl₃, 300 MHz): δ 9.8 (bs, 1H), 7.86 (s, 1H), 7.3-7.18 (m, 5H), 6.82 (m, 2H), 3.6-3.4 (m, 3H), 2.74 (m, 1H), 2.47 (s, 3H), 2.41-2.30 (m, 3H), 1.75 (m, 2H) 1.56 (m, 3H).

Example 92

(R)—N-(1-(4-Ethynylbenzyl)piperidin-3-yl)-1H-indazol-5-amine, Compound 1.076

¹H NMR (CDCl₃, 300 MHz): δ 7.86 (s, 1H), 7.43 (d, J=8.4 Hz, 2H), 7.26 (m, 3H), 6.84 (m, 2H), 3.60 (bs, 1H), 3.49 (dd, J=5.4, 9.1 Hz, 2H), 3.05 (s, 1H), 2.74 (m, 1H), 2.41-2.30 (m, 3H), 1.75 (m, 2H) 1.56 (m, 3H).

Examples 93-98

Reaction of (S)—N-(piperidin-3-yl)-1H-indazol-5-amine with the appropriate aldehydes using the method of Example 8 and using THF as the reaction solvent afforded the compounds in Examples 93-98:

Example 93

(S)—N-(1-(3,4-Difluorobenzyl)piperidin-3-yl)-1H-indazol-5-amine, Compound 1.072

¹H NMR (CDCl₃, 300 MHz): δ 7.87 (s, 1H), 7.29 (d, J=9.3 Hz, 1H), 7.23-7.04 (m, 3H), 6.83 (m, 2H), 3.63 (m, 1H), 3.49 (m, 2H), 2.75 (m, 1H), 2.45-2.25 (m, 3H), 1.80-1.50 (m, 5H).

Example 94

(S)—N-(1-(4-Ethynylbenzyl)piperidin-3-yl)-1H-indazol-5-amine, Compound 1.077

¹H NMR (CDCl₃, 300 MHz): δ 7.86 (s, 1H), 7.43 (d, J=8.4 Hz, 2H), 7.26 (m, 3H), 6.84 (m, 2H), 3.60 (bs, 1H), 3.49 (dd, J=5.4, 9.1 Hz, 2H), 3.05 (s, 1H), 2.74 (m, 1H), 2.41-2.30 (m, 3H), 1.75 (m, 2H) 1.56 (m, 3H).

Example 95

(S)—N-(1-(4-Methylbenzyl)piperidin-3-yl)-1H-indazol-5-amine, Compound 1.078

¹H NMR (CDCl₃, 300 MHz): δ 7.86 (s, 1H), 7.28 (d, J=8.7 Hz, 1H), 7.21 (d, J=8.1 Hz, 2H), 7.11 (d, J=8.1 Hz, 2H), 6.84 (m, 2H), 4.40 (bs, 1H), 3.60 (bs, 1H), 3.49 (dd, J=13.2, 21.0 Hz, 2H), 2.74 (m, 1H), 2.41 (m, 3H), 2.39 (s, 3H), 1.75 (m, 2H) 1.56 (m, 3H).

Example 96

(S)—N-(1-(4-Methoxybenzyl)piperidin-3-yl)-1H-indazol-5-amine, Compound 1.079

¹H NMR (CDCl₃, 300 MHz): δ 7.86 (s, 1H), 7.30-7.20 (m, 5H), 6.91-6.80 (m, 4H), 3.80 (s, 3H), 3.60-3.40 (m, 3H), 2.80 (s, 1H), 2.50-2.30 (m, 3H), 1.80-1.40 (m, 5H).

Example 97

(S)—N-(1-(3,4-Dichlorobenzyl)piperidin-3-yl)-1H-indazol-5-amine, Compound 1.080

¹H NMR (CDCl₃, 300 MHz): δ 10.0 (bs, 1H), 7.87 (s, 1H), 7.45 (s, 1H), 7.36 (d, J=8.1 Hz, 1H), 7.29 (d, J=8.7 Hz, 1H), 7.15 (dd, J=2.1, 8.1 Hz, 1H), 6.82 (m, 2H), 3.60 (m, 1H), 3.45 (dd, J=13.8, 18 Hz, 2H), 2.75 (d, J=10.2 Hz, 1H), 2.45-2.25 (m, 3H), 1.80-1.50 (m, 5H).

Example 98

(S)—N-(1-(4-Chlorobenzyl)piperidin-3-yl)-1H-indazol-5-amine, Compound 1.081

¹H NMR (CDCl₃, 300 MHz): δ 7.86 (s, 1H), 7.3-7.18 (m, 5H), 6.82 (m, 2H), 3.6-3.4 (m, 3H), 2.74 (m, 1H), 2.40 (m, 3H), 2.41-2.30 (m, 3H), 1.75 (m, 2H) 1.56 (m, 3H).

Example 99

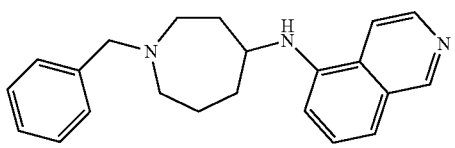 [SMILES: c1ccc(CN2CCCC(Nc3cccc4cnccc34)CC2)cc1]

N-(1-Benzylazepan-4-yl)isoquinolin-5-amine, Compound 2.013

The title compound was prepared by reaction of isoquinolin-5-amine with tert-butyl 4-oxoazepane-1-carboxylate using the method of Example 3, followed by deprotection using the method of Example 4 and reaction with benzaldehyde following the method of Example 8.

$^1$H NMR (CDCl$_3$, 300 MHz): δ 9.14 (s, 1H), 8.45 (d, J=6 Hz, 1H), 7.57 (d, J=6 Hz, 1H), 7.46-7.25 (m, 7H), 6.72 (d, J=7.5 Hz, 1H), 4.0 (m, 1H), 3.71 (m, 2H), 2.92 (m, 1H), 2.80 (m, 1H), 2.7-2.6 (m, 2H), 2.05-1.87 (m, 7H).

Examples 100-109

Reaction of N-(piperidin-3-yl)isoquinolin-5-amine with the appropriate aldehydes using the method of Example 8 afforded the compounds in Examples 100-109:

Example 100

N-(1-(4-Methoxybenzyl)piperidin-3-yl)isoquinolin-5-amine, Compound 2.001

$^1$H NMR (CDCl$_3$, 300 MHz): δ 9.15 (s, 1H), 8.49 (d, J=6.0 Hz, 1H), 7.55 (m, 1H), 7.41 (t, J=7.8 Hz, 1H), 7.30 (m, 3H), 6.88 (m, 2H), 6.73 (d, J=6.6 Hz, 1H), 5.05 (bs, 1H), 3.81 (bs, 4H), 3.63 (m, 2H), 3.09 (s, 3H), 2.65 (m, 3H), 2.35 (m, 1H), 1.85-1.60 (m, 4H).

Example 101

N-(1-(4-(Methylsulfonyl)benzyl)piperidin-3-yl)isoquinolin-5-amine, Compound 2.002

$^1$H NMR (CDCl$_3$, 300 MHz): δ 9.15 (s, 1H), 8.49 (d, J=6.0 Hz, 1H), 7.89 (d, J=8.1 Hz, 2H), 7.55 (m, 3H), 7.41 (t, J=7.8 Hz, 1H), 7.27 (d, J=6.9 Hz, 1H), 6.73 (d, J=6.6 Hz, 1H), 4.88 (bs, 1H), 3.81 (bs, 1H), 3.63 (dd, J=10.8, 22.5 Hz, 2H), 3.09 (s, 3H), 2.74 (d, J=10.2 Hz, 1H), 2.45 (m, 3H), 1.85-1.60 (m, 4H).

Example 102

3-((3-(Isoquinolin-5-ylamino)piperidin-1-yl)methyl)benzonitrile, Compound 2.003

$^1$H NMR (CDCl$_3$, 300 MHz): δ 9.10 (s, 1H), 8.46 (d, J=6.0 Hz, 1H), 7.69 (s, 1H), 7.55 (m, 3H), 7.45 (m, 2H), 7.24 (m, 1H), 6.73 (d, J=7.5 Hz, 1H), 4.88 (bs, 1H), 4.78 (s, 2H), 3.78 (bs, 1H), 3.55 (dd, J=13.5, 22.5 Hz, 2H), 2.74 (d, J=10.2 Hz, 1H), 2.45 (m, 3H), 1.85-1.60 (m, 4H).

Example 103

N-(4-((3-(Isoquinolin-5-ylamino)piperidin-1-yl)methyl)phenyl)acetamide, Compound 2.004

$^1$H NMR (CDCl$_3$, 300 MHz): δ 9.13 (s, 1H), 8.48 (d, J=6.0 Hz, 1H), 7.55 (d, J=6 Hz, 1H), 7.48-7.38 (m, 3H), 7.31 (d, J=8.4 Hz, 2H), 7.24 (d, J=8.4 Hz, 1H), 6.72 (d, J=7.5 Hz, 1H), 5.05 (bs, 1), 3.78 (bs, 1H), 3.51 (m, 2H), 2.70-2.30 (m, 4H), 2.16 (s, 3H), 1.85-1.60 (m, 4H).

Example 104

N-(1-(4-(Methylthio)benzyl)piperidin-3-yl)isoquinolin-5-amine, Compound 2.009

$^1$H NMR (CDCl$_3$, 300 MHz): δ 9.14 (s, 1H), 8.49 (d, J=6 Hz, 1H), 7.55 (d, J=6 Hz, 1H), 7.41 (t, J=7.5 Hz, 1H), 7.27 (m, 5H), 6.72 (d, J=7.5 Hz, 1H), 5.00 (bs, 1H), 3.78 (bs, 1H), 3.51, (dd, J=12, 30 Hz, 2H), 2.70-2.55 (m, 3H), 2.47 (s, 3H), 2.35 (m, 1H), 1.80-1.50 (m, 4H).

Example 105

N-(1-(4-Cyclopropylbenzyl)piperidin-3-yl)isoquinolin-5-amine, Compound 2.010

$^1$H NMR (CDCl$_3$, 300 MHz): δ 9.15 (s, 1H), 8.50 (d, J=6 Hz, 1H), 7.56 (d, J=4.8 Hz, 1H), 7.45 (t, J=7.5 Hz, 1H), 7.27 (m, 4H) 7.05 (d, J=7.5 Hz, 1H), 6.73 (d, J=6 Hz, 1H), 5.06 (bs, 1H), 3.78 (bs, 1H), 3.54, (m, 2H), 2.61 (m, 3H), 2.35 (m, 1H), 1.94-1.50 (m, 6H), 1.27 (m, 3H), 1.00-0.80 (m, 3H), 0.90 (m, 1H), 0.69 (m, 2H).

Example 106

N-(1-(3-Cyclopropylbenzyl)piperidin-3-yl)isoquinolin-5-amine, Compound 2.011

$^1$H NMR (CDCl$_3$, 300 MHz): δ 9.15 (s, 1H), 8.50 (d, J=6 Hz, 1H), 7.59 (bs, 1H), 7.43 (t, J=7.5 Hz, 1H), 7.27-7.10 (m, 5H) 6.99 (m, 1H), 6.73 (d, J=7.5 Hz, 1H), 5.06 (bs, 1H), 3.81 (bs, 1H), 3.54, (m, 2H), 2.64 (m, 3H), 2.40 (m, 1H), 1.94-1.50 (m, 6H), 1.27 (m, 3H), 1.00 (m, 2H), 0.90 (m, 1H), 0.72 (m, 2H).

Example 107

N-(1-(4-(Cyclopropylthio)benzyl)piperidin-3-yl)isoquinolin-5-amine, Compound 2.012

$^1$H NMR (CDCl$_3$, 300 MHz): δ 9.14 (s, 1H), 8.50 (d, J=6 Hz, 1H), 7.59 (bs, 1H), 7.46-7.25 (m, 7H), 6.73 (d, J=7.5 Hz, 1H), 5.06 (bs, 1H), 3.71 (m, 1H), 3.55, (dd, J=12, 30 Hz, 2H), 2.7-2.5 (m, 3H), 2.40 (m, 1H), 2.20 (m, 1H), 1.80-1.50 (m, 5H), 1.07 (d, J=6 Hz, 2H), 0.70 (s, 2H).

Example 108

N-(1-(3,4-Dichlorobenzyl)piperidin-3-yl)isoquinolin-5-amine, Compound 2.014

$^1$H NMR (CDCl$_3$, 300 MHz): δ 9.15 (s, 1H), 8.49 (d, J=6.0 Hz, 1H), 7.55 (d, J=6 Hz, 1H), 7.51 (d, J=1.8 Hz, 1H), 7.45-7.36 (m, 2H), 7.24 (m, 1H), 7.17 (dd, J=1.8, 8.1 Hz, 1H), 6.72 (d, J=7.5 Hz, 1H), 4.95 (bs, 1), 3.78 (bs, 1H), 3.49 (dd, J=13.5, 32.4 Hz, 2H), 2.70-2.30 (m, 4H), 1.85-1.60 (m, 4H).

Example 109

N-(1-(3-(Trifluoromethyl)benzyl)piperidin-3-yl)isoquinolin-5-amine, Compound 2.015

$^1$H NMR (CDCl$_3$, 300 MHz): δ 9.14 (s, 1H), 8.48 (d, J=6.0 Hz, 1H), 7.71 (s, 1H), 7.47-7.31 (m, 5H), 7.24 (dd, J=6.0 Hz, 1H), 6.71 (d, J=7.8 Hz, 1H), 5.0 (bs, 1), 3.80 (bs, 1H), 3.60 (dd, J=13.5, 29.7 Hz, 2H), 2.70-2.30 (m, 4H), 1.85-1.60 (m, 4H).

Examples 110-116

Reaction of N-(pyrrolidin-3-yl)isoquinolin-5-amine with the appropriate aldehydes using the method of Example 8 afforded the compounds in Examples 110-116:

Example 110

N-(1-(4-(Methylsulfonyl)benzyl)pyrrolidin-3-yl)
isoquinolin-5-amine, Compound 2.005

$^1$H NMR (CDCl$_3$, 300 MHz): δ 9.16 (s, 1H), 8.49 (d, J=6.3 Hz, 1H), 7.90 (d, J=8.4 Hz, 2H), 7.56 (d, J=8.4 Hz, 3H), 7.42 (t, J=7.8 Hz, 1H), 7.33 (d, J=8.1 Hz, 1H), 6.69 (d, J=7.5 Hz, 1H), 4.58 (m, 1H), 4.19 (m, 1H), 3.76 (s, 2H), 3.05 (s, 3H), 2.88 (m, 2H), 2.70 (dd, J=3.3, 9.6 Hz, 1H) 2.60-2.40 (m, 2H), 1.85 (m, 1H).

Example 111

N-(1-Benzylpyrrolidin-3-yl)isoquinolin-5-amine,
Compound 2.006

$^1$H NMR (CDCl$_3$, 300 MHz): δ 9.14 (s, 1H), 8.46 (d, J=6.3 Hz, 1H), 7.56 (d, J=6.3 Hz, 1H), 7.43 (t, J=8.1 Hz, 1H), 7.30 (m, 7H), 6.69 (d, J=7.5 Hz, 1H), 4.65 (m, 1H), 4.18 (m, 1H), 3.68 (m, 2H), 2.87 (m, 2H), 2.70 (dd, J=3.3, 9.6 Hz, 1H) 2.60-2.40 (m, 2H), 1.85 (m, 1H).

Example 112

3-((3-(Isoquinolin-5-ylamino)pyrrolidin-1-yl)methyl)benzonitrile, Compound 2.007

$^1$H NMR (CDCl$_3$, 300 MHz): δ 9.15 (s, 1H), 8.48 (d, J=6.0 Hz, 1H), 7.66 (s, 1H), 7.55 (m, 3H), 7.43 (dd, J=7.5, 10.8 Hz, 2H), 7.32 (d, J=8.1 Hz, 1H), 6.70 (d, J=7.5 Hz, 1H), 4.57 (d, J=6.6 Hz, 1H), 4.18 (m, 1H), 3.68 (m, 2H), 2.87 (m, 2H), 2.70 (dd, J=3.3, 9.6 Hz, 1H) 2.60-2.40 (m, 2H), 1.85 (m, 1H).

Example 113

N-(4-((3-(Isoquinolin-5-ylamino)pyrrolidin-1-yl)
methyl)phenyl)acetamide, Compound 2.008

$^1$H NMR (CDCl$_3$, 300 MHz): δ 9.14 (s, 1H), 8.45 (d, J=6.0 Hz, 1H), 7.57 (m, 2H), 7.47-7.27 (m, 5H), 6.68 (d, J=7.5 Hz, 1H), 4.66 (m, 1H), 4.14 (bs, 1H), 3.63 (s, 2H), 3.47 (bs, 1H), 2.83 (m, 2H), 2.70 (m, 1H) 2.60-2.40 (m, 2H), 2.15 (s, 3H), 1.85 (m, 1H).

Example 114

N-(1-(3,4-Dichlorobenzyl)pyrrolidin-3-yl)isoquinolin-5-amine, Compound 2.016

$^1$H NMR (CDCl$_3$, 300 MHz): δ 9.16 (s, 1H), 8.48 (d, J=6.0 Hz, 1H), 7.56 (d, J=6.0 Hz, 1H), 7.47-7.31 (m, 3H), 7.18 (dd, J=3.6, 8.1 Hz, 1H), 6.68 (d, J=7.5 Hz, 1H), 4.60 (bs, 1H), 4.18 (m, 1H), 3.62 (s, 2H), 2.87 (m, 2H), 2.70 (m, 1H) 2.60-2.40 (m, 2H), 1.85 (m, 1H).

Example 115

N-(1-(4-Methoxybenzyl)pyrrolidin-3-yl)isoquinolin-5-amine, Compound 2.017

$^1$H NMR (CDCl$_3$, 300 MHz): δ 9.15 (s, 1H), 8.47 (d, J=6.0 Hz, 1H), 7.56 (d, J=6.0 Hz, 1H), 7.43 (t, J=7.8 Hz, 1H), 7.24 (m, 3H), 6.87 (d, J=8.7 Hz, 2H), 6.68 (d, J=8.4 Hz, 1H), 4.63 (bs, 1), 4.20 (m, 1H), 3.81 (s, 3H), 3.64 (s, 2H), 2.87 (m, 2H), 2.70 (m, 1H) 2.60-2.40 (m, 2H), 1.85 (m, 1H).

Example 116

N-(1-(3-(Trifluoromethyl)benzyl)pyrrolidin-3-yl)
isoquinolin-5-amine, Compound 2.018

$^1$H NMR (CDCl$_3$, 300 MHz): δ 9.15 (s, 1H), 8.47 (d, J=6.0 Hz, 1H), 7.62 (s, 1H), 7.56 (m, 3H), 7.45 (m, 2H), 7.31 (d, J=8.4 Hz, 1H), 6.70 (d, J=7.8 Hz, 1H), 4.62 (d, J=6.9 Hz, 1H), 4.16 (m, 1H), 3.71 (s, 2H), 2.88 (m, 2H), 2.70 (dd, J=3.3, 9.6 Hz, 1H) 2.60-2.40 (m, 2H), 1.85 (m, 1H).

Examples 117-122

Reaction of (R)—N-(pyrrolidin-3-yl)isoquinolin-5-amine with the appropriate aldehydes using the method of Example 8 afforded the compounds in Examples 117-122:

Example 117

(R)—N-(1-(3-Cyclopropylbenzyl)pyrrolidin-3-yl)
isoquinolin-5-amine, Compound 2.020

$^1$H NMR (CDCl$_3$, 300 MHz): δ 9.14 (s, 1H), 8.46 (d, J=6.0 Hz, 1H), 7.56 (d, J=6 Hz, 1H), 7.43 (t, J=8.1, 1H), 7.31-7.23 (m, 5H), 6.69 (d, J=7.8 Hz, 1H), 4.69 (d, J=6.3 Hz, 1H), 4.18 (m, 1H), 3.65 (s, 2H), 2.88 (m, 2H), 2.71 (dd, J=3.6, 9.6 Hz, 1H), 2.60-2.40 (m, 2H), 2.18 (m, 1H), 1.85 (m, 2H), 1.04 (m, 2H), 0.69 (m, 2H).

Example 118

(R)—N-(1-(4-(Cyclopropylthio)benzyl)pyrrolidin-3-yl)isoquinolin-5-amine, Compound 2.021

$^1$H NMR (CDCl$_3$, 300 MHz): δ 9.16 (s, 1H), 8.48 (d, J=6.0 Hz, 1H), 7.60 (d, J=6 Hz, 1H), 7.44 (t, J=8.1, 1H), 7.32 (d, J=8.1 Hz, 1H), 7.23 (m, 2H), 7.10, (m, 2H), 6.69 (d, J=7.5 Hz, 1H), 4.75 (d, J=6.6 Hz, 1H), 4.18 (m, 1H), 3.68 (m, 2H), 2.88 (m, 2H), 2.71 (dd, J=3.6, 9.6 Hz, 1H), 2.60-2.40 (m, 2H), 1.85 (m, 2H), 0.95 (m, 2H), 0.70 (m, 2H).

Example 119

(R)—N-(1-(4-Cyclopropylbenzyl)pyrrolidin-3-yl)
isoquinolin-5-amine, Compound 2.022

$^1$H NMR (CDCl$_3$, 300 MHz): δ 9.15 (s, 1H), 8.48 (d, J=6.0 Hz, 1H), 7.62 (d, J=6 Hz, 1H), 7.43 (t, J=7.8, 1H), 7.31 (d, J=8.1 Hz, 1H), 7.23 (m, 2H), 7.05 (m, 2H), 6.67 (d, J=7.5 Hz, 1H), 4.88 (bs, 1H), 4.21 (m, 1H), 3.73 (m, 2H), 3.05-2.80 (m, 3H), 2.65-2.40 (m, 2H), 1.88 (m, 2H), 0.97 (m, 2H), 0.69 (m, 2H).

Example 120

(R)—N-(1-(4-Methylbenzyl)pyrrolidin-3-yl)isoquinolin-5-amine, Compound 2.025

$^1$H NMR (CDCl$_3$, 300 MHz): δ 9.14 (s, 1H), 8.46 (d, J=6.0 Hz, 1H), 7.59 (d, J=6 Hz, 1H), 7.43 (t, J=7.8 Hz, 1H), 7.31 (d, J=8.1 Hz, 1H), 7.23 (d, J=8.1 Hz, 2H), 7.14, (d, J=8.1 Hz, 2H), 6.68 (d, J=7.5 Hz, 1H), 4.75 (m, 1H), 4.18 (m, 1H), 3.68 (s,

2H), 2.88 (m, 2H), 2.71 (dd, J=3.6, 9.6 Hz, 1H), 2.60-2.40 (m, 2H), 2.33 (s, 3H), 2.05 (bs, 1H), 1.85 (m, 1H).

Example 121

(R)—N-(1-(4-Chlorobenzyl)pyrrolidin-3-yl)isoquinolin-5-amine, Compound 2.027

¹H NMR (CDCl₃, 300 MHz): δ 9.13 (s, 1H), 8.46 (d, J=6.0 Hz, 1H), 7.60 (d, J=6 Hz, 1H), 7.43 (t, J=8.1 Hz, 1H), 7.31 (m, 5H), 6.68 (d, J=7.5 Hz, 1H), 4.80 (bs, 1H), 4.20 (m, 1H), 3.69 (s, 2H), 2.88 (m, 2H), 2.80 (m, 1H) 2.60-2.40 (m, 2H), 1.85 (m, 1H).

Example 122

(R)—N-(1-(4-Ethynylbenzyl)pyrrolidin-3-yl)isoquinolin-5-amine, Compound 2.031

¹H NMR (CDCl₃, 300 MHz): δ 9.15 (s, 1H), 8.47 (d, J=6.0 Hz, 1H), 7.58 (d, J=6 Hz, 1H), 7.45 (m, 3H), 7.31 (m, 3H), 6.68 (d, J=7.8 Hz, 1H), 4.70 (bs, 1H), 4.17 (m, 1H), 3.67 (s, 2H), 3.06 (s, 1H), 2.88 (m, 2H), 2.70 (dd, J=3.3, 9.9 Hz, 1H) 2.60-2.40 (m, 2H), 1.85 (m, 1H).

Examples 123-128

Reaction of (S)—N-(pyrrolidin-3-yl)isoquinolin-5-amine with the appropriate aldehydes using the method of Example 8 afforded the compounds in Examples 123-128:

Example 123

(S)—N-(1-(4-Cyclopropylbenzyl)pyrrolidin-3-yl)isoquinolin-5-amine, Compound 2.019

¹H NMR (CDCl₃, 300 MHz): δ 9.15 (s, 1H), 8.48 (d, J=6.0 Hz, 1H), 7.62 (d, J=6 Hz, 1H), 7.43 (t, J=7.8, 1H), 7.31 (d, J=8.1 Hz, 1H), 7.23 (m, 2H), 7.05 (m, 2H), 6.67 (d, J=7.5 Hz, 1H), 4.88 (bs, 1H), 4.21 (m, 1H), 3.73 (m, 2H), 3.05-2.80 (m, 3H), 2.65-2.40 (m, 2H), 1.88 (m, 2H), 0.97 (m, 2H), 0.69 (m, 2H).

Example 124

(S)—N-(1-(3-Cyclopropylbenzyl)pyrrolidin-3-yl)isoquinolin-5-amine, Compound 2.023

¹H NMR (CDCl₃, 300 MHz): δ 9.14 (s, 1H), 8.46 (d, J=6.0 Hz, 1H), 7.56 (d, J=6 Hz, 1H), 7.43 (t, J=8.1, 1H), 7.31-7.23 (m, 5H), 6.69 (d, J=7.8 Hz, 1H), 4.69 (d, J=6.3 Hz, 1H), 4.18 (m, 1H), 3.65 (s, 2H), 2.88 (m, 2H), 2.71 (dd, J=3.6, 9.6 Hz, 1H), 2.60-2.40 (m, 2H), 2.18 (m, 1H), 1.85 (m, 2H), 1.04 (m, 2H), 0.69 (m, 2H).

Example 125

(S)—N-(1-(4-(Cyclopropylthio)benzyl)pyrrolidin-3-yl)isoquinolin-5-amine, Compound 2.024

¹H NMR (CDCl₃, 300 MHz): δ 9.16 (s, 1H), 8.48 (d, J=6.0 Hz, 1H), 7.60 (d, J=6 Hz, 1H), 7.44 (t, J=8.1, 1H), 7.32 (d, J=8.1 Hz, 1H), 7.23 (m, 2H), 7.10, (m, 2H), 6.69 (d, J=7.5 Hz, 1H), 4.75 (d, J=6.6 Hz, 1H), 4.18 (m, 1H), 3.68 (m, 2H), 2.88 (m, 2H), 2.71 (dd, J=3.6, 9.6 Hz, 1H), 2.60-2.40 (m, 2H), 1.85 (m, 2H), 0.95 (m, 2H), 0.70 (m, 2H).

Example 126

(S)—N-(1-(4-Methylbenzyl)pyrrolidin-3-yl)isoquinolin-5-amine, Compound 2.028

¹H NMR (CDCl₃, 300 MHz): δ 9.14 (s, 1H), 8.46 (d, J=6.0 Hz, 1H), 7.59 (d, J=6 Hz, 1H), 7.43 (t, J=7.8 Hz, 1H), 7.31 (d, J=8.1 Hz, 1H), 7.23 (d, J=8.1 Hz, 2H), 7.14, (d, J=8.1 Hz, 2H), 6.68 (d, J=7.5 Hz, 1H), 4.75 (m, 1H), 4.18 (m, 1H), 3.68 (s, 2H), 2.88 (m, 2H), 2.71 (dd, J=3.6, 9.6 Hz, 1H), 2.60-2.40 (m, 2H), 2.33 (s, 3H), 2.05 (bs, 1H), 1.85 (m, 1H).

Example 127

(S)—N-(1-(4-(Methylthio)benzyl)pyrrolidin-3-yl)isoquinolin-5-amine, Compound 2.029

¹H NMR (CDCl₃, 300 MHz): δ 9.14 (s, 1H), 8.46 (d, J=6.0 Hz, 1H), 7.56 (d, J=6 Hz, 1H), 7.43 (t, J=7.8 Hz, 1H), 7.31 (m, 5H), 6.68 (d, J=7.5 Hz, 1H), 4.66 (d, J=7.2 Hz, 1H), 4.18 (m, 1H), 3.64 (s, 2H), 2.88 (m, 2H), 2.71 (dd, J=3.6, 9.6 Hz, 1H), 2.60-2.40 (m, 2H), 2.47 (s, 3H), 2.05 (bs, 1H), 1.85 (m, 1H).

Example 128

(S)—N-(1-(4-Chlorobenzyl)pyrrolidin-3-yl)isoquinolin-5-amine, Compound 2.030

¹H NMR (CDCl₃, 300 MHz): δ 9.13 (s, 1H), 8.46 (d, J=6.0 Hz, 1H), 7.60 (d, J=6 Hz, 1H), 7.43 (t, J=8.1 Hz, 1H), 7.31 (m, 5H), 6.68 (d, J=7.5 Hz, 1H), 4.80 (bs, 1H), 4.20 (m, 1H), 3.69 (s, 2H), 2.88 (m, 2H), 2.80 (m, 1H) 2.60-2.40 (m, 2H), 1.85 (m, 1H).

Example 129

Prophetic Example

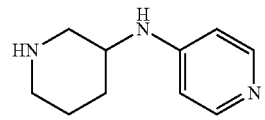 [SMILES: c1cc(NC2CCCNC2)ccn1]

N-(Piperidin-3-yl)pyridin-4-amine

Reaction of tert-butyl 3-oxopiperidine-1-carboxylate and 4-aminopyridine using the method of Example 3 followed by deprotection using the method of Example 4 affords the title compound.

Example 130

Prophetic Example

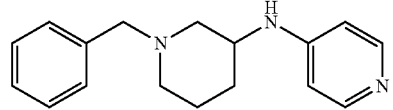 [SMILES: c1ccc(CN2CCCC(Nc3ccncc3)C2)cc1]

N-(1-Benzylpiperidin-3-yl)pyridin-4-amine, Compound 3.001

Reaction of N-(piperidin-3-yl)pyridin-4-amine with the benzaldehyde using the method of Example 8 affords the title compound.

Example 131

Prophetic Example

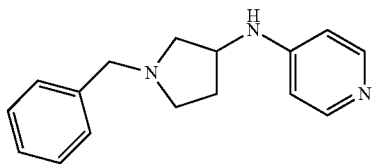 [SMILES: c1ccc(CN2CCC(Nc3ccncc3)C2)cc1]

N-(1-Benzylpyrrolidin-3-yl)pyridin-4-amine, Compound 3.002

Reaction of tert-butyl 3-oxopyrrolidine-1-carboxylate and 4-aminopyridine using the method of Example 3 followed by deprotection using the method of Example 4 affords the intermediate pyrrolidine, which is reacted with benzaldehyde following the method of Example 8 to give the title compound.

Example 132

Prophetic Example

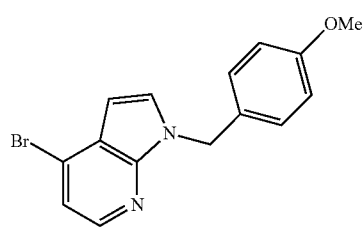 [SMILES: COc1ccc(Cn2ccc3c(Br)ccnc32)cc1]

4-Bromo-1-(4-methoxybenzyl)-1H-pyrrolo[2,3-b]pyridine

Reaction of 4-bromo-1H-pyrrolo[2,3-b]pyridine with 4-methoxybenzyl chloride following the method of Example 12 affords the title compound.

Example 133

Prophetic Example

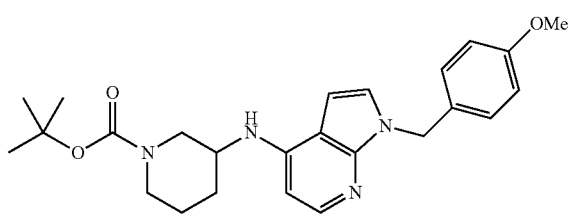 [SMILES: COc1ccc(Cn2ccc3c(NC4CCCN(C(=O)OC(C)(C)C)C4)ccnc32)cc1]

tert-Butyl 3-(1-(4-Methoxybenzyl)-1H-pyrrolo[2,3-b]pyridin-4-ylamino)piperidine-1-carboxylate Reaction of 4-bromo-1-(4-methoxybenzyl)-1H-pyrrolo[2,3-b]pyridine with tert-butyl 3-aminopiperidine-1-carboxylate following the method of Example 13 affords the title compound.

Example 134

Prophetic Example

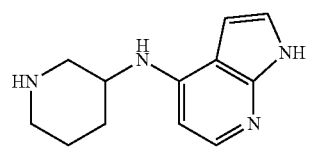 [SMILES: c1cc(NC2CCCNC2)c2cc[nH]c2n1]

N-(Piperidin-3-yl)-1H-pyrrolo[2,3-b]pyridin-4-amine

Deprotection of tert-butyl 3-(1-(4-methoxybenzyl)-1H-pyrrolo[2,3-b]pyridin-4-ylamino)piperidine-1-carboxylate using the method of Example 14 affords the title compound.

Example 135

Prophetic Example

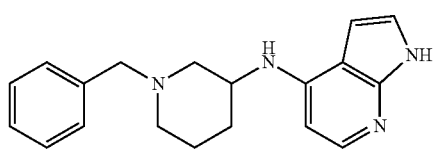 [SMILES: c1ccc(CN2CCCC(Nc3ccnc4[nH]ccc34)C2)cc1]

N-(1-Benzylpiperidin-3-yl)-1H-pyrrolo[2,3-b]pyridin-4-amine, Compound 4.001

Reaction of N-(piperidin-3-yl)-1H-pyrrolo[2,3-b]pyridin-4-amine with benzaldehyde using the method of Example 8 affords the title compound.

Example 136

Prophetic Example

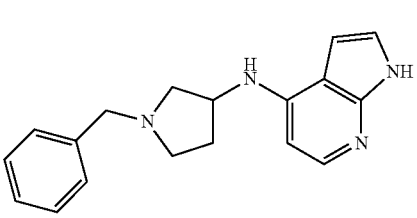 [SMILES: c1ccc(CN2CCC(Nc3ccnc4[nH]ccc34)C2)cc1]

N-(1-Benzylpyrrolidin-3-yl)-1H-pyrrolo[2,3-b]pyridin-4-amine, Compound 4.002

Application of the reaction sequence described in Examples 133 through 135, with the modification that tert-butyl 3-aminopyrrolidine-1-carboxylate is substituted for tert-butyl 3-aminopiperidine-1-carboxylate, affords the title compound.

Example 137

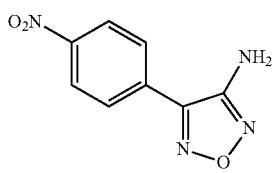 [SMILES: Nc1nonc1-c1ccc([N+](=O)[O-])cc1]

4-(4-Nitrophenyl)-1,2,5-oxadiazol-3-amine

Into a round bottom flask were added 2-(4-nitrophenyl)acetonitrile (5.00 g, 30.8 mmol) and ethanol (25 mL). The suspension was cooled to 0° C. and sodium ethoxide in ethanol (12.0 mL, 3.08 M, 27.0 mmol) was added dropwise. The reaction immediately turned bright pink. After 10 minutes, amyl nitrite (5.42 g, 46.2 mmol) was added dropwise. The reaction turned dark green. After 20 minutes, the reaction solidified, and the solid was broken up and an additional 25 mL of ethanol was added. After one hour, the NMR indicated that the reaction was complete. The reaction was diluted with ethyl acetate and washed with 1 M HCl, saturated sodium bicarbonate, and brine. The organic phase was separated and dried over MgSO$_4$, filtered and concentrated. Chromatography of the residue on silica gel, eluting with 20% EtOAc/heptane, gave the title compound as a yellow solid (5.40 g, 92%).

The above product (4.00 g, 20.9 mmol) was combined in a round bottom flask with potassium carbonate in water (40 mL, 3.00 M, 120 mmol), and hydroxylamine in water (13.8 mL, 15.1 M, 208 mmol). The mixture was stirred at 95° C. overnight, after which the aqueous layer was poured off and the remaining oil was dissolved in ethyl acetate, washed with water, dried over MgSO$_4$, and filtered. The crude product was concentrated and purified by chromatography on silica gel, eluting with 30% EtOAc/hexane, to afford the title compound as a yellow solid (2.00 g, 46%).

Example 138

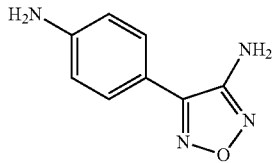 [SMILES: Nc1ccc(-c2nonc2N)cc1]

4-(4-Aminophenyl)-1,2,5-oxadiazol-3-amine 4-(4-Nitrophenyl)-1,2,5-oxadiazol-3-amine (0.500 g, 2.42 mmol), tin dichloride (1.61 g, 8.49 mmol), and water (0.306 mL, 17.0 mmol) were combined in ethyl acetate (20 mL) in a round bottom flask, and the mixture was stirred at room temperature overnight. The solvent was removed and methylene chloride was added, and the mixture was washed three times with aqueous NaOH. The organic phase was dried over MgSO$_4$, filtered, and concentrated to afford the title compound as a yellow solid (400 mg, 94%).

Example 139

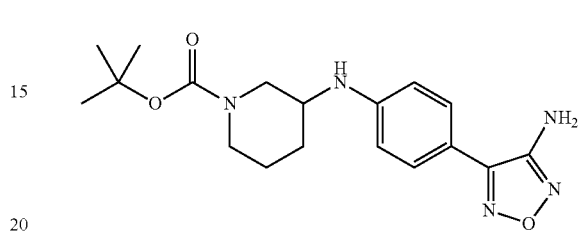

tert-Butyl 3-(4-(4-Amino-1,2,5-oxadiazol-3-yl)phenylamino)piperidine-1-carboxylate Reaction of tert-butyl 3-oxopiperidine-1-carboxylate and 4-(4-aminophenyl)-1,2,5-oxadiazol-3-amine using the method of Example 3 afforded the title compound.

Example 140

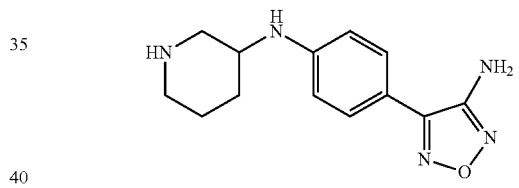

4-(4-(Piperidin-3-ylamino)phenyl)-1,2,5-oxadiazol-3-amine

Deprotection of tert-butyl 3-(4-(4-amino-1,2,5-oxadiazol-3-yl)phenylamino)-piperidine-1-carboxylate using the method of Example 4 afforded the title compound.

Example 141

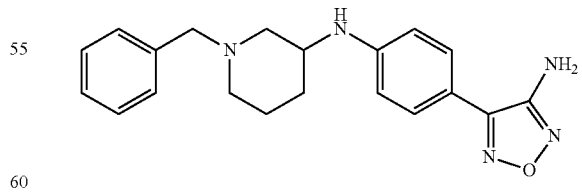

4-(4-(1-(4-Benzylpiperidin-3-ylamino)phenyl)-1,2,5-oxadiazol-3-amine, Compound 5.001

Reaction of 4-(4-(piperidin-3-ylamino)phenyl)-1,2,5-oxadiazol-3-amine with benzaldehyde using the method of Example 8 afforded the title compound. $^1$H NMR (CDCl$_3$, 300 MHz): δ 7.50 (m, 2H), 7.35-7.26 (m, 5H), 6.66 (d, J=8.7

Hz, 2H), 4.5 (bs, 1H), 4.23 (s, 2H), 3.63 (bs, 1H), 3.52 (dd, J=13.5, 17.7 Hz, 2H), 2.67 (d, J=10.5 Hz, 1H), 2.50-2.31 (m, 2H), 1.70 (m, 2H), 1.56 (m, 2H).

Example 142

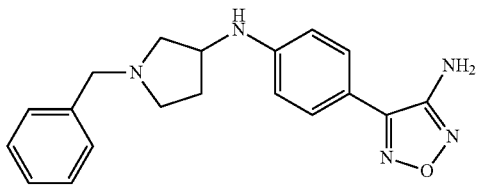 [SMILES: Nc1nonc1-c1ccc(NC2CCN(Cc3ccccc3)C2)cc1]

4-(4-(1-(4-Benzylpyrrolidin-3-ylamino)phenyl)-1,2,5-oxadiazol-3-amine, Compound 5.002

Application of the reaction sequence described in Examples 139 through 141, with the modification that tert-butyl 3-oxopyrrolidine-1-carboxylate is substituted for tert-butyl 3-oxopiperidine-1-carboxylate, afforded the title compound.

$^1$H NMR (CDCl$_3$, 300 MHz): δ 7.50 (m, 2H), 7.35-7.26 (m, 5H), 6.63 (d, J=8.7 Hz, 2H), 4.31 (d, J=7.5 Hz, 1H), 4.23 (s, 2H), 4.05 (m, 1H), 3.64 (m, 2H), 2.86-2.74 (m, 2H), 2.60 (dd, J=3.6, 9.9 Hz, 1H), 2.50-2.31 (m, 2H), 1.95 (bs, 1H), 1.70 (m, 1H).

Example 143

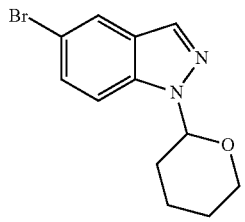 [SMILES: Brc1ccc2c(cnn2C2CCCCO2)c1]

5-Bromo-1-(tetrahydro-2H-pyran-2-yl)-1H-indazole

A 250 mL round bottom flask with was charged with 5-bromo-1H-indazole (25.00 g, 0.127 mol, 1.0 eq), and dichloromethane (100 mL). To the suspension was added dihydropyran (32.0 g, 0.381 mol, 3.0 eq) and a catalytic amount of pyridinium para-toluenesulfonate (3.19 g, 0.0127 mol, 0.10 eq). The mixture was stirred overnight, and in the morning was a clear solution. The methylene chloride was washed sequentially with saturated sodium bicarbonate, 10% citric acid, and brine, and was then evaporated. Chromatography of the residue on silica gel, eluting with EtOAc/heptane, gave the title compound as a colorless liquid (28.00 g, 79%).

$^1$H NMR (CDCl$_3$, 300 MHz): δ 8.11 (s, 1H), 7.82 (d, J=1.8 Hz, 1H), 7.60 (d, J=9.0 Hz, 1H), 7.33 (dd, J=1.8, 9.0, 1H), 5.66 (dd, J=3.6, 8.4 Hz, 1H), 4.11 (m, 1H), 3.78 (m, 1H), 2.20 (m, 2H), 2.05 (m, 1H), 1.75 (m, 3H).

Example 144

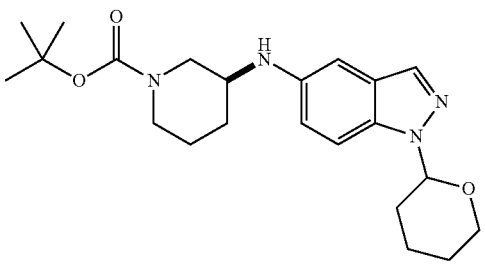

(3S)-tert-Butyl 3-(1-(Tetrahydro-2H-pyran-2-yl)-1H-indazol-5-ylamino)piperidine-1-carboxylate A 500 mL round bottom flask with a stirbar was charged with 5-bromo-1-(tetrahydro-2H-pyran-2-yl)-1H-indazole (28.0 g, 0.0996 mol, 1.00 eq), (S)-3-amino-Boc-piperidine (21.75 g, 0.109 mol, 1.09 eq), tris(dibenzylideneacetone)dipalladium (4.75 g, 5.18 mmol, 0.052 eq), racemic BINAP (7.44 g, 12.0 mmol, 0.12 eq), and sodium tert-butoxide (28.7 g, 0.299 mol, 3.00 eq). The flask containing the solids was then evacuated and back-filled with nitrogen three times to degas. Pyridine (200 mL) was then added, and the flask was again purged three times with vacuum and nitrogen. The dark greenish mixture was then stirred at 55° C. overnight under a nitrogen atmosphere. In the morning, the reaction was cooled to room temperature, diluted with 250 mL EtOAc, washed three times with 250 mL portions of 10% NaHSO$_4$, and the organic phase was evaporated. The residue was dissolved in toluene and loaded onto a silica column that had been packed with heptane. The column was washed with 5 column volumes of heptane, after which the desired product was eluted with EtOAc/heptane, to provide the title compound as a pale yellow foam (2.4 g, 81%).

$^1$H NMR (CDCl$_3$, 300 MHz): δ 7.86 (s, 1H), 7.54 (d, J=9.0 Hz, 1H), 6.72 (dd, J=2.1, 9.0 Hz, 1H), 6.31 (s, 1H), 5.59 (dd, J=3.0, 9.0 Hz, 1H), 4.10 (m, 2H), 3.75 (m, 2H), 3.52 (m, 1H), 3.38 (m, 1H), 3.07 (m, 1H), 2.88 (m, 1H), 2.20 (m, 2H), 2.05 (m, 2H), 1.75-1.65 (m, 8H), 1.46 (s, 9H).

Example 145

(3R)-tert-Butyl 3-(1-(Tetrahydro-2H-pyran-2-yl)-1H-indazol-5-ylamino)piperidine-1-carboxylate Coupling of 5-bromo-1-(tetrahydro-2H-pyran-2-yl)-1H-indazole with (R)-3-amino-Boc-piperidine using the method of Example 144 afforded the title compound.

Example 146

(3S)-tert-Butyl 3-(1-(Tetrahydro-2H-pyran-2-yl)-1H-indazol-5-ylamino)pyrrolidin-1-carboxylate Coupling of 5-bromo-1-(tetrahydro-2H-pyran-2-yl)-1H-indazole with (S)-3-amino-Boc-pyrrolidine using the method of Example 144 afforded the title compound.

Example 147

(3R)-tert-Butyl 3-(1-(Tetrahydro-2H-pyran-2-yl)-1H-indazol-5-ylamino)pyrrolidin-1-carboxylate Coupling of 5-bromo-1-(tetrahydro-2H-pyran-2-yl)-1H-indazole with (R)-3-amino-Boc-pyrrolidine using the method of Example 144 afforded the title compound.

Example 148

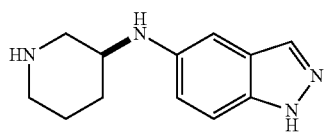

(S)—N-(Piperidin-3-yl)-1H-indazol-5-amine Dihydrochloride

A 1 L round bottom flask was charged with (3S)-tert-butyl 3-(1-(tetrahydro-2H-pyran-2-yl)-1H-indazol-5-ylamino)piperidine-1-carboxylate (32.4 g, 0.0809 mol, 1.00 eq) and EtOH (500 mL). To the ethanol solution was added 4N HCl in dioxane (40.0 mL, 0.160 mol, 2.0 eq), and the solution was stirred at room temperature for 2 h, giving an inhomogeneous dark brown solution. The solution was then heated to 75° C. with a mechanical stirrer and maintained at that temperature for 2 h, after which it was cooled to room temperature. A large amount of fine white solid was observed to form and was collected by filtration, and the filter cake was washed with isopropyl acetate (500 mL). The solid was dried in a vacuum oven at 45° C. for 3 days to give the title compound as an off-white powder (18.1 g, 77%).

$^1$H NMR (CD$_3$OD, 300 MHz): δ 8.28 (s, 1H), 7.70 (m, 2H), 7.46 (dd, J=2.1, 9.0 Hz, 1H), 3.96 (m, 1H), 3.60 (m, 2H), 3.36 (m, 1H), 3.15 (m, 1H), 3.04 (m, 1H), 2.20 (m, 2H), 1.85 (m, 2H).

Example 149

(R)—N-(Piperidin-3-yl)-1H-indazol-5-amine Dihydrochloride

Deprotection of (3R)-tert-butyl 3-(1-(tetrahydro-2H-pyran-2-yl)-1H-indazol-5-ylamino)piperidine-1-carboxylate using the method of Example 148 afforded the title compound.

Example 150

(S)—N-(Pyrrolidin-3-yl)-1H-indazol-5-amine Dihydrochloride

Deprotection of (3S)-tert-butyl 3-(1-(tetrahydro-2H-pyran-2-yl)-1H-indazol-5-ylamino)pyrrolidine-1-carboxylate using the method of Example 148 afforded the title compound.

Example 151

(R)—N-(Pyrrolidin-3-yl)-1H-indazol-5-amine Dihydrochloride

Deprotection of (3R)-tert-butyl 3-(1-(tetrahydro-2H-pyran-2-yl)-1H-indazol-5-ylamino)pyrrolidine-1-carboxylate using the method of Example 148 afforded the title compound.

Examples 152-175

Reaction of 2,2-dimethyl-1-(5-(piperidin-3-ylamino)-1H-Indazol-1-yl)propan-1-one with the appropriate aldehydes using the method of Example 8 followed by deprotection using the method of Example 9 afforded the compounds in Examples 152-175:

Example 152

N-(1-((1H-Indol-6-yl)methyl)piperidin-3-yl)-1H-indazol-5-amine, Compound 1.082

$^1$H NMR (CDCl$_3$, 300 MHz): δ 8.08 (bs, 1H), 7.86 (s, 1H), 7.55 (m, 1H), 7.30 (m, 1H), 7.20 (m, 1H), 7.10 (m, 1H), 6.82 (m, 2H), 6.50 (m, 1H), 3.68-3.50 (m, 3H), 2.80 (m, 1H), 2.45-2.35 (m, 3H), 1.76 (m, 2H), 1.60 (m, 2H).

Example 153

5-((3-(1H-Indazol-5-ylamino)piperidin-1-yl)methyl)-2-ethynylphenol, Compound 1.083

Example 154

3-(3-((3-(1H-Indazol-5-ylamino)piperidin-1-yl)methyl)phenoxy)propan-1-ol, Compound 1.084

$^1$H NMR (CDCl$_3$, 300 MHz): δ 9.85 (bs, 1H), 7.86 (s, 1H), 7.31-7.2 (m, 2H), 6.94 (m, 2H), 6.83 (m, 3H), 4.09 (m, 2H), 3.87 (m, 2H), 3.61 (bs, 1H) 3.48 (m, 2H), 2.76 (m, 1H), 2.45 (m, 3H), 2.04 (m, 2H), 1.75 (m, 2H) 1.59 (m, 3H).

Example 155

N-(1-(3-(2-Aminoethoxy)benzyl)piperidin-3-yl)-1H-indazol-5-amine, Compound 1.085

Prepared by coupling with the BOC-protected aminoaldehyde, followed by deprotection using the method of Example 9.

Example 156

2-(3-((3-(1H-Indazol-5-ylamino)piperidin-1-yl)methyl)phenoxy)acetic acid, Compound 1.086

$^1$H NMR (CD$_3$OD, 300 MHz): δ 7.86 (s, 1H), 7.40 (m, 3H), 7.00 (m, 4H), 4.85 (s, 2H), 4.65 (bs, 2H), 4.32 (dd, J=12.9, 30.0 Hz, 2H), 3.80 (bs, 1H), 3.40 (bs, 1H), 3.30 (s, 2H), 3.00 (bs, 1H), 2.13 (bs, 2H), 1.90 (m, 1H), 1.60 (bs, 1H).

Example 157

N-(1-(3-Amino-4-chlorobenzyl)piperidin-3-yl)-1H-indazol-5-amine, Compound 1.089

$^1$H NMR (CD$_3$OD, 300 MHz): δ 7.78 (s, 1H), 7.32 (d, J=9.0 Hz, 1H), 7.14 (d, J=8.1 Hz, 1H), 6.91 (dd, J=2.1, 9.0 Hz,

1H), 6.83 (m, 2H), 6.61 (dd, J=1.8, 8.1 Hz, 1H), 3.52 (m, 4H), 3.07 (m, 1H), 2.80 (m, 1H), 2.35 (m, 1H), 2.15 (m, 1H), 2.00 (m, 1H), 1.85 (m, 1H), 1.75 (m, 1H), 1.40 (m, 1H).

Example 158

2-(3-(3-(1H-Indazol-5-ylamino)piperidin-1-yl)methyl)phenoxy)acetamide, Compound 1.098

$^1$H NMR (CDCl$_3$, 300 MHz): δ 9.95 (bs, 1H), 7.86 (s, 1H), 7.27-7.18 (m, 2H), 6.97 (m, 2H), 6.83 (m, 3H), 6.58 (bs, 1H), 5.65 (bs, 1H), 4.50 (s, 2H), 3.61 (bs, 1H), 3.50 (dd, J=13.5, 23.7 Hz, 2H), 2.78 (m, 1H), 2.45-2.35 (m, 3H), 1.76 (m, 2H), 1.60 (m, 2H).

Example 159

2-(6-((3-(1H-Indazol-5-ylamino)piperidin-1-yl)methyl)-1H-indol-1-yl)acetamide, Compound 1.099

$^1$H NMR (CDCl$_3$, 300 MHz): δ 9.90 (bs, 1H), 7.82 (s, 1H), 7.60 (d, J=7.8 Hz, 1H), 7.27-7.18 (m, 2H), 7.18 (d, J=7.5 Hz, 1H), 7.07 (s, 1H), 6.83 (d, J=8.7 Hz, 1H), 6.77 (s, 1H), 6.59 (s, 1H), 5.30 (bs, 1H), 5.24 (bs, 1H), 4.78 (bs, 2H), 3.70-3.57 (m, 3H), 2.78 (m, 1H), 2.45-2.35 (m, 3H), 1.76 (m, 2H), 1.60 (m, 2H).

Example 160

N-(1-((1H-Indol-5-yl)methyl)piperidin-3-yl)-1H-indazol-5-amine, Compound 1.100

$^1$H NMR (CD$_3$OD, 300 MHz): δ 7.75 (s, 1H), 7.50 (s, 1H), 7.32 (m, 2H), 7.20 (m, 1H), 7.08 (m, 1H), 6.90 (m, 1H), 6.83 (s, 1H), 6.40 (m, 1H), 4.6 (bs, 2H), 3.65 (m, 2H) 3.50 (m, 1H), 3.30 (m, 1H), 3.15 (m, 1H), 2.80 (m, 1H), 2.20 (m, 1H), 2.00 (m, 2H), 1.75 (m, 1H) 1.65 (m, 1H), 1.35 (m, 1H).

Example 161

2-(6-((3-(1H-Indazol-5-ylamino)piperidin-1-yl)methyl)-1H-indol-1-yl)ethanol, Compound 1.101

$^1$H NMR (CD$_3$OD, 300 MHz): δ 7.72 (s, 1H), 7.53 (d, J=8.1 Hz, 1H), 7.45 (s, 1H), 7.31 (d, J=9.0 Hz, 1H), 7.27 (d, J=3.0 Hz, 1H), 7.05 (dd, J=1.2, 8.1 Hz, 1H), 6.91 (dd, J=2.1, 8.7 Hz, 1H), 6.82 (s, 1H), 6.44 (s, 1H), 4.23 (t, J=5.4 Hz, 2H), 3.95 (dd, J=12.9, 28.2 Hz, 2H), 3.84 (t, J=5.4 Hz, 2H), 3.60 (m, 1H), 3.00 (m, 1H), 2.50 (m, 1H), 2.36 (m, 1H), 2.05 (m, 1H), 1.95 (m, 1H), 1.76 (m, 1H), 1.40 (m, 1H).

Example 162

N-(5-((3-(1H-Indazol-5-ylamino)piperidin-1-yl)methyl)-2-chlorophenyl)methanesulfonamide, Compound 1.102

$^1$H NMR (CD$_3$OD, 300 MHz): δ 7.78 (s, 1H), 7.58 (d, J=1.8 Hz, 1H), 7.41 (d, J=9.6 Hz, 1H), 7.31 (d, J=9.0 Hz, 1H), 7.18 (dd, J=1.8, 8.4 Hz, 1H), 6.93 (dd, J=2.1, 9.0 Hz, 1H), 6.85 (s, 1H), 3.50 (m, 3H), 2.95 (m, 1H), 2.91 (s, 3H), 2.26 (m, 1H), 2.05 (m, 1H), 1.95 (m, 1H), 1.76 (m, 1H), 1.65 (m, 1H), 1.40 (m, 1H).

Example 163

2-(6-((3-(1H-Indazol-5-ylamino)piperidin-1-yl)methyl)-1H-indol-1-yl)acetic acid, Compound 1.103

Prepared by coupling of the corresponding tert-butyl ester, followed by deprotection using the method of Example 4.
$^1$H NMR (CD$_3$OD, 300 MHz): δ 8.55 (s, 1H), 7.75 (s, 1H), 7.48 (m, 1H), 7.32 (m, 2H), 7.15 (m, 1H), 7.02 (d, J=7.5 Hz, 1H), 6.93 (m, 2H), 6.39 (m, 1H), 4.65 (m, 2H), 3.70-3.57 (m, 3H), 2.78 (m, 1H), 2.26 (m, 1H), 2.05 (m, 1H), 1.95 (m, 1H), 1.76 (m, 1H), 1.65 (m, 1H), 1.40 (m, 1H).

Example 164

2-(6-(((3-(1H-Indazol-5-ylamino)piperidin-1-yl)methyl)indolin-1-yl)ethanol, Compound 1.104

$^1$H NMR (CDCl$_3$, 300 MHz): δ 7.87 (s, 1H), 7.27-7.18 (m, 2H), 7.02 (d, J=6.9 Hz, 1H), 6.83 (m, 2H), 6.63 (m, 2H), 3.80 (m, 2H), 3.70-3.57 (m, 3H), 3.40 (m, 2H), 3.25 (m, 2H), 2.95 (m, 2H), 2.78 (m, 1H), 2.45-2.35 (m, 3H), 1.76 (m, 2H), 1.60 (m, 2H).

Example 165

2-(5-((3-(1H-Indazol-5-ylamino)piperidin-1-yl)methyl)-1H-indol-1-yl)acetamide, Compound 1.105

$^1$H NMR (CDCl$_3$, 300 MHz): δ 7.79 (s, 1H), 7.55 (s, 1H), 7.27-7.18 (m, 3H), 7.05 (d, J=3.0 Hz, 1H), 6.79 (dd, J=2.1, 8.7 Hz, 1H), 6.76 (s, 1H), 6.55 (d, J=3.0 Hz, 1H), 5.96 (bs, 1H), 5.30 (bs, 1H), 4.75 (s, 2H), 3.70-3.57 (m, 3H), 2.78 (m, 1H), 2.45-2.35 (m, 3H), 1.76 (m, 2H), 1.60 (m, 2H).

Example 166

N-(2-(3-((3-(1H-Indazol-5-ylamino)piperidin-1-yl)methyl)phenoxy)ethyl)acetamide, Compound 1.111

$^1$H NMR (CD$_3$OD, 300 MHz): δ 7.77 (s, 1H), 7.31 (d, J=8.7 Hz, 1H), 7.21 (t, J=7.8 Hz, 1H), 6.94 (m, 3H), 6.83 (m, 2H), 4.14 (m, 2H), 3.53 (m, 4H), 3.07 (m, 2H), 2.75, 2.20 (m, 2H), 1.97 (m, 5H), 1.78 (m, 1H), 1.68 (m, 1H), 1.40 (m, 1H).

Example 167 tert-butyl 2-(5-((3-(1H-Indazol-5-ylamino)piperidin-1-yl)methyl)-1H-indol-1-yl)acetate, Compound 1.112

$^1$H NMR (CDCl$_3$, 300 MHz): δ 7.84 (s, 1H), 7.54 (s, 1H), 7.28 (m, 2H), 7.19 (s, 1H), 7.07 (d, J=3.0 Hz, 1H), 6.82 (m, 2H), 6.51 (d, J=3.0 Hz, 1H), 4.72 (s, 2H), 3.63 (m, 3H), 2.78 (m, 1H), 2.45-2.35 (m, 3H), 1.76 (m, 2H), 1.60 (m, 2H) 1.45 (s, 9H).

Example 168

2-(5-((3-(1H-Indazol-5-ylamino)piperidin-1-yl)methyl)-1H-indol-1-yl)ethanol, Compound 1.114

$^1$H NMR (CDCl$_3$, 300 MHz): δ 7.74 (s, 1H), 7.57 (s, 1H), 7.27-7.18 (m, 4H), 6.81 (d, J=8.7 Hz, 1H), 6.77 (s, 1H), 6.49

(d, J=3.0 Hz, 1H), 4.27 (m, 2H), 3.92 (m, 2H), 3.61 (m, 2H), 3.57 (bs, 1H), 2.78 (m, 1H), 2.45-2.35 (m, 3H), 1.76 (m, 2H), 1.60 (m, 2H).

Example 169

2-(5-((3-(1H-Indazol-5-ylamino)piperidin-1-yl)methyl)-1H-indol-1-yl)acetic acid, Compound 1.119

Prepared by deprotection of Compound 1.112 using the method of Example 4.

Example 170

N-(3-((3-(1H-Indazol-5-ylamino)piperidin-1-yl)methyl)phenyl)ethanesulfonamide, Compound 1.120

$^1$H NMR (CD$_3$OD, 300 MHz): δ 7.77 (s, 1H), 7.35-7.23 (m, 3H), 7.10 (t, J=7.2 Hz, 2H), 6.91 (dd, J=1.8, 9.0 Hz, 1H), 6.83 (s, 1H), 3.50 (m, 2H), 3.48 (m, 1H), 2.96 (q, J=7.2 Hz, 2H), 2.72 (m, 1H), 2.32 (m, 1H), 1.97 (m, 2H), 1.78 (m, 1H), 1.68 (m, 1H), 1.40 (m, 1H), 1.19 (t, J=7.2 Hz, 3H).

Example 171

N-(3-((3-(1H-Indazol-5-ylamino)piperidin-1-yl)methyl)phenyl)-N-methylmethanesulfonamide, Compound 1.121

$^1$H NMR (CD$_3$OD, 300 MHz): δ 7.78 (s, 1H), 7.42 (s, 1H), 7.35-7.23 (m, 4H), 6.91 (dd, J=2.1, 9.0 Hz, 1H), 6.84 (s, 1H), 3.50 (s, 2H), 3.48 (m, 1H), 3.25 (s, 3H), 2.97 (d, J=10.5 Hz, 1H), 2.80 (s, 3H), 2.72 (m, 1H), 2.32 (m, 1H), 1.97 (m, 2H), 1.78 (m, 1H), 1.68 (m, 1H), 1.40 (m, 1H).

Example 172

N-(3-(3-(1H-Indazol-5-ylamino)piperidin-1-yl)methyl)benzyl)acetamide, Compound 1.122

$^1$H NMR (CDCl$_3$, 300 MHz): δ 7.85 (s, 1H), 7.32-7.23 (m, 4H), 7.15 (d, J=6.9 Hz, 1H), 6.82 (m, 2H), 5.70 (bs, 1H), 4.40 (d, J=5.7 Hz, 1H), 3.60 (bs, 1H), 3.52 (dd, J=13.5, 27.0 Hz, 2H), 2.78 (m, 1H), 2.45-2.35 (m, 3H), 2.00 (s, 3H), 1.76 (m, 2H), 1.60 (m, 2H).

Example 173

2-(3-((4-(1H-Indazol-5-ylamino)piperidin-1-yl)methyl)phenoxy)ethanol, Compound 1.130

$^1$H NMR (CDCl$_3$, 300 MHz): δ 7.88 (s, 1H), 7.30-7.22 (m, 2H), 6.93 (m, 2H), 6.82 (m, 3H), 4.13 (m, 2H), 3.95 (m, 2H), 3.53 (s, 2H), 3.30 (m, 1H), 2.88 (d, J=11.4 Hz, 2H), 2.3-2.00 (m, 4H), 1.76-1.50 (m, 2H).

Example 174

N-(3-((3-(1H-Indazol-5-ylamino)pyrrolidin-1-yl)methyl)phenyl)methanesulfonamide, Compound 1.087

$^1$H NMR (CDCl$_3$, 300 MHz): δ 9.90 (bs, 1H), 7.88 (s, 1H), 7.32 (m, 2H), 7.16 (s, 1H), 7.11 (m, 2H), 6.82 (dd, J=2.1, 8.7 Hz, 1H), 6.74 (d, J=1.5 Hz, 1H), 6.48 (bs, 1H), 4.11 (m, 1H), 3.63 (dd, J=13.5, 34.5 Hz, 2H), 2.93 (s, 3H), 2.89 (m, 1H), 2.71 (m, 2H), 2.45 (m, 1H), 2.35 (m, 1H), 1.73 (m, 1H).

Example 175

2-(3-((3-(1H-Indazol-5-ylamino)pyrrolidin-1-yl)methyl)phenoxy)ethanol, Compound 1.088

$^1$H NMR (CDCl$_3$, 300 MHz): δ 9.80 (bs, 1H), 7.90 (s, 1H), 7.32 (m, 2H), 6.95 (m, 2H), 6.82 (m, 3H), 4.11 (m, 3H), 3.95 (m, 2H), 3.63 (m, 2H), 2.89 (m, 2H), 2.71 (m, 1H), 2.45 (m, 1H), 2.35 (m, 1H), 2.00 (m, 1H), 1.73 (m, 1H).

Examples 176-197

Reaction of (R)—N-(piperidin-3-yl)-1H-indazol-5-amine dihydrochloride with the appropriate aldehydes using the method of Example 8 with the variation that sodium cyanoborohydride was used as reductant and methanol was used as the reaction solvent afforded the compounds in Examples 176-197:

Example 176

(R)-2-(3-((3-(1H-Indazol-5-ylamino)piperidin-1-yl)methyl)phenoxy)ethanol, Compound 1.092

$^1$H NMR (CDCl$_3$, 300 MHz): δ 7.86 (s, 1H), 7.31-7.2 (m, 2H), 6.94 (m, 2H), 6.83 (m, 3H), 4.09 (m, 2H), 3.96 (m, 2H), 3.61 (m, 1H) 3.50 (m, 2H), 2.80 (m, 1H), 2.45 (m, 3H), 1.75 (m, 2H) 1.59 (m, 3H).

Example 177

(R)—N-(3-((3-(1H-Indazol-5-ylamino)piperidin-1-yl)methyl)phenyl)methanesulfonamide, Compound 1.093

$^1$H NMR (CDCl$_3$, 300 MHz): δ 7.86 (s, 1H), 7.32-7.25 (m, 2H), 7.09 (m, 2H), 6.87 (dd, J=2.1, 9.0 Hz, 1H), 6.79 (s, 1H), 6.32 (bs, 1H), 3.61 (m, 1H) 3.53 (dd, J=10.8, 35.1 Hz, 2H), 2.91 (s, 3H), 2.61 (m, 1H), 2.45 (m, 3H), 1.76 (m, 2H) 1.60 (m, 3H).

Example 178

(R)-2-(6-((3-(1H-Indazol-5-ylamino)piperidin-1-yl)methyl)-1H-indol-1-yl)acetamide, Compound 1.106

$^1$H NMR (CDCl$_3$, 300 MHz): δ 7.82 (s, 1H), 7.60 (d, J=8.1 Hz, 1H), 7.27-7.18 (m, 2H), 7.17 (d, J=7.5 Hz, 1H), 7.06 (d, J=3.0 Hz, 1H), 6.83 (d, J=7.8 Hz, 1H), 6.77 (s, 1H), 6.59 (d, J=3.0 Hz, 1H), 5.23 (bs, 2H), 4.78 (s, 2H), 3.70-3.57 (m, 3H), 2.78 (m, 1H), 2.45-2.35 (m, 3H), 1.76 (m, 2H), 1.60 (m, 2H).

Example 179

(R)-2-(6-((3-(1H-Indazol-5-ylamino)piperidin-1-yl)methyl)-1H-indol-1-yl)ethanol, Compound 1.108

$^1$H NMR (CDCl$_3$, 300 MHz): δ 9.80 (bs, 1H), 7.82 (s, 1H), 7.59 (m, 1H), 7.37 (s, 1H), 7.24 (s, 1H), 7.15 (m, 2H), 6.83 (m, 2H), 6.50 (m, 1H), 4.28 (m, 2H), 3.96 (m, 2H), 3.75 (m, 1H) 3.60 (m, 2H), 2.80 (m, 1H), 2.45 (m, 3H), 1.75 (m, 2H) 1.59 (m, 2H).

Example 180

(R)—N-(1-Benzylpiperidin-3-yl)-1H-indazol-5-amine, Compound 1.110

$^1$H NMR (CDCl$_3$, 300 MHz): δ 7.86 (s, 1H), 7.37-7.24 (m, 6H), 6.83 (m, 2H), 3.62 (bs, 1H), 3.58 (m, 2H), 2.80 (m, 1H), 2.45 (m, 3H), 1.75 (m, 2H) 1.59 (m, 2H).

Example 181

(R)-3-(3-(((R)-3-(1H-Indazol-5-ylamino)piperidin-1-yl)methyl)phenoxy)propane-1,2-diol, Compound 1.115

$^1$H NMR (CDCl$_3$, 300 MHz): δ 7.86 (s, 1H), 7.27-7.18 (m, 2H), 6.94 (m, 2H), 6.83 (m, 3H), 4.10 (m, 3H), 3.85 (m, 1H), 3.77 (m, 1H), 3.60 (bs, 1H), 3.51 (m, 2H), 2.78 (m, 1H), 2.45-2.35 (m, 3H), 1.76 (m, 2H), 1.60 (m, 2H).

Example 182

(R)-1-(3-(((R)-3-(1H-Indazol-5-ylamino)piperidin-1-yl)methyl)phenoxy)propan-2-ol, Compound 1.116

$^1$H NMR (CDCl$_3$, 300 MHz): δ 7.86 (s, 1H), 7.27-7.18 (m, 2H), 6.94 (m, 2H), 6.83 (m, 3H), 4.20 (m, 1H), 3.95 (m, 1H), 3.81 (m, 1H), 3.60 (bs, 1H), 3.51 (m, 2H), 2.78 (m, 1H), 2.45-2.35 (m, 3H), 1.76 (m, 2H), 1.60 (m, 2H), 1.29 (d, J=6.6 Hz, 3H).

Example 183

(R)-3-(3-(((S)-3-(1H-Indazol-5-ylamino)piperidin-1-yl)methyl)phenoxy)propane-1,2-diol, Compound 1.117

$^1$H NMR (CDCl$_3$, 300 MHz): δ 7.86 (s, 1H), 7.27-7.18 (m, 2H), 6.94 (m, 2H), 6.83 (m, 3H), 4.10 (m, 3H), 3.85 (m, 1H), 3.77 (m, 1H), 3.60 (bs, 1H), 3.51 (m, 2H), 2.78 (m, 1H), 2.45-2.35 (m, 3H), 1.76 (m, 2H), 1.60 (m, 2H).

Example 184

(R)-1-(3-(±)-3-(1H-Indazol-5-ylamino)piperidin-1-yl)methyl)phenoxy)propan-2-ol, Compound 1.118

$^1$H NMR (CDCl$_3$, 300 MHz): δ 7.86 (s, 1H), 7.27-7.18 (m, 2H), 6.94 (m, 2H), 6.83 (m, 3H), 4.20 (m, 1H), 3.95 (m, 1H), 3.81 (m, 1H), 3.60 (bs, 1H), 3.51 (m, 2H), 2.78 (m, 1H), 2.45-2.35 (m, 3H), 1.76 (m, 2H), 1.60 (m, 2H), 1.29 (d, J=6.6 Hz, 3H).

Example 185

(R)—N-(3-((3-(1H-Indazol-5-ylamino)piperidin-1-yl)methyl)phenyl)ethanesulfonamide, Compound 1.123

$^1$H NMR (CDCl$_3$, 300 MHz): δ 9.95 (bs, 1H), 7.86 (s, 1H), 7.32-7.23 (m, 3H), 7.08 (m, 2H), 6.88 (dd, J=1.8, 8.7 Hz, 1H), 6.79 (s, 1H), 6.50 (m, 1H), 3.60 (bs, 1H), 3.43 (dd, J=13.5, 38.1 Hz, 2H), 3.06 (m, 2H), 2.68 (m, 2H), 2.45-2.35 (m, 2H), 1.76 (m, 2H), 1.60 (m, 2H), 1.28 (t, J=7.5 Hz, 3H).

Example 186

(R)-2-(3-(3-(1H-Indazol-5-ylamino)piperidin-1-yl)methyl)phenoxy)acetic acid, Compound 1.125

Prepared by coupling of the corresponding tert-butyl ester, followed by deprotection using the method of Example 4.

$^1$H NMR (CD$_3$OD, 300 MHz): δ 7.86 (s, 1H), 7.40 (m, 3H), 7.00 (m, 4H), 4.85 (s, 2H), 4.65 (bs, 2H), 4.32 (dd, J=12.9, 30.0 Hz, 2H), 3.80 (bs, 1H), 3.40 (bs, 1H), 3.30 (s, 2H), 3.00 (bs, 1H), 2.13 (bs, 2H), 1.90 (m, 1H), 1.60 (bs, 1H).

Example 187

(R)-2-(3-((3-(1H-Indazol-5-ylamino)piperidin-1-yl)methyl)phenoxy)-N-(pyridin-3-yl)acetamide, Compound 1.126

$^1$H NMR (CDCl$_3$, 300 MHz): δ 9.95 (bs, 1H), 8.65 (d, J=2.4 Hz, 1H), 8.40 (dd, J=1.2, 4.8 Hz, 1H), 8.34 (s, 1H), 8.22 (d, J=6.3 Hz, 1H), 7.86 (s, 1H), 7.31-7.2 (m, 2H), 7.03 (m, 2H), 6.83 (m, 3H), 5.40 (bs, 1H), 4.64 (s, 2H), 3.65 (bs, 1H), 3.52 (dd, J=13.5, 21.0 Hz, 2H), 2.76 (m, 1H), 2.45 (m, 3H), 1.75 (m, 2H) 1.59 (m, 2H).

Example 188

(R)-2-(3-((3-(1H-Indazol-5-ylamino)piperidin-1-yl)methyl)phenoxy)-1-morpholinoethanone, Compound 1.127

$^1$H NMR (CDCl$_3$, 300 MHz): δ 9.95 (bs, 1H), 7.86 (s, 1H), 7.31-7.2 (m, 2H), 7.03 (m, 2H), 6.83 (m, 3H), 5.40 (bs, 1H), 4.69 (s, 2H), 3.62 (bs, 9H), 3.49 (m, 2H), 2.76 (m, 1H), 2.45 (m, 3H), 1.75 (m, 2H) 1.59 (m, 2H).

Example 189

(R)-2-(3-((3-(1H-Indazol-5-ylamino)piperidin-1-yl)methyl)phenoxy)-1-(4-methylpiperazin-1-yl)ethanone, Compound 1.128

Example 190

(R)-diethyl (3-((3-(1H-Indazol-5-ylamino)piperidin-1-yl)methyl)phenoxy)methylphosphonate, Compound 1.129

$^1$H NMR (CDCl$_3$, 300 MHz): δ 7.86 (s, 1H), 7.31-7.2 (m, 2H), 7.03 (m, 2H), 6.83 (m, 3H), 4.30 (s, 2H), 4.25 (m, 4H) 3.59 (bs, 1H), 3.49 (m, 2H), 2.76 (m, 1H), 2.45 (m, 3H), 1.75 (m, 2H) 1.59 (m, 2H) 1.36 (t, J=7.2 Hz, 6H).

Example 191

(R)—N-(1-(Benzofuran-5-ylmethyl)piperidin-3-yl)-1H-indazol-5-amine, Compound 1.131

Example 192

(R)—N-(1-(4-Chlorobenzyl)piperidin-3-yl)-1H-indazol-5-amine, Compound 1.132

Example 193

(R)—N-(1-(4-Methylbenzyl)piperidin-3-yl)-1H-indazol-5-amine, Compound 1.133

Example 194

(R)—N-(1-(4-Bromobenzyl)piperidin-3-yl)-1H-indazol-5-amine, Compound 1.134

Example 195

(R)—N-(1-(4-Ethylbenzyl)piperidin-3-yl)-1H-indazol-5-amine, Compound 1.136

Example 196

(R)—N-(1-(2,4-Dimethylbenzyl)piperidin-3-yl)-1H-indazol-5-amine, Compound 1.137

Example 197

(R)—N-(1-(Benzo[b]thiophen-5-ylmethyl)piperidin-3-yl)-1H-indazol-5-amine, Compound 1.138

Examples 198-204

Reaction of (S)—N-(piperidin-3-yl)-1H-indazol-5-amine dihydrochloride with the appropriate aldehydes using the method of Example 8 with the variation that sodium cyanoborohydride was used as reductant and methanol was used as the reaction solvent afforded the compounds in Examples 198-204:

Example 198

(S)—N-(1-(4-(Methylthio)benzyl)piperidin-3-yl)-1H-indazol-5-amine, Compound 1.075

$^1$H NMR (CDCl$_3$, 300 MHz): δ 9.8 (bs, 1H), 7.86 (s, 1H), 7.3-7.18 (m, 5H), 6.82 (m, 2H), 3.6-3.4 (m, 3H), 2.74 (m, 1H), 2.47 (s, 3H), 2.41-2.30 (m, 3H), 1.75 (m, 2H) 1.56 (m, 3H).

Example 199

(S)-2-(3-((3-(1H-Indazol-5-ylamino)piperidin-1-yl)methyl)phenoxy)ethanol, Compound 1.090

$^1$H NMR (CDCl$_3$, 300 MHz): δ 7.86 (s, 1H), 7.31-7.2 (m, 2H), 6.94 (m, 2H), 6.83 (m, 3H), 4.09 (m, 2H), 3.96 (m, 2H), 3.61 (m, 1H) 3.50 (m, 2H), 2.80 (m, 1H), 2.45 (m, 3H), 1.75 (m, 2H) 1.59 (m, 3H).

Example 200

(S)—N-(3-((3-(1H-Indazol-5-ylamino)piperidin-1-yl)methyl)phenyl)methanesulfonamide, Compound 1.091

$^1$H NMR (CDCl$_3$, 300 MHz): δ 7.86 (s, 1H), 7.32-7.25 (m, 2H), 7.09 (m, 2H), 6.87 (dd, J=2.1, 9.0 Hz, 1H), 6.79 (s, 1H), 6.32 (bs, 1H), 3.61 (m, 1H) 3.53 (dd, J=10.8, 35.1 Hz, 2H), 2.91 (s, 3H), 2.61 (m, 1H), 2.45 (m, 3H), 1.76 (m, 2H) 1.60 (m, 3H).

Example 201

(S)-2-(6-((3-(1H-Indazol-5-ylamino)piperidin-1-yl)methyl)-1H-indol-1-yl)acetamide, Compound 1.107

$^1$H NMR (CDCl$_3$, 300 MHz): δ 7.82 (s, 1H), 7.60 (d, J=8.1 Hz, 1H), 7.27-7.18 (m, 2H), 7.17 (d, J=7.5 Hz, 1H), 7.06 (d, J=3.0 Hz, 1H), 6.83 (d, J=7.8 Hz, 1H), 6.77 (s, 1H), 6.59 (d, J=3.0 Hz, 1H), 5.23 (bs, 2H), 4.78 (s, 2H), 3.70-3.57 (m, 3H), 2.78 (m, 1H), 2.45-2.35 (m, 3H), 1.76 (m, 2H), 1.60 (m, 2H).

Example 202

(S)-2-(6-((3-(1H-Indazol-5-ylamino)piperidin-1-yl)methyl)-1H-indol-1-yl)ethanol, Compound 1.109

$^1$H NMR (CDCl$_3$, 300 MHz): δ 9.80 (bs, 1H), 7.82 (s, 1H), 7.59 (m, 1H), 7.37 (s, 1H), 7.24 (s, 1H), 7.15 (m, 2H), 6.83 (m, 2H), 6.50 (m, 1H), 4.28 (m, 2H), 3.96 (m, 2H), 3.75 (m, 1H) 3.60 (m, 2H), 2.80 (m, 1H), 2.45 (m, 3H), 1.75 (m, 2H) 1.59 (m, 2H).

Example 203

(S)-3-(3-(((R)-3-(1H-Indazol-5-ylamino)piperidin-1-yl)methyl)phenoxy)propane-1,2-diol, Compound 1.113

Example 204

(S)—N-(3-((3-(1H-Indazol-5-ylamino)piperidin-1-yl)methyl)phenyl)ethanesulfonamide, Compound 1.124

$^1$H NMR (CDCl$_3$, 300 MHz): δ 9.95 (bs, 1H), 7.86 (s, 1H), 7.32-7.23 (m, 3H), 7.08 (m, 2H), 6.88 (dd, J=1.8, 8.7 Hz, 1H), 6.79 (s, 1H), 6.50 (m, 1H), 3.60 (bs, 1H), 3.43 (dd, J=13.5, 38.1 Hz, 2H), 3.06 (m, 2H), 2.68 (m, 2H), 2.45-2.35 (m, 2H), 1.76 (m, 2H), 1.60 (m, 2H), 1.28 (t, J=7.5 Hz, 3H).

Examples 205-206

Reaction of (R)—N-(pyrrolidin-3-yl)-1H-indazol-5-amine dihydrochloride with the appropriate aldehydes using the method of Example 8 with the variation that sodium cyanoborohydride was used as reductant and methanol was used as the reaction solvent afforded the compounds in Examples 205-206:

Example 205

(R)-2-(3-((3-(1H-Indazol-5-ylamino)pyrrolidin-1-yl)methyl)phenoxy)ethanol, Compound 1.096

$^1$H NMR (CDCl$_3$, 300 MHz): δ 9.80 (bs, 1H), 7.90 (s, 1H), 7.32 (m, 2H), 6.95 (m, 2H), 6.82 (m, 3H), 4.11 (m, 3H), 3.95

(m, 2H), 3.63 (m, 2H), 2.89 (m, 2H), 2.71 (m, 1H), 2.45 (m, 1H), 2.35 (m, 1H), 2.00 (m, 1H), 1.73 (m, 1H).

Example 206

(R)—N-(3-((3-(1H-Indazol-5-ylamino)pyrrolidin-1-yl)methyl)phenyl)methanesulfonamide, Compound 1.097

$^1$H NMR (CDCl$_3$, 300 MHz): δ 9.90 (bs, 1H), 7.88 (s, 1H), 7.32 (m, 2H), 7.16 (s, 1H), 7.11 (m, 2H), 6.82 (dd, J=2.1 8.7 Hz, 2H), 6.74 (d, J=1.5 Hz, 1H), 6.48 (bs, 1H), 4.11 (m, 1H), 3.63 (dd, J=13.5, 34.5 Hz, 2H), 2.93 (s, 3H), 2.89 (m, 1H), 2.71 (m, 2H), 2.45 (m, 1H), 2.35 (m, 1H), 1.73 (m, 1H).

Examples 207-208

Reaction of (S)—N-(pyrrolidin-3-yl)-1H-indazol-5-amine dihydrochloride with the appropriate aldehydes using the method of Example 8 with the variation that sodium cyanoborohydride was used as reductant and methanol was used as the reaction solvent afforded the compounds in Examples 207-208:

Example 207

(S)-2-(3-((3-(1H-Indazol-5-ylamino)pyrrolidin-1-yl)methyl)phenoxy)ethanol, Compound 1.094

$^1$H NMR (CDCl$_3$, 300 MHz): δ 9.80 (bs, 1H), 7.90 (s, 1H), 7.32 (m, 2H), 6.95 (m, 2H), 6.82 (m, 3H), 4.11 (m, 3H), 3.95 (m, 2H), 3.63 (m, 2H), 2.89 (m, 2H), 2.71 (m, 1H), 2.45 (m, 1H), 2.35 (m, 1H), 2.00 (m, 1H), 1.73 (m, 1H).

Example 208

(S)—N-(3-((3-(1H-Indazol-5-ylamino)pyrrolidin-1-yl)methyl)phenyl)methanesulfonamide, Compound 1.095

$^1$H NMR (CDCl$_3$, 300 MHz): δ 9.90 (bs, 1H), 7.88 (s, 1H), 7.32 (m, 2H), 7.16 (s, 1H), 7.11 (m, 2H), 6.82 (dd, J=2.1 8.7 Hz, 2H), 6.74 (d, J=1.5 Hz, 1H), 6.48 (bs, 1H), 4.11 (m, 1H), 3.63 (dd, J=13.5, 34.5 Hz, 2H), 2.93 (s, 3H), 2.89 (m, 1H), 2.71 (m, 2H), 2.45 (m, 1H), 2.35 (m, 1H), 1.73 (m, 1H).

Example 209

2-(3-((3-(Isoquinolin-5-ylamino)pyrrolidin-1-yl)methyl)phenoxy)ethanol, Compound 2.042

Reaction of N-(pyrrolidin-3-yl)isoquinolin-5-amine with 3-(2-hydroxyethoxy)benzaldehyde using the method of Example 8 afforded the title compound.

$^1$H NMR (CDCl$_3$, 300 MHz): δ 9.14 (s, 1H), 8.46 (d, J=6.0 Hz, 1H), 7.57 (d, J=6 Hz, 1H), 7.43 (t, J=8.1, 1H), 7.31 (d, J=8.1 Hz, 1H), 7.22 (d, J=8.1 Hz, 1H), 6.94 (m, 2H), 6.83 (m, 1H), 6.69 (d, J=7.5 Hz, 1H), 4.67 (d, J=7.5 Hz, 1H), 4.16 (m, 1H), 4.06 (m, 2H), 3.94 (m, 2H), 3.65 (s, 2H), 2.88 (m, 2H), 2.71 (dd, J=3.6, 9.6 Hz, 1H), 2.60-2.40 (m, 2H), 1.80 (m, 1H).

Examples 210-211

Reaction of (R)—N-(piperidin-3-yl)isoquinolin-5-amine with the appropriate aldehydes using the method of Example 8 afforded the compounds in Examples 210-211:

Example 210

(R)—N-(3-((3-(Isoquinolin-5-ylamino)piperidin-1-yl)methyl)phenyl)methanesulfonamide, Compound 2.033

$^1$H NMR (CDCl$_3$, 300 MHz): δ 9.15 (s, 1H), 8.52 (d, J=6.0 Hz, 1H), 7.60 (d, J=6 Hz, 1H), 7.41 (t, J=7.8 Hz, 1H), 7.30-7.18 (m, 4H), 7.03 (m, 1H), 6.72 (d, J=7.8 Hz, 1H), 5.05 (bs, 1H), 3.81 (bs, 1H), 3.55 (dd, J=13.5, 35.1 Hz, 2H), 2.99 (s, 3H), 2.65 (m, 3H), 2.35 (m, 1H), 1.85-1.60 (m, 4H).

Example 211

(R)-2-(3-((3-(Isoquinolin-5-ylamino)piperidin-1-yl)methyl)phenoxy)ethanol, Compound 2.034

$^1$H NMR (CDCl$_3$, 300 MHz): δ 9.15 (s, 1H), 8.48 (d, J=6.0 Hz, 1H), 7.57 (d, J=6 Hz, 1H), 7.42 (t, J=7.8 Hz, 1H), 7.30-7.22 (m, 2H), 6.98 (m, 2H), 6.81 (dd, J=1.8, 8.1 Hz, 1H), 6.73 (d, J=7.8 Hz, 1H), 5.05 (bs, 1H), 4.09 (m, 2H), 3.96 (m, 2H), 3.80 (bs, 1H), 3.54 (dd, J=13.2, 38.1 Hz, 2H), 2.99 (s, 3H), 2.63 (m, 2H), 2.35 (m, 1H), 2.12 (bs, 1H), 1.85-1.60 (m, 4H).

Examples 212-214

Reaction of (S)—N-(piperidin-3-yl)isoquinolin-5-amine with the appropriate aldehydes using the method of Example 8 afforded the compounds in Examples 212-214:

Example 212

(S)-2-(3-((3-(Isoquinolin-5-ylamino)piperidin-1-yl)methyl)phenoxy)ethanol, Compound 2.036

$^1$H NMR (CDCl$_3$, 300 MHz): δ 9.15 (s, 1H), 8.48 (d, J=6.0 Hz, 1H), 7.57 (d, J=6 Hz, 1H), 7.42 (t, J=7.8 Hz, 1H), 7.30-7.22 (m, 2H), 6.98 (m, 2H), 6.81 (dd, J=1.8, 8.1 Hz, 1H), 6.73 (d, J=7.8 Hz, 1H), 5.05 (bs, 1H), 4.09 (m, 2H), 3.96 (m, 2H), 3.80 (bs, 1H), 3.54 (dd, J=13.2, 38.1 Hz, 2H), 2.99 (s, 3H), 2.63 (m, 2H), 2.35 (m, 1H), 2.12 (bs, 1H), 1.85-1.60 (m, 4H).

Example 213

(S)—N-(3-((3-(Isoquinolin-5-ylamino)piperidin-1-yl)methyl)phenyl)methanesulfonamide, Compound 2.037

$^1$H NMR (CDCl$_3$, 300 MHz): δ 9.15 (s, 1H), 8.52 (d, J=6.0 Hz, 1H), 7.60 (d, J=6 Hz, 1H), 7.41 (t, J=7.8 Hz, 1H), 7.30-7.18 (m, 4H), 7.03 (m, 1H), 6.72 (d, J=7.8 Hz, 1H), 5.05 (bs, 1H), 3.81 (bs, 1H), 3.55 (dd, J=13.5, 35.1 Hz, 2H), 2.99 (s, 3H), 2.65 (m, 3H), 2.35 (m, 1H), 1.85-1.60 (m, 4H).

Examples 214-220

Reaction of (R)—N-(pyrrolidin-3-yl)isoquinolin-5-amine with the appropriate aldehydes using the method of Example 8 afforded the compounds in Examples 214-220:

Example 214

(R)—N-(1-(4-(Methylthio)benzyl)pyrrolidin-3-yl)isoquinolin-5-amine, Compound 2.026

$^1$H NMR (CDCl$_3$, 300 MHz): δ 9.14 (s, 1H), 8.46 (d, J=6.0 Hz, 1H), 7.56 (d, J=6 Hz, 1H), 7.43 (t, J=7.8 Hz, 1H), 7.31 (m,

5H), 6.68 (d, J=7.5 Hz, 1H), 4.66 (d, J=7.2 Hz, 1H), 4.18 (m, 1H), 3.64 (s, 2H), 2.88 (m, 2H), 2.71 (dd, J=3.6, 9.6 Hz, 1H), 2.60-2.40 (m, 2H), 2.47 (s, 3H), 2.05 (bs, 1H), 1.85 (m, 1H).

Example 215

(R)—N-(3-((3-(Isoquinolin-5-ylamino)pyrrolidin-1-yl)methyl)phenyl)methanesulfonamide, Compound 2.038

$^1$H NMR (CDCl$_3$, 300 MHz): δ 9.15 (s, 1H), 8.47 (d, J=6.0 Hz, 1H), 7.58 (d, J=6 Hz, 1H), 7.43 (t, J=8.1, 1H), 7.31 (m, 3H), 7.14 (m, 2H), 6.69 (d, J=7.5 Hz, 1H), 4.66 (d, J=7.2 Hz, 1H), 4.16 (m, 1H), 3.65 (dd, J=13.2, 19.5 Hz, 2H), 2.95 (s, 3H), 2.89-2.72 (m, 3H), 2.60-2.40 (m, 2H), 1.80 (m, 1H).

Example 216

(R)-2-(3-((3-(Isoquinolin-5-ylamino)pyrrolidin-1-yl)methyl)phenoxy)ethanol, Compound 2.039

$^1$H NMR (CDCl$_3$, 300 MHz): δ 9.14 (s, 1H), 8.46 (d, J=6.0 Hz, 1H), 7.57 (d, J=6 Hz, 1H), 7.43 (t, J=8.1, 1H), 7.31 (d, J=8.1 Hz, 1H), 7.22 (d, J=8.1 Hz, 1H), 6.94 (m, 2H), 6.83 (m, 1H), 6.69 (d, J=7.5 Hz, 1H), 4.67 (d, J=7.5 Hz, 1H), 4.16 (m, 1H), 4.06 (m, 2H), 3.94 (m, 2H), 3.65 (s, 2H), 2.88 (m, 2H), 2.71 (dd, J=3.6, 9.6 Hz, 1H), 2.60-2.40 (m, 2H), 1.80 (m, 1H).

Example 217

(R)-2-(3-((3-(Isoquinolin-5-ylamino)pyrrolidin-1-yl)methyl)phenoxy)acetamide, Compound 2.040

$^1$H NMR (CD$_3$OD, 300 MHz): δ 9.05 (s, 1H), 8.32 (d, J=6.0 Hz, 1H), 7.98 (d, J=6 Hz, 1H), 7.48 (t, J=8.1, 1H), 7.33 (d, J=8.1 Hz, 1H), 7.28 (t, J=8.1 Hz, 1H), 7.01 (m, 2H), 6.91 (m, 1H), 6.78 (d, J=7.5 Hz, 1H), 4.49 (s, 2H), 4.21 (m, 1H), 3.70 (s, 2H), 3.01 (m, 1H), 2.85 (m, 1H), 2.74-2.60 (m, 2H), 2.45 (m, 1H), 1.88 (m, 1H).

Example 218

(R)—N-(3-((3-(Isoquinolin-5-ylamino)pyrrolidin-1-yl)methyl)phenyl)ethanesulfonamide, Compound 2.041

$^1$H NMR (CDCl$_3$, 300 MHz): δ 9.14 (s, 1H), 8.45 (d, J=6.0 Hz, 1H), 7.60 (d, J=6 Hz, 1H), 7.43 (t, J=8.1, 1H), 7.31 (m, 3H), 7.12 (d, J=7.5 Hz, 2H), 6.69 (d, J=7.5 Hz, 1H), 4.67 (m, 1H), 4.16 (m, 1H), 3.65 (dd, J=13.2, 21.6 Hz, 2H), 3.07 (q, J=7.2 Hz, 2H), 2.89 (m, 1H), 2.75 (m, 2H), 2.60-2.40 (m, 2H), 1.80 (m, 1H), 1.30 (t, J=7.2 Hz, 3H).

Example 219

(R)-2-(3-((3-(Isoquinolin-5-ylamino)pyrrolidin-1-yl)methyl)phenoxy)-1-morpholinoethanone, Compound 2.043

Example 220

(R)-2-(3-((3-(Isoquinolin-5-ylamino)pyrrolidin-1-yl)methyl)phenoxy)acetic acid, Compound 2.044

Prepared by coupling of the corresponding tert-butyl ester, followed by deprotection using the method of Example 4.

Examples 220-222

Reaction of (S)—N-(pyrrolidin-3-yl)isoquinolin-5-amine with the appropriate aldehydes using the method of Example 8 afforded the compounds in Examples 220-222:

Example 221

(S)-2-(3-((3-(Isoquinolin-5-ylamino)pyrrolidin-1-yl)methyl)phenoxy)ethanol, Compound 2.032

$^1$H NMR (CDCl$_3$, 300 MHz): δ 9.14 (s, 1H), 8.46 (d, J=6.0 Hz, 1H), 7.57 (d, J=6 Hz, 1H), 7.43 (t, J=8.1, 1H), 7.31 (d, J=8.1 Hz, 1H), 7.22 (d, J=8.1 Hz, 1H), 6.94 (m, 2H), 6.83 (m, 1H), 6.69 (d, J=7.5 Hz, 1H), 4.67 (d, J=7.5 Hz, 1H), 4.16 (m, 1H), 4.06 (m, 2H), 3.94 (m, 2H), 3.65 (s, 2H), 2.88 (m, 2H), 2.71 (dd, J=3.6, 9.6 Hz, 1H), 2.60-2.40 (m, 2H), 1.80 (m, 1H).

Example 222

(S)—N-(3-((3-(Isoquinolin-5-ylamino)pyrrolidin-1-yl)methyl)phenyl)methanesulfonamide, Compound 2.035

$^1$H NMR (CDCl$_3$, 300 MHz): δ 9.15 (s, 1H), 8.47 (d, J=6.0 Hz, 1H), 7.58 (d, J=6 Hz, 1H), 7.43 (t, J=8.1, 1H), 7.31 (m, 3H), 7.14 (m, 2H), 6.69 (d, J=7.5 Hz, 1H), 4.66 (d, J=7.2 Hz, 1H), 4.16 (m, 1H), 3.65 (dd, J=13.2, 19.5 Hz, 2H), 2.95 (s, 3H), 2.89-2.72 (m, 3H), 2.60-2.40 (m, 2H), 1.80 (m, 1H).

Example 223

Rho Kinase Inhibition Assay

Inhibition of ROCK2 activity was determined using the IMAP™ Screening Express Kit (Molecular Devices product number #8073). ROCK2 kinase (UpstateChemicon #14-451) and Flourescein tagged substrate peptide Fl-AKRRRLSS-LRA (Molecular Devices product number R7184) was pre-incubated with test compound for 5 minutes in buffer containing 10 mM Tris-HCl pH 7.2, 10 mM MgCl$_2$, and 0.1% BSA. Following the preincubation, 10 μM ATP was added to initiate the reaction. After 60 minutes at room temperature, Molecular Devices IMAP™ binding solution was added to bind phosphorylated substrate. After 30 minutes of incubation in the presence of the IMAP™ beads the fluorescence polarization was read and the ratio was reported as mP. IC$_{50}$ results were calculated using the Prism software from Graphpad.

This assay demonstrates a compound's ability to inhibit ROCK2 in an in vitro setting using the isolated enzyme. Most of the compounds studied inhibited ROCK2 with an IC$_{50}$ below 10 μM, many of these inhibiting below 1 μM. The most potent compounds in this assay showed IC$_{50}$ values below 250 nM. Compounds having ROCK2 IC$_{50}$ values on the order of 2 μM or below have been shown to possess efficacy in numerous studies using in vivo models of the disease processes described in this application, specifically in models of elevated IOP and glaucoma. See Tian et al., *Arch. Ophthalmol.* 116: 633-643, 1998; Tian et al., *Invest. Ophthalmol. Vis. Sci.* 40: 239-242, 1999; Tian, et al., *Exp. Eye Res.* 68: 649-655; 1999; Sabanay, et al., *Arch. Ophthalmol.* 118: 955-962, 2000; Volberg, et al., *Cell Motil. Cytoskel.* 29: 321-338, 1994; Tian, et al., *Exp. Eye Res.* 71: 551-566, 2000; Tokushige, et al., *Invest. Ophthalmol. Vis. Sci.* 48: 3216-3222, 2007; Honjo, et al., *Invest. Ophthalmol. Vis. Sci.* 42: 137-144, 2001.

TABLE II

Rho Kinase Assay Data.

| Compound | ROCK2 IC$_{50}$, nM |
|---|---|
| 1.001 | 358 |
| 1.002 | 1,230 |
| 1.003 | 6,190 |
| 1.004 | 254 |
| 1.005 | 2,290 |
| 1.006 | 2,750 |
| 1.007 | 3,440 |
| 1.008 | 65.8 |
| 1.009 | 1,610 |
| 1.010 | 2,800 |
| 1.011 | 12,200 |
| 1.012 | 12,200 |
| 1.013 | 3,660 |
| 1.014 | 4,690 |
| 1.015 | 9,980 |
| 1.016 | 135 |
| 1.017 | 215 |
| 1.018 | 2,410 |
| 1.019 | 13,400 |
| 1.020 | 251 |
| 1.021 | 553 |
| 1.022 | 1,610 |
| 1.023 | 334 |
| 1.024 | 107 |
| 1.025 | 588 |
| 1.026 | 2,130 |
| 1.027 | 6,600 |
| 1.028 | 1,310 |
| 1.029 | 11,700 |
| 1.031 | 1,750 |
| 1.032 | 1,940 |
| 1.033 | 86.9 |
| 1.034 | 69.1 |
| 1.035 | 208 |
| 1.036 | 1,020 |
| 1.037 | 69.5 |
| 1.038 | 2,760 |
| 1.039 | 328 |
| 1.040 | 144 |
| 1.041 | 137 |
| 1.042 | 4,400 |
| 1.043 | 11,700 |
| 1.044 | 6,510 |
| 1.045 | 586 |
| 1.046 | 156 |
| 1.047 | 57.0 |
| 1.048 | 721 |
| 1.049 | 604 |
| 1.050 | 1,040 |
| 1.051 | 62.6 |
| 1.052 | 15.3 |
| 1.053 | 189 |
| 1.054 | 132 |
| 1.055 | 472 |
| 1.056 | 435 |
| 1.057 | 194 |
| 1.058 | 47.5 |
| 1.059 | 32.0 |
| 1.060 | 87.2 |
| 1.061 | 282 |
| 1.062 | 155 |
| 1.063 | 223 |
| 1.064 | 165 |
| 1.065 | 326 |
| 1.066 | 232 |
| 1.067 | 1,850 |
| 1.068 | 660 |
| 1.069 | 6,050 |
| 1.070 | 6,680 |
| 1.071 | 5,590 |
| 1.072 | 58.5 |
| 1.073 | 111 |
| 1.074 | 71.6 |
| 1.075 | 74.5 |
| 1.076 | 111 |
| 1.077 | 53.1 |
| 1.078 | 63.1 |
| 1.079 | 102 |
| 1.080 | 162 |
| 1.081 | 30.1 |
| 1.082 | 30.4 |
| 1.083 | 7,310 |
| 1.084 | 274 |
| 1.085 | 1,680 |
| 1.086 | 310 |
| 1.087 | 280 |
| 1.088 | 651 |
| 1.089 | 29.4 |
| 1.090 | 354 |
| 1.091 | 49.4 |
| 1.092 | 406 |
| 1.093 | 101 |
| 1.094 | 466 |
| 1.095 | 647 |
| 1.096 | 1,300 |
| 1.097 | 276 |
| 1.098 | 250 |
| 1.099 | 25.8 |
| 1.100 | 42.9 |
| 1.101 | 68.5 |
| 1.102 | 34.3 |
| 1.104 | 107 |
| 1.105 | 172 |
| 1.106 | 69.2 |
| 1.107 | 148 |
| 1.108 | 367 |
| 1.109 | 242 |
| 1.111 | 591 |
| 1.112 | 2,030 |
| 1.113 | 859 |
| 1.114 | 1,490 |
| 1.115 | 555 |
| 1.116 | 862 |
| 1.117 | 323 |
| 1.118 | 1,400 |
| 1.119 | 3,630 |
| 1.120 | 109 |
| 1.121 | 578 |
| 1.122 | 254 |
| 1.123 | 135 |
| 1.124 | 59.2 |
| 1.125 | 879 |
| 1.130 | 2,710 |
| 2.001 | 98.8 |
| 2.002 | 2,580 |
| 2.003 | 5,720 |
| 2.004 | 3,710 |
| 2.005 | 1,780 |
| 2.006 | 73.9 |
| 2.007 | 3,620 |
| 2.008 | 3,650 |
| 2.009 | 368 |
| 2.010 | 1,240 |
| 2.011 | 4,090 |
| 2.012 | 14,900 |
| 2.013 | 1,490 |
| 2.014 | 1,670 |
| 2.015 | 4,190 |
| 2.016 | 716 |
| 2.017 | 322 |
| 2.018 | 632 |
| 2.019 | 4,080 |
| 2.020 | 820 |
| 2.021 | 1,900 |
| 2.022 | 311 |
| 2.023 | 15,700 |
| 2.024 | 8,920 |
| 2.025 | 29.9 |
| 2.026 | 6,330 |
| 2.027 | 120 |
| 2.028 | 789 |
| 2.029 | 3,140 |

TABLE II-continued

Rho Kinase Assay Data.

| Compound | ROCK2 $IC_{50}$, nM |
|---|---|
| 2.030 | 2,460 |
| 2.031 | 87.1 |
| 2.032 | 5,330 |
| 2.033 | 3,060 |
| 2.034 | 4,010 |
| 2.035 | 3,240 |
| 2.036 | 160 |
| 2.037 | 3,060 |
| 2.038 | 112 |
| 2.039 | 101 |
| 2.040 | 273 |
| 2.041 | 168 |
| 2.043 | 383 |
| 2.044 | 433 |

Example 224

NIH/3T3 Cell Morphology Assay

NIH/3T3 cells were grown in DMEM-H containing glutamine and 10% Colorado Calf Serum. Cells were passaged regularly prior to reaching confluence. Eighteen to 24 hours prior to experimentation, the cells were plated onto Poly-L-Lysine-coated glass bottom 24-well plates. On the day of experimentation, the cell culture medium was removed and was replaced with the same medium containing from 10 nM to 25 µM of the test compound, and the cells were incubated for 60 minutes at 37° C. The culture medium was then removed and the cells were washed with warmed PBS and fixed for 10 minutes with warmed 4% paraformaldehyde. The cells were permeabilized with 0.5% Triton-X, stained with TRITC-conjugated phalloidin and imaged using a Nikon Eclipse E600 epifluorescent microscope to determine the degree of actin disruption. Results were expressed as a numerical score indicating the observed degree of disruption of the actin cytoskeleton at the test concentration, ranging from 0 (no effect) to 4 (complete disruption), and were the average of at least 2 determinations.

All compounds tested show measurable activity in the cell morphology assay, with most of the compounds providing substantial effects on the actin cytoskeleton at the testing concentration (score of 2 at 1 µM). The assay demonstrates that a compound's in vitro ROCK inhibition activity can manifest itself in morphology changes, such as actin stress fiber disassembly and alteration in focal adhesions in intact cells leading to inhibition of acto-myosin driven cellular contraction. These morphology changes are thought to provide the basis for the beneficial pharmacological effects sought in the setting of the disease processes described in this application, specifically the lowering of elevated IOP in hypertensive eyes via increased outflow through the trabecular meshwork.

TABLE III

Cell Morphology Assay Data.

| Compound | Cell score at 1 µM |
|---|---|
| 1.002 | 1.4 |
| 1.004 | 1.8 |
| 1.005 | 1.3 |
| 1.006 | 2 |
| 1.008 | 2 |
| 1.024 | 2.4 |
| 1.025 | 2 |
| 1.034 | 2 |
| 1.039 | 2 |
| 1.041 | 2.5 |
| 1.046 | 2.5 |
| 1.048 | 1.5 |
| 1.051 | 2.5 |
| 1.052 | 2.8 |
| 1.062 | 2.3 |
| 1.066 | 2 |
| 2.002 | 1.8 |
| 2.006 | 2.8 |
| 2.008 | 1 |
| 2.016 | 1.8 |
| 2.017 | 2 |
| 2.018 | 1.8 |
| 2.026 | 2 |

Example 225

Ocular Pharmacokinetic Assay

Intraocular fluid (aqueous humor) was collected from New Zealand White rabbits to determine corneal and anterior chamber pharmacokinetics of formulations containing Compound 1.008, 1.039, and 1.051. Each animal was dose bilaterally with 2×10 µl of 25 mM of each test compound (in 10 mM acetate buffered saline, 0.01% benzalkonium chloride, 0.05% EDTA, pH 4.5) or with vehicle. During instillation, the upper and lower eyelids were immobilized and the compound was administered to the superior aspect of the globe allowing it to flow across the ocular surface. Following instillation, blinking was prevented for 30 seconds. Aqueous humor was collected from 30 minutes to 8 hours following topical instillation using a 30-gauge needle inserted proximal to the corneal scleral limbus. Subsequently 30 µl of aqueous humor was aspirated using a 300 µl syringe. Aqueous humor samples were assayed for the concentration of the test compound using an LC/MS/MS assay system. All experiments were conducted in accordance with the ARVO Statement for the Use of Animals in Ophthalmic and Vision Research and in compliance with National Institutes of Health. The results of observed aqueous humor concentrations of the test compounds at 0.5, 2, and 4 hours after instillation in the animal eyes are shown in FIG. 1.

This pharmacokinetic assay shows that the compounds of the invention when dosed topically are able to penetrate the eye and achieve concentrations in the aqueous humor adequate to provide substantial ROCK inhibition at the sight of action, that is, concentrations at or above the ROCK $IC_{50}$ of the compound in question. Further, it shows that these compounds can show different pharmacokinetic profiles on topical ocular dosing, with some compounds showing a more prolonged presence, while others penetrate rapidly into the eye and are quickly cleared from the aqueous humor.

Example 226

Intraocular Pressure Pharmacodynamic Assay

Adult cynomolgus monkeys of both sexes were studied. All experiments were conducted in accordance with the ARVO Statement for the Use of Animals in Ophthalmic and Vision Research and in compliance with National Institutes of Health.

Prior to study inclusion a trained ophthalmologist performed a slit lamp examination to determine the integrity of the corneal epithelium and endothelium, presence of flare or cells in the AC, and clarity of the lens. All animals were free of ocular abnormalities when studied.

Figures 1, 2:
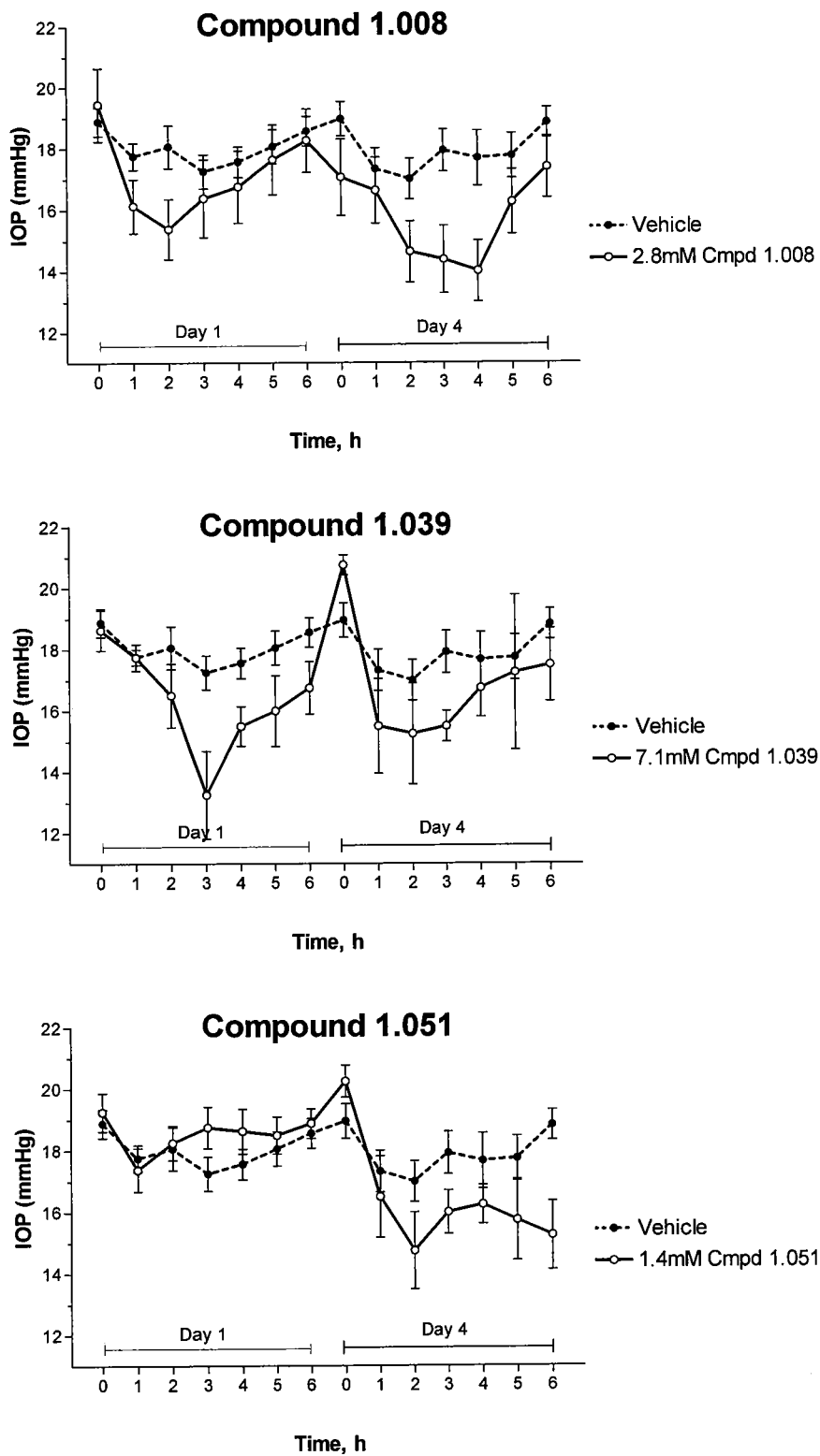
Figure 2:
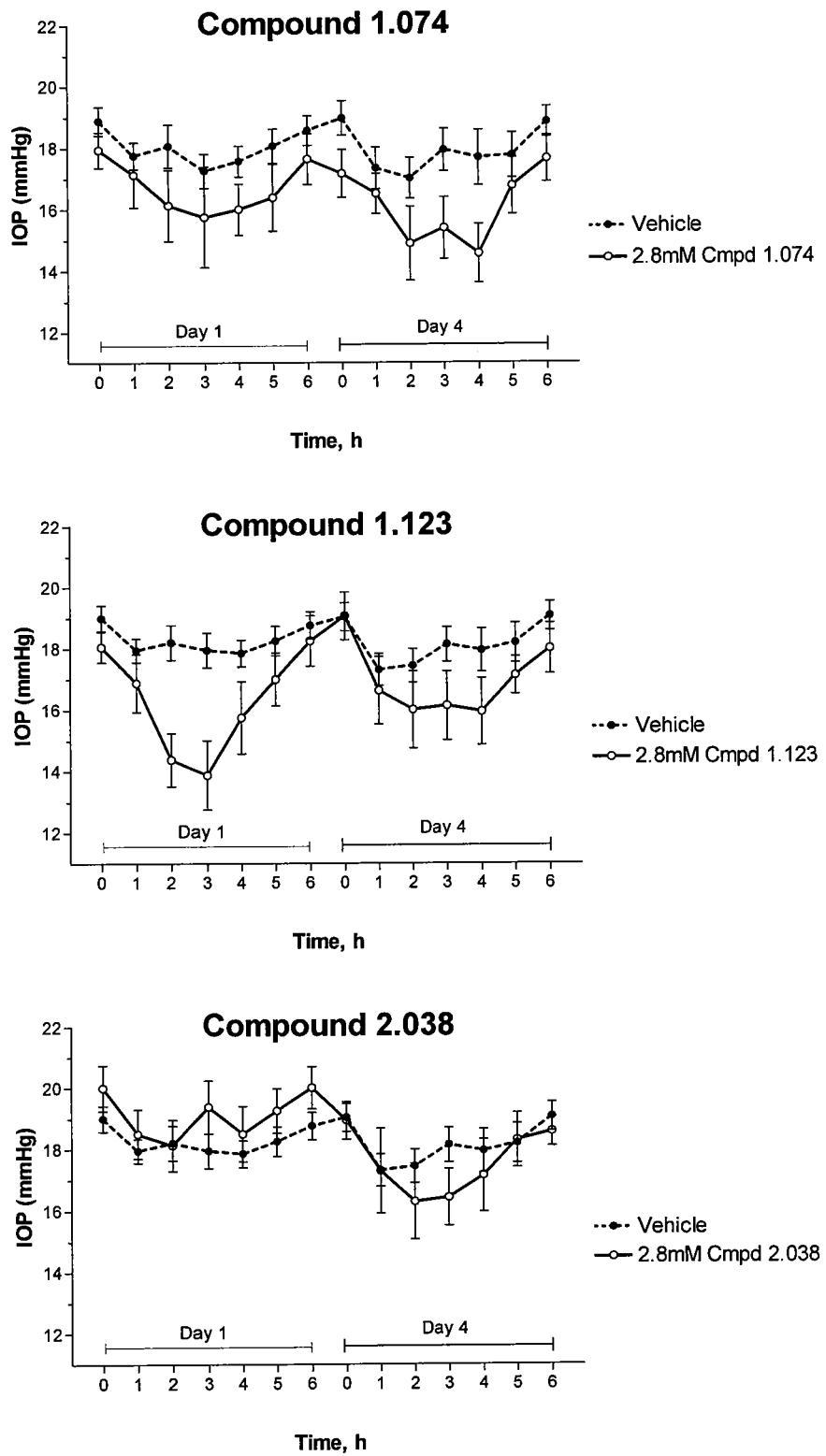
Figures 2, 3:
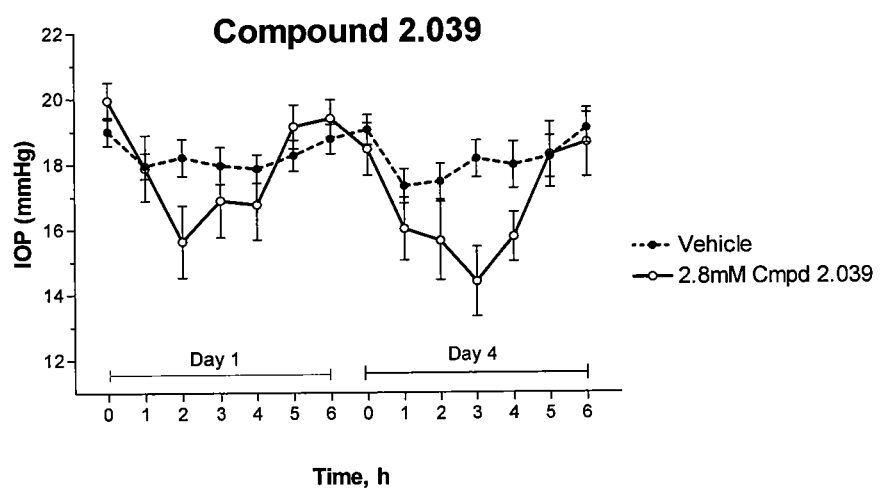

Following baseline IOP measurements, freshly prepared formulations containing vehicle (10 mM acetate buffered saline containing 0.01% benzalkonium chloride and 0.05% EDTA, pH 4.5) and one of the compounds 1.008 (2.8 mM), 1.039 (7.1 mM), 1.051 (1.4 mM), 1.074 (2.8 mM), 1.123 (2.8 mM), 2.038 (2.8 mM), or 2.039 (2.8 mM), or vehicle alone were topically administered to the central cornea of supine animals as two 20 µl drops at 30 second intervals with blinking prevented between drops. Animals were treated twice daily for 3.5 days at 8 AM and 4 PM. Following administration, IOP was measured every hour for 6 hours using a minified Goldmann applanation tonometer. Slit lamp exams were conducted at 3 and 6 hours. The intraocular pressure of animals after treatment with the test compounds or vehicle at day 1 and day 4 from hour 0 to hour 6 is shown in FIGS. 2-1 to 2-3.

This pharmacodynamic assay shows that the compounds of the invention are able to achieve meaningful reductions in intraocular pressure when dosed topically in normotensive primates. It further shows that these compounds are well-tolerated on the ocular surface when dosed in a therapeutically relevant fashion. Reduction in intraocular pressure in this way is the primary objective of current glaucoma therapy. The assay described here is the most widely accepted method for the preclinical evaluation of intraocular pressure lowering agents.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A compound of Formula II:

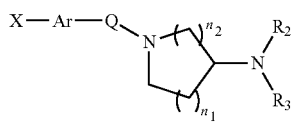

Formula II wherein:
Q is $(CR_4R_5)_{n3}$;
$n_1$ is 2;
$n_2$ is 1;
$n_3$ is 1, 2, or 3;
R2 is 5-indazolyl
Ar is a monocyclic aryl or bicyclic aryl;
X is from 1 to 3 substituents on Ar, and each is independently selected from the group consisting of $OR_8$, $NR_8R_9$, $SR_8$, $SOR_8$, $SO_2R_8$, $SO_2NR_8R_9$, $NR_8SO_2R_9$, $CONR_8R_9$, $NR_8C(\!=\!O)R_9$, $NR_8C(\!=\!O)OR_9$, $OC(\!=\!O)NR_8R_9$, and $NR_8C(\!=\!O)NR_9R_{10}$, $R_3$ is H;
$R_4$ is H;
$R_5$ is H or alkyl;
$R_8$-$R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents selected from the group consisting of $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(\!=\!O)R_{12}$, $NR_{11}C(\!=\!O)OR_{12}$, $OC(\!=\!O)NR_{11}R_{12}$, and $NR_{11}C(\!=\!O)NR_{12}R_{13}$;
wherein any two of the groups $R_8$, $R_9$ and $R_{10}$ are optionally joined with a link selected from the group consisting of bond, —O—, —S—, —SO—, —$SO_2$—, and —$NR_{17}$— to form a ring;
$R_{11}$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle;
with the proviso that if X is acyclic and is connected to Ar by an oxygen or nitrogen atom, then X contains at least one additional oxygen, nitrogen or sulfur atom.

2. The compound according to claim 1, wherein Q is $CH_2$, and $R_3$ is H.

3. The compound according to claim 1, wherein $R_5$ is H.

4. The compound of claim 1, wherein $R_8$ is H, alkyl, arylalkyl, cycloalkylalkyl, optionally substituted with $OR_{11}$, $NR_{11}SO_2R_{12}$, or $CONR_{11}R_{12}$.

5. The compound of claim 1, wherein Ar is phenyl.

6. The compound of claim 5, wherein X is from 1 to 3 substituents on Ar, and one of X is $OR_8$, or $NR_8SO_2R_9$.

7. A compound selected from the group consisting of: Compound 1.001, which is N-(1-(4-(methylsulfonyl)benzyl)piperidin-3-yl)-1H-indazol-5-amine; Compound 1.002, which is 3-((3-(1H-indazol-5-ylamino)piperidin-1-yl)methyl)benzonitrile; Compound 1.003, which is N-(4-((3-(1H-indazol-5-ylamino)piperidin-1-yl)methyl)phenyl)acetamide; Compound 1.018, which is 2-(4-((3-(1H-indazol-5-ylamino)piperidin-1-yl)methyl)phenoxy)ethanol; Compound 1.039, which is 2-(3-((3-(1H-indazol-5-ylamino)piperidin-1-yl)methyl)phenoxy)ethanol; Compound 1.048, which is N-(1-(3-(methylsulfonyl)benzyl)piperidin-3-yl)-1H-indazol-5-amine; Compound 1.051, which is N-(3-((3-(1H-indazol-5-ylamino)piperidin-1-yl)methyl)phenyl)methanesulfonamide; Compound 1.055, which is 3-((3-(1H-indazol-5-ylamino)piperidin-1-yl)methyl)benzamide; Compound 1.056, which is 3-((3-(1H-indazol-5-ylamino)piperidin-1-yl)methyl)benzenesulfonamide; Compound 1.060, which is ethyl 2-(3-((3-(1H-indazol-5-ylamino)piperidin-1-yl)methyl)phenoxy)acetate; Compound 1.084, which is 3-(3-((3-(1H-indazol-5-ylamino)piperidin-1-yl)methyl)phenoxy)propan-1-ol; Compound 1.085, which is N-(1-(3-(2-aminoethoxy)benzyl)piperidin-3-yl)-1H-indazol-5-amine; Compound 1.086, which is 2-(3-((3-(1H-indazol-5-ylamino)piperidin-1-yl)methyl)phenoxy)acetic acid; Compound 1.090, which is (S)-2-(3-((3-(1H-indazol-5-ylamino)piperidin-1-yl)methyl)phenoxy)ethanol; Compound 1.091, which is (S)—N-(3-((3-(1H-indazol-5-ylamino)piperidin-1-yl)methyl)phenyl)methanesulfonamide; Compound 1.092, which is (R)-2-(3-((3-(1H-indazol-5-ylamino)piperidin-1-yl)methyl)phenoxy)ethanol; Compound 1.093, which is (R)—N-(3-((3-(1H-indazol-5-ylamino)piperidin-1-yl)methyl)phenyl)methanesulfonamide; Compound 1.098, which is 2-(3-((3-(1H-indazol-5-ylamino)piperidin-1-yl)methyl)phenoxy)acetamide; Compound 1.111, which is N-(2-(3-((3-(1H-indazol-5-ylamino)piperidin-1-yl)methyl)phenoxy)ethyl)acetamide; Compound 1.113, which is (S)-3-(3-(((R)-3-(1H-indazol-5-ylamino)piperidin-1-yl)methyl)phenoxy)propane-1,2-diol; Compound 1.115, which is (R)-3-(3-(((R)-3-(1H-indazol-5-ylamino)piperidin-1-yl)methyl)phenoxy)propane-1,2-diol; Compound 1.116, which is (R)-1-(3-(((R)-3-(1H-indazol-5-ylamino)piperidin-1-yl)methyl)phenoxy)propan-2-ol; Compound 1.117, which is (R)-3-(3-(((S)-3-(1H-indazol-5-ylamino)piperidin-1-yl)methyl)phenoxy)propane-1,2-diol; Compound 1.118, which is (R)-1-(3-(((S)-3-(1H-indazol-5-ylamino)piperidin-1-yl)methyl)phenoxy)propan-2-ol; Compound 1.120, which is N-(3-((3-(1H-indazol-5-ylamino)piperidin-1-yl)methyl)phenyl)ethanesulfonamide; Compound 1.121, which is N-(3-((3-(1H-indazol-5-ylamino)piperidin-1-yl)methyl)phenyl)-N-methylmethanesulfonamide; Compound 1.123, which is (R)—N-(3-((3-(1H-indazol-5-ylamino)piperidin-1-yl)methyl)phenyl)ethanesulfonamide; Compound 1.124, which is (S)—N-(3-((3-(1H-indazol-5-ylamino)piperidin-1-yl)methyl)phenyl)ethanesulfonamide; Compound 1.125, which is (R)-2-(3-((3-(1H-indazol-5-ylamino)piperidin-1-yl)methyl)phenoxy)acetic acid; Compound 1.130, which is 2-(3-((4-(1H-indazol-5-ylamino)piperidin-1-yl)methyl)phenoxy)ethanol; Compound 1.008, which is N-(1-(4-(methylthio)benzyl)piperidin-3-yl)-1H-indazol-5-amine; Compound 1.017, which is N-(1-(4-(ethylthio)benzyl)piperidin-3-yl)-1H-indazol-5-amine; Compound 1.026, which is N-(1-(4-(cyclopropylthio)benzyl)piperidin-3-yl)-1H-indazol-5-amine; Compound 1.040, which is N-(1-(3-(methylthio)benzyl)piperidin-3-yl)-1H-indazol-5-amine; Compound 1.074, which is (R)—N-(1-(4-(methylthio)benzyl)piperidin-3-yl)-1H-indazol-5-amine; and Compound 1.075, which is (S)—N-(1-(4-(methylthio)benzyl)piperidin-3-yl)-1H-indazol-5-amine.

8. A method for reducing intraocular pressure in a subject in need thereof, comprising the steps of:
identifying a subject in need thereof, and
administering to the subject the compound according to claim 1, in an amount effective to inhibit actomyosin interactions.

9. A compound of Formula II:

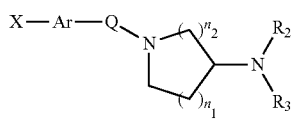

Formula II wherein:
Q is $(CR_4R_5)_{n3}$;
$n_1$ is 2;
$n_2$ is 1;
$n_3$ is 1, 2, or 3;
R2 is 5-indazolyl
Ar is a monocyclic aryl or bicyclic aryl;
X is from 1 to 3 substituents on Ar, each independently in the form Y-Z, in which Z is attached to Ar;
Y is one or more substituents on Z, and each is independently selected from the group consisting of H, halogen, $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, and $NR_8C(=O)NR_9R_{10}$;

Z is alkenyl, alkynyl, aryl, arylalkyl, arylalkenyl, arylalkynyl, heteroaryl, heteroarylalkyl, heteroarylalkenyl, heteroarylalkynyl, cycloalkyl, cycloalkenyl, cycloalkylalkyl, cycloalkylalkenyl, cycloalkylalkynyl, heterocycle, (heterocycle)alkyl, (heterocycle)alkenyl, and (heterocycle)alkynyl;
$R_3$ is H;
$R_4$ is H;
$R_5$ is H or alkyl;
$R_8$-$R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents selected from the group consisting of $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, and $NR_{11}C(=O)NR_{12}R_{13}$;
wherein any two of the groups $R_8$, $R_9$ and $R_{10}$ are optionally joined with a link selected from the group consisting of bond, —O—, —S—, —SO—, —SO$_2$—, and —NR$_{17}$— to form a ring; and
$R_{11}$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle.

10. The compound according to claim 9, wherein said compound is selected from the group consisting of: Compound 1.009, which is N-(1-(biphenyl-4-ylmethyl)piperidin-3-yl)-1H-indazol-5-amine; Compound 1.010, which is N-(1-(1H-imidazol-1-yl)benzyl)piperidin-3-yl)-1H-indazol-5-amine; Compound 1.011, which is N-(1-(4-(pyrrolidin-1-yl)benzyl)piperidin-3-yl)-1H-indazol-5-amine; Compound 1.012, which is N-(1-(4-morpholinobenzyl)piperidin-3-yl)-1H-indazol-5-amine; Compound 1.020, which is N-(1-(4-cyclopropylbenzyl)piperidin-3-yl)-1H-indazol-5-amine; Compound 1.021, which is N-(1-(3-cyclopropylbenzyl)piperidin-3-yl)-1H-indazol-5-amine; Compound 1.030, which is N-(1-(4-(thiophen-2-yl)benzyl)piperidin-3-yl)-1H-indazol-5-amine; Compound 1.034, which is N-(1-(4-ethynylbenzyl)piperidin-3-yl)-1H-indazol-5-amine; Compound 1.037, which is N-(1-(4-vinylbenzyl)piperidin-3-yl)-1H-indazol-5-amine; Compound 1.042, which is 3-(4-((3-(1H-indazol-5-ylamino)piperidin-1-yl)methyl)phenyl)prop-2-yn-1-ol; Compound 1.043, which is 4-(4-((3-(1H-indazol-5-ylamino)piperidin-1-yl)methyl)phenyl)but-3-yn-1-ol; Compound 1.044, which is N-(1-(4-(cyclopropylethynyl)benzyl)piperidin-3-yl)-1H-indazol-5-amine; Compound 1.047, which is N-(1-(3-ethynylbenzyl)piperidin-3-yl)-1H-indazol-5-amine; Compound 1.076, which is (R)—N—(1-(4-ethynylbenzyl)piperidin-3-yl)-1H-indazol-5-amine; Compound 1.077, which is (S)—N-(1-(4-ethynylbenzyl)piperidin-3-yl)-1H-indazol-5-amine.

11. The compound of claim 9, wherein Ar is phenyl.
12. The compound of claim 11, wherein one of Y is halogen, $OR_8$, or $NR_8SO_2R_9$.
13. The compound of claim 12, wherein $R_8$ is H, alkyl, arylalkyl, cycloalkylalkyl, optionally substituted with $OR_{11}$, $NR_{11}SO_2R_{12}$, or $CONR_{11}R_{12}$.

14. A method for reducing intraocular pressure in a subject in need thereof, comprising the steps of:
identifying a subject in need thereof, and
administering to the subject the compound according to claim 10, in an amount effective to inhibit actomyosin interactions.

15. A compound of Formula II:

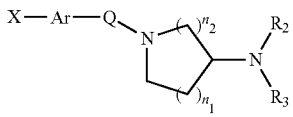

Formula II wherein:
Q is $(CR_4R_5)_{n3}$;
$n_1$ is 2;
$n_2$ is 1;
$n_3$ is 1, 2, or 3;
R2 is 5-indazolyl
Ar is a monocyclic aryl or bicyclic aryl;
X is from 1 to 3 substituents on Ar, each independently in the form Y-Z, in which Z is attached to Ar;
Y is one or more substituents on Z, and each is independently $OR_8$, $NR_8R_9$, $NO_2$, $SR_8$, $SOR_8$, $SO_2R_8$, $SO_2NR_8R_9$, $NR_8SO_2R_9$, $OCF_3$, $CONR_8R_9$, $NR_8C(=O)R_9$, $NR_8C(=O)OR_9$, $OC(=O)NR_8R_9$, or $NR_8C(=O)NR_9R_{10}$,
Z is alkyl;
$R_3$ is H;
$R_4$ is H;
$R_5$ is H or alkyl;
$R_8$-$R_{10}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle; optionally substituted by one or more halogen or heteroatom-containing substituents selected from the group consisting of $OR_{11}$, $NR_{11}R_{12}$, $NO_2$, $SR_{11}$, $SOR_{11}$, $SO_2R_{11}$, $SO_2NR_{11}R_{12}$, $NR_{11}SO_2R_{12}$, $OCF_3$, $CONR_{11}R_{12}$, $NR_{11}C(=O)R_{12}$, $NR_{11}C(=O)OR_{12}$, $OC(=O)NR_{11}R_{12}$, and $NR_{11}C(=O)NR_{12}R_{13}$;
wherein any two of the groups $R_8$, $R_9$ and $R_{10}$ are optionally joined with a link selected from the group consisting of bond, —O—, —S—, —SO—, —SO_2—, and —NR_{17}— to form a ring; and
$R_{11}$-$R_{13}$ are independently H, alkyl, alkenyl, alkynyl, aryl, arylalkyl, arylalkenyl, arylalkynyl, cycloalkyl, cycloalkenyl, cycloalkylalkyl, cycloalkylalkenyl, cycloalkylalkynyl, heteroaryl, heteroarylalkyl, heteroarylalkenyl, heteroarylalkynyl, (heterocycle)alkyl, (heterocycle)alkenyl, (heterocycle)alkynyl, or heterocycle;
with the proviso that when Y falls on the carbon by which Z is attached to Ar, then Y contains at least one nitrogen or sulfur atom.

16. The compound according to claim 15, wherein said compound is selected from the group consisting of: Compound 1.019, which is N-(1-(4-((dimethylamino)methyl)benzyl)piperidin-3-yl)-1H-indazol-5-amine; Compound 1.027, which is tert-butyl 4-((3-(1H-indazol-5-ylamino)piperidin-1-yl)methyl)benzylcarbamate; Compound 1.028, which is N-(1-(4-(methylthiomethyl)benzyl)piperidin-3-yl)-1H-indazol-5-amine; Compound 1.029, which is N-(1-(4-(methylsulfonylmethyl)benzyl)piperidin-3-yl)-1H-indazol-5-amine; Compound 1.035, which is N-(1-(4-(aminomethyl)benzyl)piperidin-3-yl)-1H-indazol-5-amine; Compound 1.041, which is N-(1-(3-(methylsulfonylmethyl)benzyl)piperidin-3-yl)-1H-indazol-5-amine; Compound 1.057, which is tert-butyl 3-((3-(1H-indazol-5-ylamino)piperidin-1-yl)methyl)benzylcarbamate; Compound 1.061, which is N-(1-(3-(aminomethyl)benzyl)piperidin-3-yl)-1H-indazol-5-amine; Compound 1.099, which is 2-(6-((3-(1H-indazol-5-ylamino)piperidin-1-yl)methyl)-1H-indol-1-yl)acetamide; Compound 1.101, which is 2-(6-((3-(1H-indazol-5-ylamino)piperidin-1-yl)methyl)-1H-indol-1-yl)ethanol; and Compound 1.122, which is N-(3-((3-(1H-indazol-5-ylamino)piperidin-1-yl)methyl)benzyl)acetamide.

17. The compound of claim 16, wherein Ar is phenyl.

18. The compound of claim 17, wherein X one of Y is $OR_8$, or $NR_8SO_2R_9$.

19. The compound of claim 18, wherein $R_8$ is H, alkyl, arylalkyl, cycloalkylalkyl, optionally substituted with $OR_{11}$, $NR_{11}SO_2R_{12}$, or $CONR_{11}R_{12}$.

20. A method for reducing intraocular pressure in a subject in need thereof, comprising the steps of:
identifying a subject in need thereof, and
administering to the subject the compound according to claim 15, in an amount effective to inhibit actomyosin interactions.

* * * * *